United States Patent
Joutras et al.

[11] Patent Number: 5,980,435
[45] Date of Patent: Nov. 9, 1999

[54] METHODS OF THERAPY OR CONTROLLED EXERCISE USING A JOINTED BRACE

[75] Inventors: Frank Edward Joutras; Ronald J. Hruska, Jr., both of Lincoln, Nebr.

[73] Assignee: Kinetecs, Inc., Lincoln, Nebr.

[21] Appl. No.: 08/494,528

[22] Filed: Jun. 23, 1995

Related U.S. Application Data

[63] Continuation-in-part of application No. 08/271,022, Jul. 6, 1994, which is a continuation-in-part of application No. 08/089,852, Jul. 9, 1993, Pat. No. 5,788,618.

[51] Int. Cl.⁶ .................................................. A63B 21/012
[52] U.S. Cl. .......................... 482/114; 482/115; 482/118; 482/5; 482/8
[58] Field of Search ................................. 482/112, 114, 482/115, 117, 118, 124, 4, 5, 8, 9; 601/33–35, 23, 5; 602/26, 27, 16, 20

[56] References Cited

U.S. PATENT DOCUMENTS

| | | |
|---|---|---|
| 246,984 | 9/1881 | Stillman . |
| 437,776 | 10/1890 | Gaze . |
| 2,439,100 | 4/1948 | Richards . |
| 2,543,729 | 2/1951 | Magida . |
| 2,832,334 | 4/1958 | Whitelaw ............................. 482/118 |
| 3,086,522 | 4/1963 | Frohmader . |
| 3,315,959 | 4/1967 | Carnielli . |
| 3,323,518 | 6/1967 | Swanson . |
| 3,515,384 | 6/1970 | Alexander . |
| 3,912,264 | 10/1975 | Busse et al. . |
| 4,159,111 | 6/1979 | Lowth . |
| 4,195,835 | 4/1980 | Hinds et al. . |
| 4,293,125 | 10/1981 | Hinds . |
| 4,326,708 | 4/1982 | Hinds . |
| 4,351,527 | 9/1982 | Crisp, Jr. . |
| 4,374,588 | 2/1983 | Ruggles . |
| 4,397,308 | 8/1983 | Hepburn . |
| 4,407,496 | 10/1983 | Johnson . |
| 4,485,808 | 12/1984 | Hepburn . |
| 4,489,718 | 12/1984 | Martin . |
| 4,508,111 | 4/1985 | Hepburn . |
| 4,538,595 | 9/1985 | Hajianpour . |
| 4,538,600 | 9/1985 | Hepburn . |
| 4,544,154 | 10/1985 | Ariel . |

(List continued on next page.)

FOREIGN PATENT DOCUMENTS

| | | |
|---|---|---|
| 0 103 490 A2 | 3/1984 | European Pat. Off. . |
| 1180022 | 9/1985 | U.S.S.R. ................................ 482/118 |
| 1454461 | 1/1989 | U.S.S.R. . |
| WO 87/00066 | 1/1987 | WIPO . |
| WO 88/02249 | 7/1988 | WIPO . |

OTHER PUBLICATIONS

"Use of a Knee–Brace for Control of Tibial Translation and Rotation", *The Journal of Bone and Joint Surgery, Incorporated*; vol. 72–A, No. 9, Oct., 1990, pp. 1323–1329.

Joint Active Systems, "Elbow Device" advertisement, copyright 1992.

*Advance for physical therapists*, Feb. 1, 1993, "Virtual World Helps Make Accessibility" article.

*Executive Golfer*, "Larry Nelson's Revolutionary Golf Exercise Club", p. 36, article on Protonic Exercise Club, Aug., 1992.

(List continued on next page.)

*Primary Examiner*—Jeanne M. Clark
*Attorney, Agent, or Firm*—Vincent L. Carney

[57] ABSTRACT

To provide controlled amounts of resistance to movement in exercise equipment or in orthotic devices, a control module has cooperating resistance elements. The force between the elements is varied in accordance with the position of the elements with respect to each other. For example the control module can connect two splints of a knee brace so that the resistance to flexion and extension are programmed in accordance with the position of the leg and thigh with respect to each other.

14 Claims, 33 Drawing Sheets

U.S. PATENT DOCUMENTS

| | | |
|---|---|---|
| 4,569,352 | 2/1986 | Petrofsky . |
| 4,625,962 | 12/1986 | Street . |
| 4,628,910 | 12/1986 | Krukowski . |
| 4,637,607 | 1/1987 | McArthur . |
| 4,644,938 | 2/1987 | Yates et al. . |
| 4,649,906 | 3/1987 | Spademan . |
| 4,665,900 | 5/1987 | Saringer . |
| 4,669,451 | 6/1987 | Blauth et al. . |
| 4,674,741 | 6/1987 | Pasierb, Jr. et al. . |
| 4,678,184 | 7/1987 | Neiger et al. . |
| 4,691,694 | 9/1987 | Boyd et al. . |
| 4,718,665 | 1/1988 | Airy et al. ................................ 602/16 |
| 4,726,582 | 2/1988 | Fulus ........................................... 482/5 |
| 4,733,656 | 3/1988 | Marquette . |
| 4,741,529 | 5/1988 | Bloemendaal .......................... 482/118 |
| 4,747,595 | 5/1988 | Mabry et al. . |
| 4,751,917 | 6/1988 | Ruf . |
| 4,765,315 | 8/1988 | Krukowski . |
| 4,772,012 | 9/1988 | Chesher . |
| 4,772,015 | 9/1988 | Carlson et al. . |
| 4,795,148 | 1/1989 | Rangaswamy . |
| 4,801,138 | 1/1989 | Airy et al. . |
| 4,817,588 | 4/1989 | Bledsoe . |
| 4,822,037 | 4/1989 | Makansi et al. . |
| 4,824,132 | 4/1989 | Moore . |
| 4,850,585 | 7/1989 | Dalebout ................................ 482/118 |
| 4,856,500 | 8/1989 | Spademan . |
| 4,862,875 | 9/1989 | Heaton . |
| 4,869,492 | 9/1989 | Joutras . |
| 4,869,497 | 9/1989 | Stewart et al. . |
| 4,875,469 | 10/1989 | Brook et al. . |
| 4,885,939 | 12/1989 | Martin . |
| 4,905,676 | 3/1990 | Bond et al. . |
| 4,907,797 | 3/1990 | Gezari et al. . |
| 5,037,088 | 8/1991 | Bernstein ................................ 482/118 |
| 5,052,379 | 10/1991 | Airy et al. .............................. 482/112 |
| 5,062,633 | 11/1991 | Engel et al. ............................. 482/118 |
| 5,116,296 | 5/1992 | Watkins et al. . |
| 5,117,814 | 6/1992 | Luttrell et al. . |
| 5,144,943 | 9/1992 | Luttrell et al. . |
| 5,147,265 | 9/1992 | Pauls et al. . |
| 5,158,519 | 10/1992 | Hughes ................................... 482/118 |
| 5,201,772 | 4/1993 | Maxwell . |
| 5,263,911 | 11/1993 | Frydman . |
| 5,313,942 | 5/1994 | Platzker . |
| 5,331,851 | 7/1994 | Parviainen et al. . |
| 5,358,468 | 10/1994 | Longo et al. ........................... 482/112 |

OTHER PUBLICATIONS

Three–D Orthopedic, Inc., brochure for Low Profile Walker, copyright, 1990.
DePuy brochure on lower leg braces, copyright 1988.
Orthomerica Products, Inc., Prime Orthosis brochure, copyright 1991.
Orthomerica Products, Inc., brochure on The Newport System, copyright 1989.
*The American Journal of Sports Medicine*, vol. 14, No. 4, "Instrumented testing of functional knee braces", pp. 253–256, by Charles Beck et al.
"University of Michigan Brace Study", Fall, 1989.
*American Journal of Sports Medicine*, vol. 17, No. 2, 1989, "Comparison of rehabilitative knee braces, A biochemical investigation", by Patrick W. Cawley et al.
*American Journal of Sports Medicine*, vol. 18, No. 3, 1990, "The efficacy of a prophylactic knee brace to reduce knee injuries in football" by Michael Sitler et al.
Zimmer Sports–Caster Derotational/A.C.L. Brace brochure, copyright 1990.
Dynasplint Systems, Inc. brochure "The Choice Therapy for a Greater Range of Motion" copyright 1988.
Dynasplint Systems, Inc. brochure, copyright 1990.
Dynasplint Systems, Inc. brochure for joint stiffness, copyright 1989.
Dynasplint Systems, Inc. brochure to resolve immobilization stiffness and Established Contractures, copyright 1987.
*The Journal Of Orthopaedic and Sports Physical Therapy*, Copyright 1987 by "Case Studies: Contracture and Stiff Joint Management with Dynasplint" by George R. Hepburn, pp. 498–504.
*In–Motion*, vol. 04, 1990, Thera–kinetics, Inc. publication.
Bio Tec, Inc. Ultraflex brochure, copyright 1990.
LMB Hand Rehab Products, Inc. product catalog, copyright 1990.
McDavid Knee Guard, Inc., Sports Medical products 1991 catalog.
Brace Technologies, Inc. brochure on PCL Brace, copyright 1991.
Sports Supports Swedish Knee Brace brochure, Product Release No. 1170 May 1, 1991.
Sports Supports brochure on Clinic Private Label, copyright 1991.
Booklet entitled "Arthroscopy Looking into Your Knee Problem" by Krames Communications, copyright 1983, 1984, 1985.
*Topics in Acute Care and Trauma Rehabilitation*, Oct. 1988, "Functional knee bracing for skiing: A review of factors affecting brace choice" by Patrick W. Cawley, pp. 73–81.
*JOSPT* 11:10 Apr., 1990, "A Comparative Support Evaluation of Three Ankle Orthoses Before, During, and After Exercise" by Tracy A. Greene et al.
Mueller Sports Medicine, Inc. brochure and price list on neoprene knee braces & supports dated Feb., 1991.
Magnum Orthopedic, A Division of Mueller Sports Medicine, Inc. brochure on the Competition Brace, 1989.
Brochure by Life Fitness for the Lifecircuit system, copyright, 1993.
Brochure by Empi, Inc., for the UltraFlex brace, copyright, 1992.
Clinical Instruction Manual by LMB for the Pro–Glide wrist orthoses, copyright, 1993.
Brochure by Omni Scientific, Inc., for Duo–Loc Ankle Support, copyright, 1990.
Brochure by Omni Scientific, Inc., for Duo–Loc Ankle Support, copyright, 1990.
Brochure by Omni Scientific,Inc., for the Omni–Glide support, copyright, 1989.
Pamphlet by DuraGold entitled "Post–Op Cryotherapy and DuraKold", Nov., 1989.
Brochure by Omni Scientific, Inc., for the OS–5 brace, copyright, 1990.
Brochure by Omni Scientific, Inc., for the TS–7 knee support, copyright, 1990.
"Low–load, Prolonged Stretch in Treatment of Elbow Flexion Contractures Secondary to Head Trauma: A Case Report", *Physical Therapy*, vol. 69, No. 4, Apr., 1989, by Marilyn MacKay–Lyons, pp. 292–296.
"Treatment of Exposed Bilaterial Achilles Tendons with Use of the Dynasplint" *Physical Therapy*, vol. 68, No. 6, Jun., 1988, by Reginald L. Richard, et al., pp. 989–991.
"Patelofemoral Problems After Anterior Cruciate Ligament Reconstruction" *The Americal Journal of Sports Medicine*, vol. 17, No. 6, 1989, by Raymond A. Sachs, et al., pp. 760–765.

Brochure by Protectair Limited for the InCare Elbow brace, copyright, 1991.

Booklet entitled "Innovation Sports Update", vol. 13, 1989, published by Innovation Sports.

Brochure by Protectair Limited for the InCare knee brace, copyright, 1991.

Brochure by Smith & Nephew DonJoy for the S.T. Walker, Rev 9–90.

Brochure by Sutter Corporation for the Sportlite 2Step knee brace, copyright, 1989.

Brochure by Smith & Nephew DonJoy, Inc., for the Extension Lock Splint, Rev. 9–90.

Brochure by Medical Technology, Inc., for the Bledsoe Arm Brace, copyright, 1988.

Brochure by Medical Designs, Inc., for the hip stabilizer, copyright, 1990.

Brochure by Medical Designs, Inc., for the Universal Leg Brace System, copyright, 1990.

Brochure by Medical Designs, Inc., for the the Universal Arm–Wrist Bracing System, copyright, 1989.

Brochure by Medical Designs, Inc., for an anatomical boot, copyright, 1989.

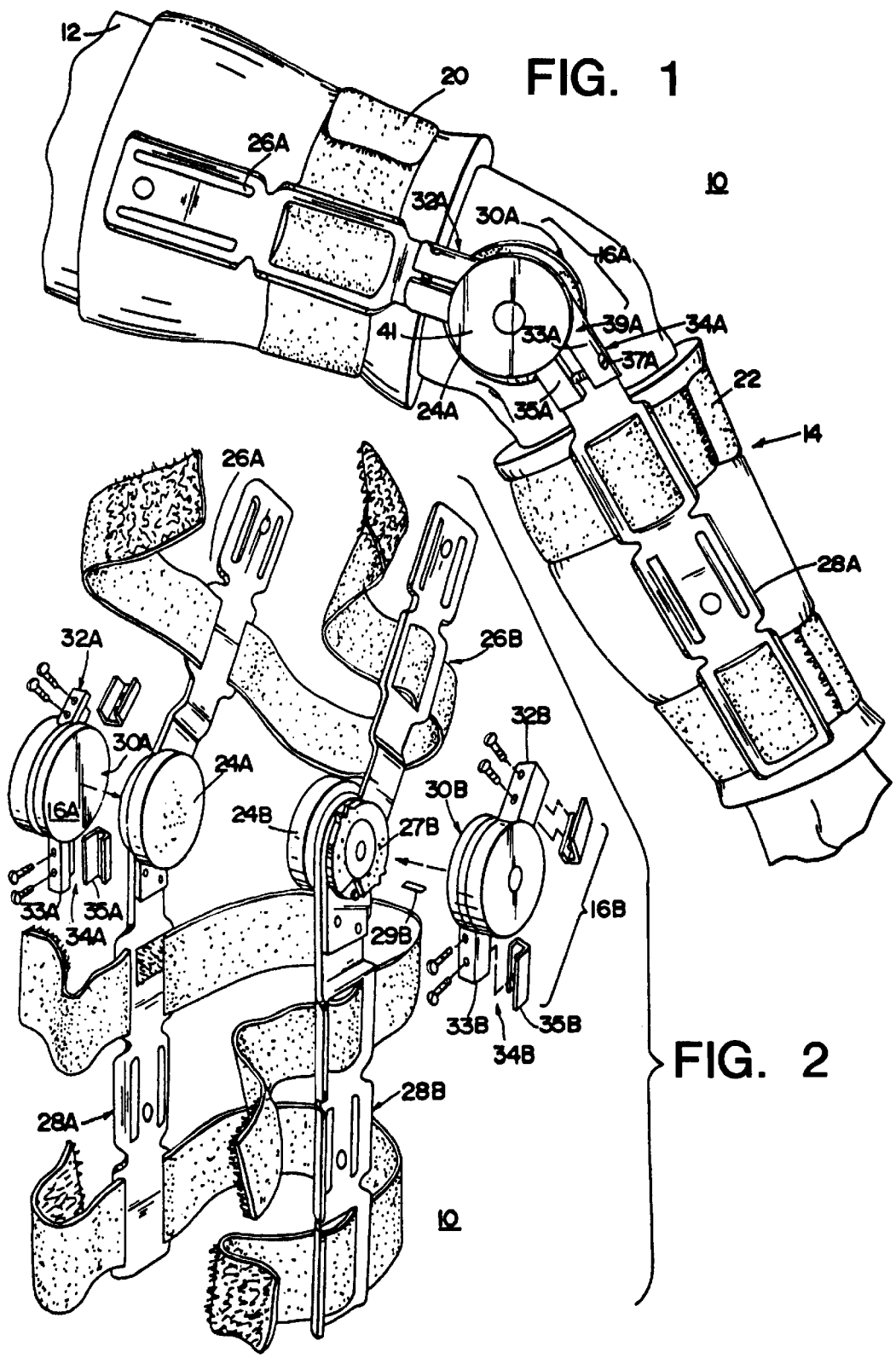

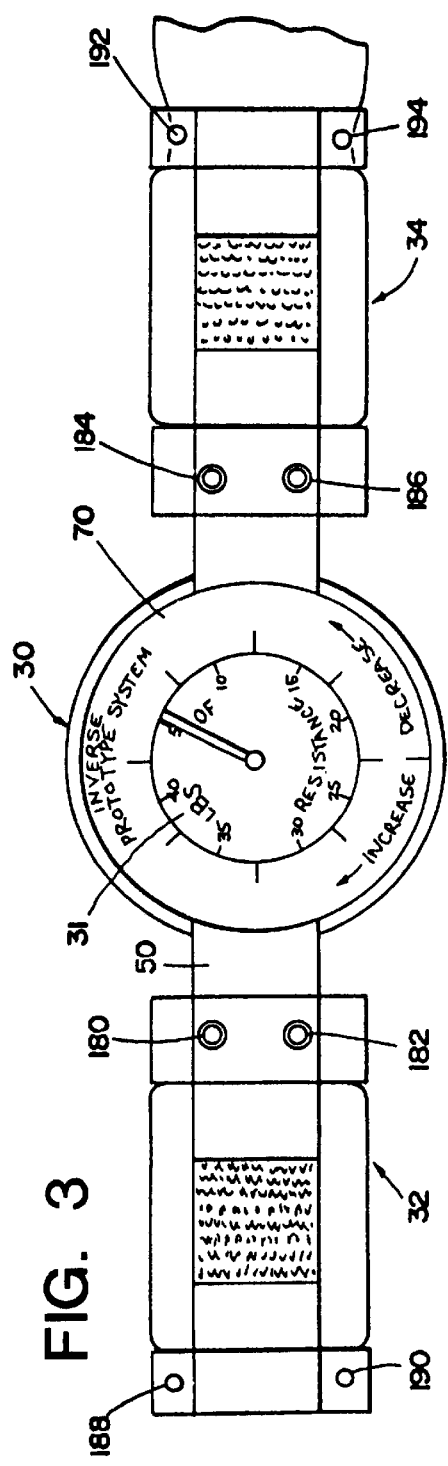
FIG. 3
FIG. 4
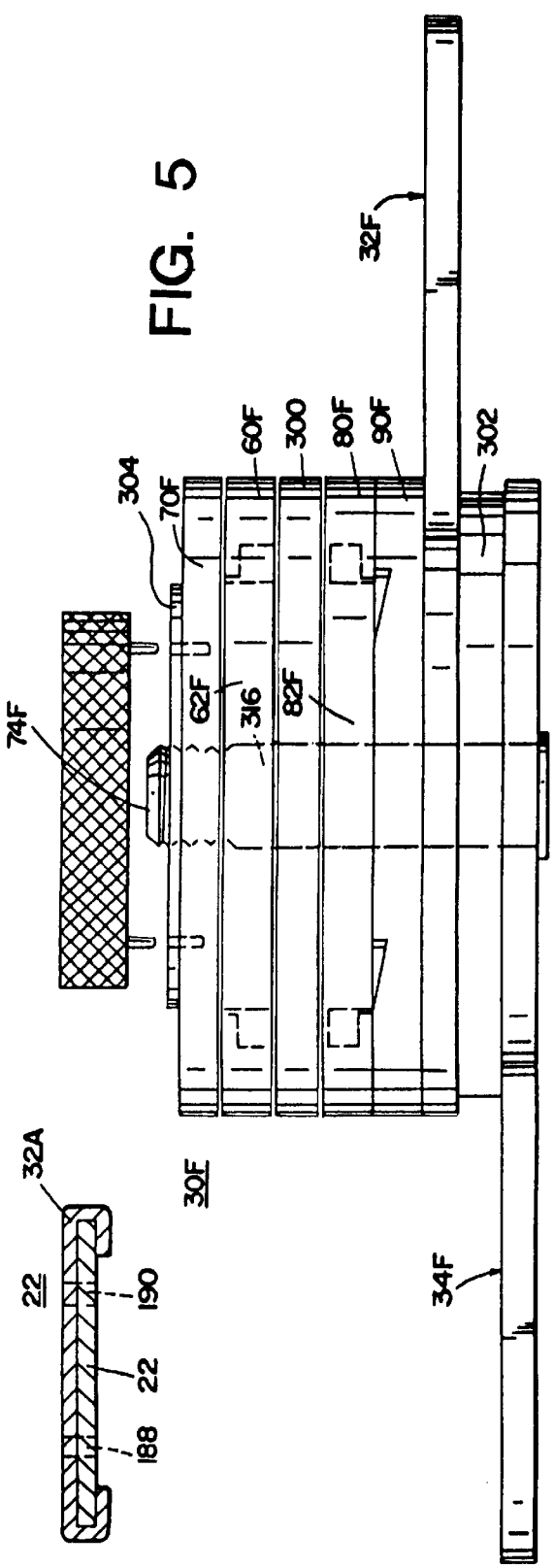
FIG. 5

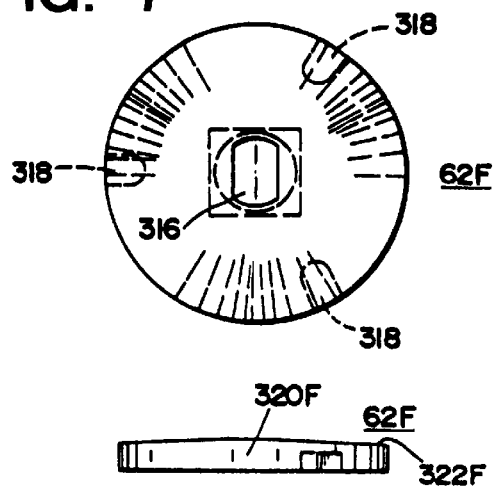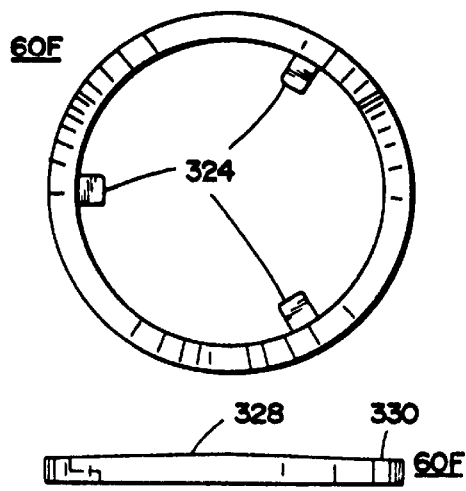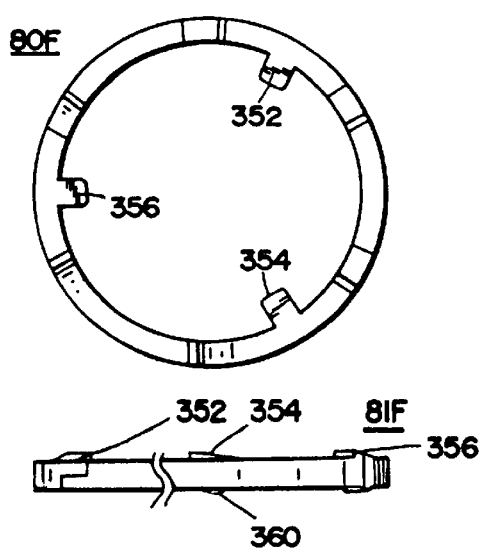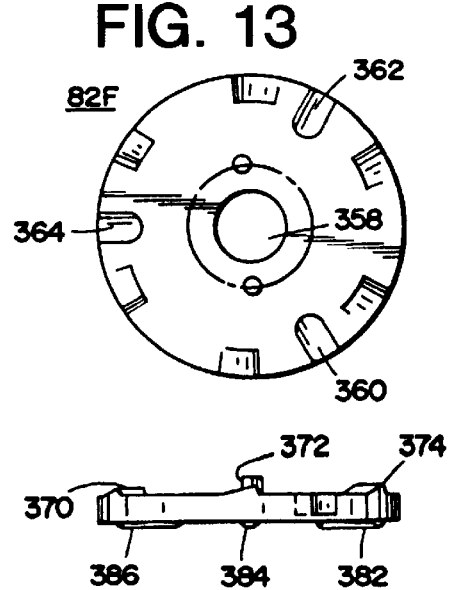

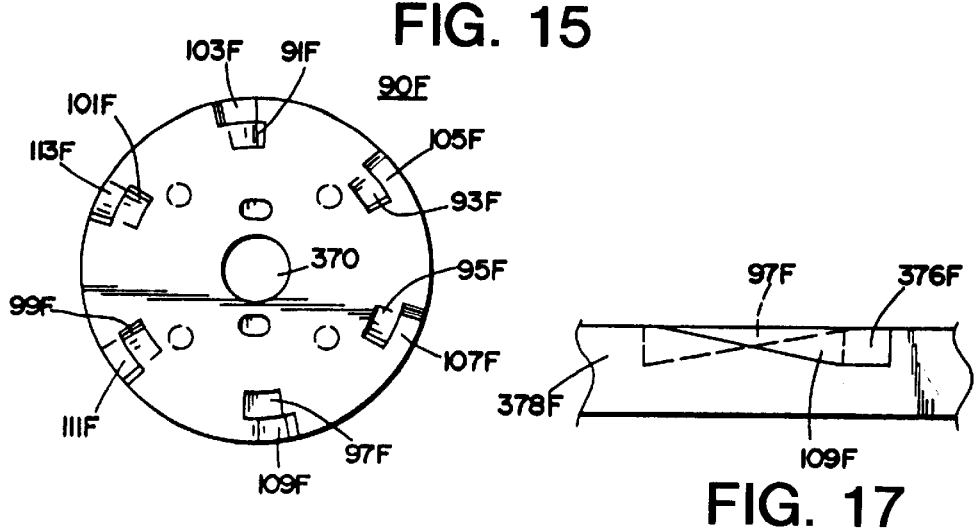
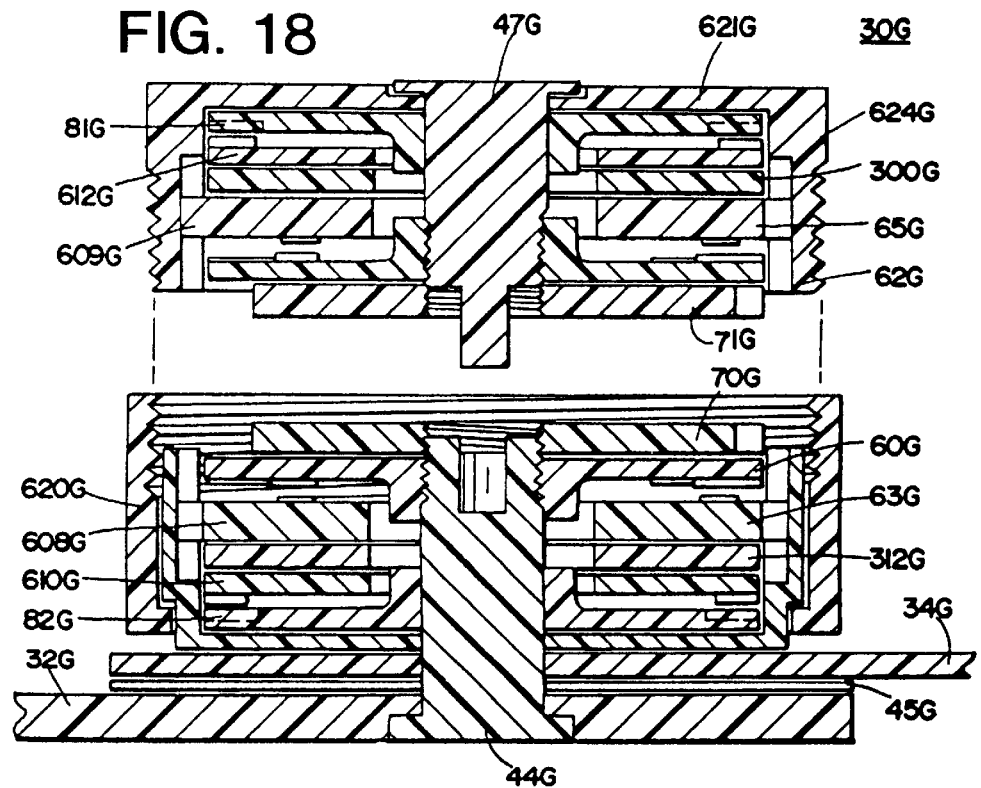

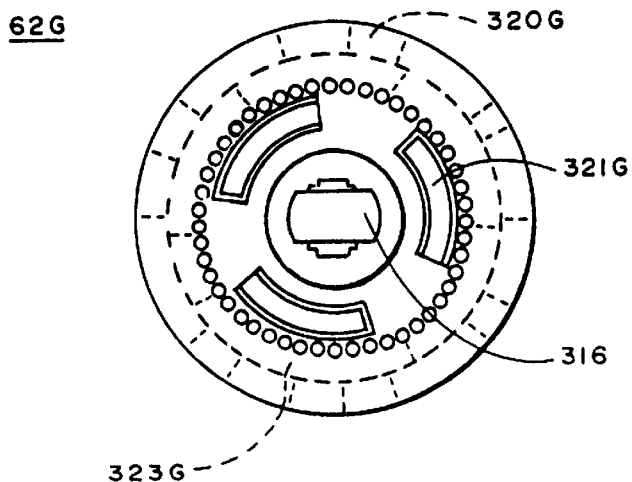
FIG. 20
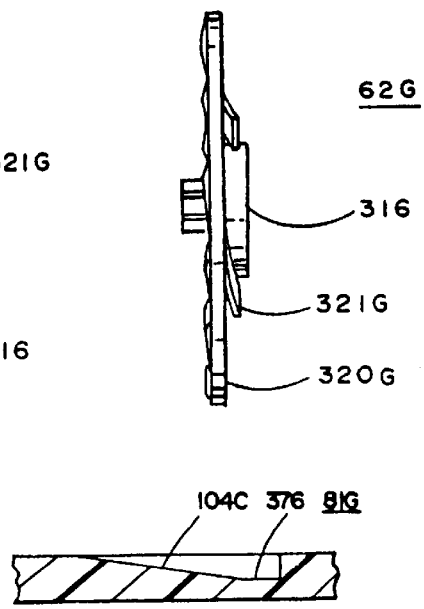
FIG. 21
FIG. 26
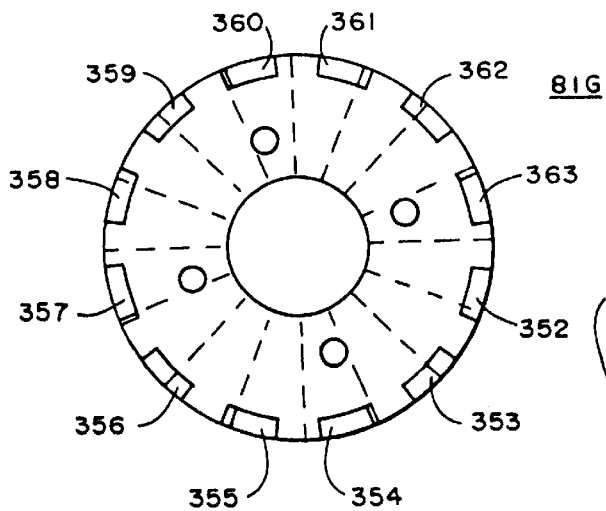
FIG. 22
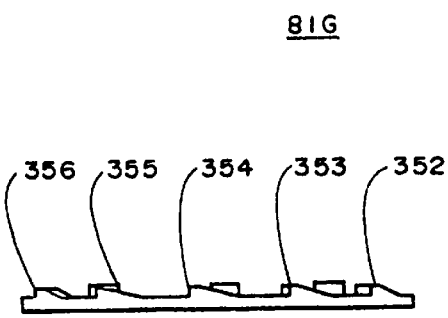
FIG. 23

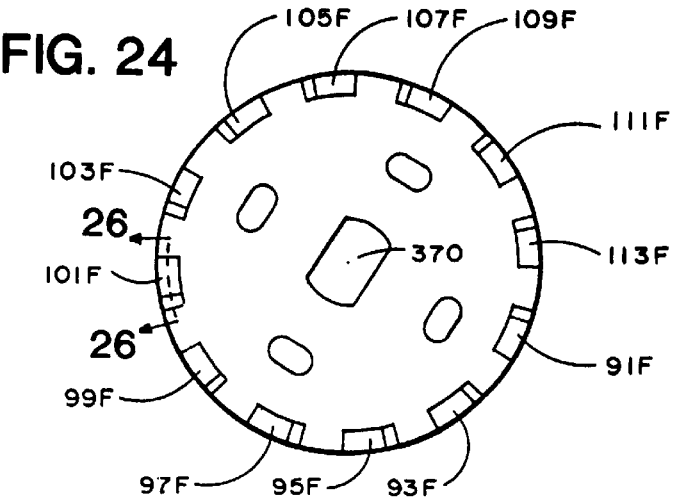
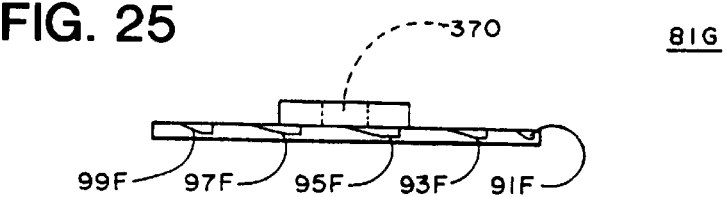
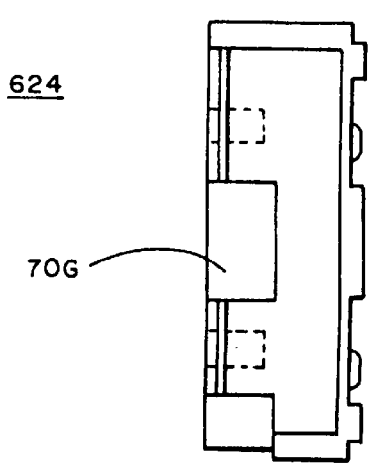
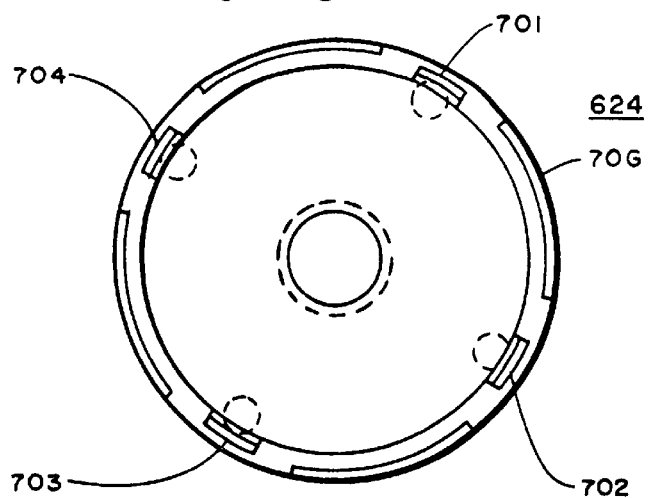

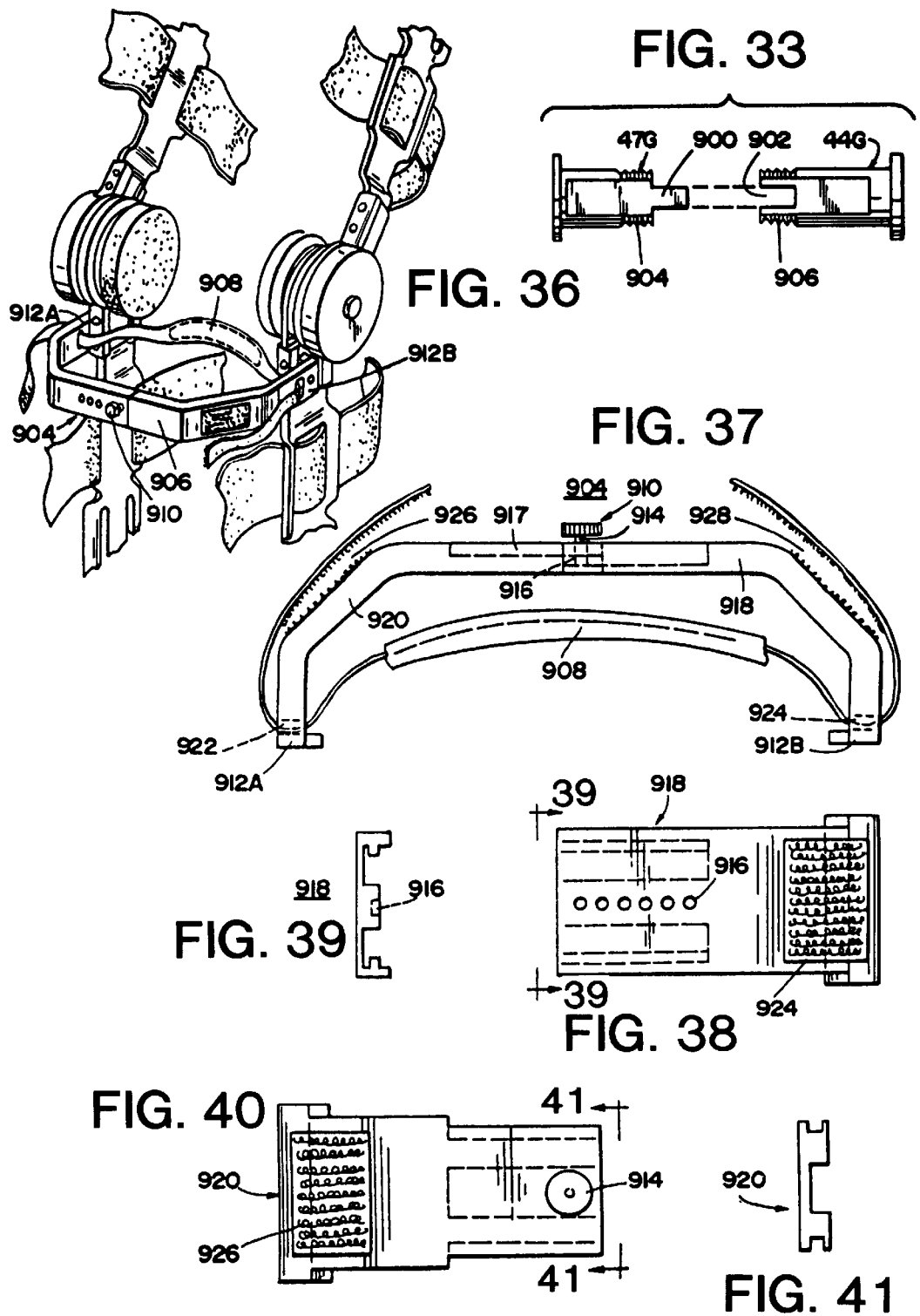

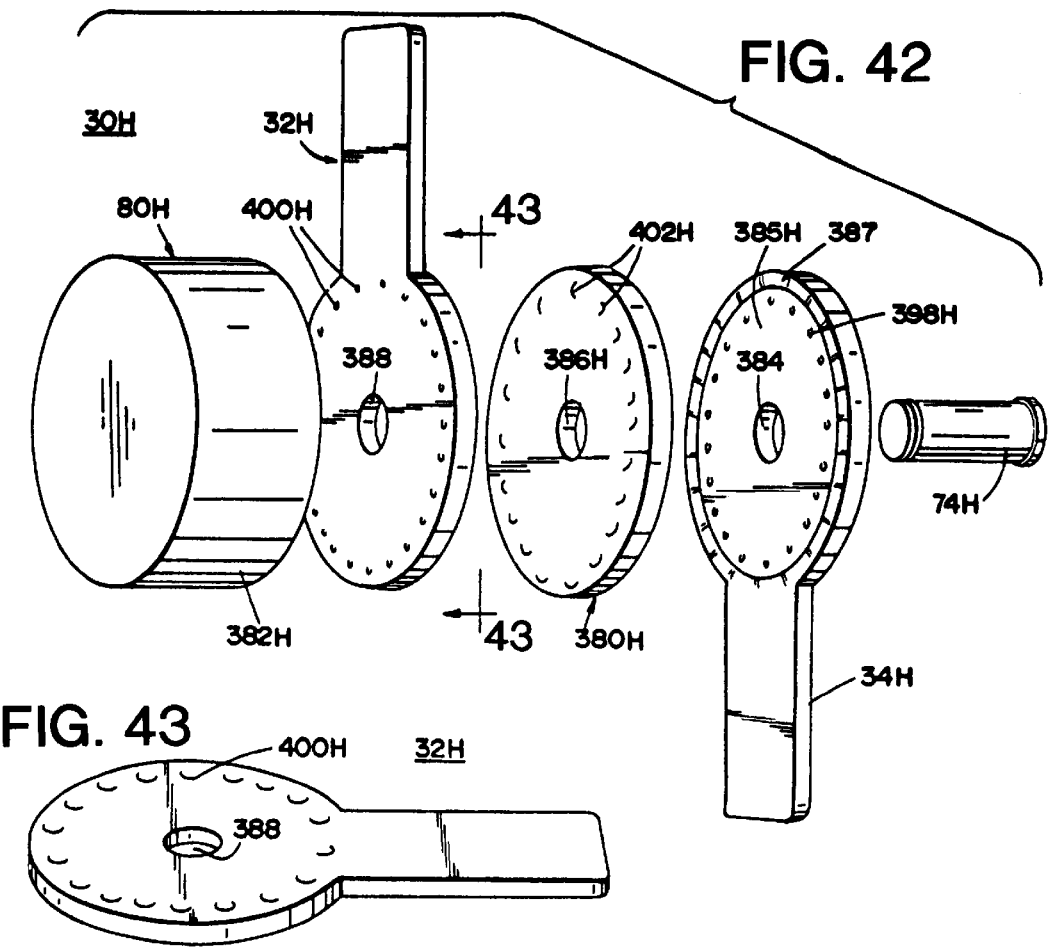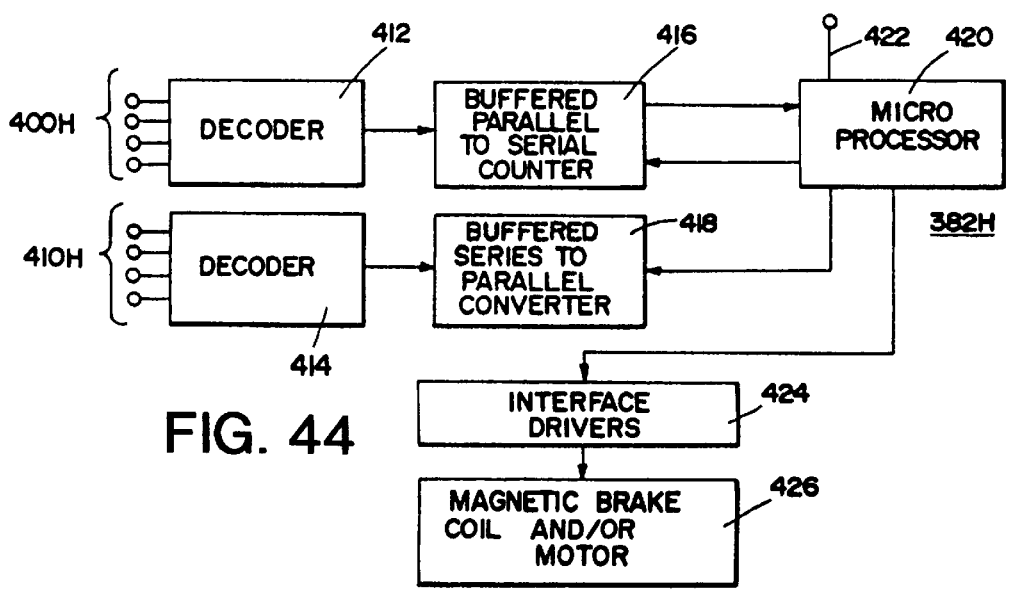

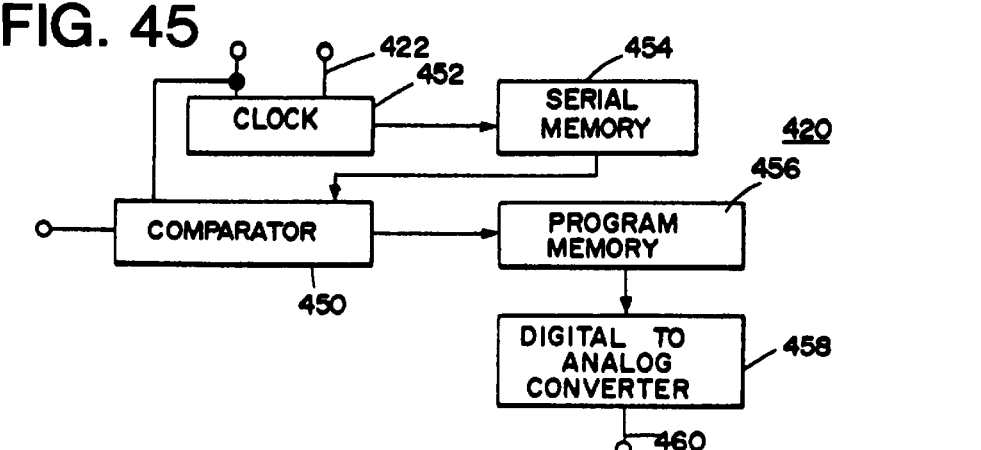
FIG. 45
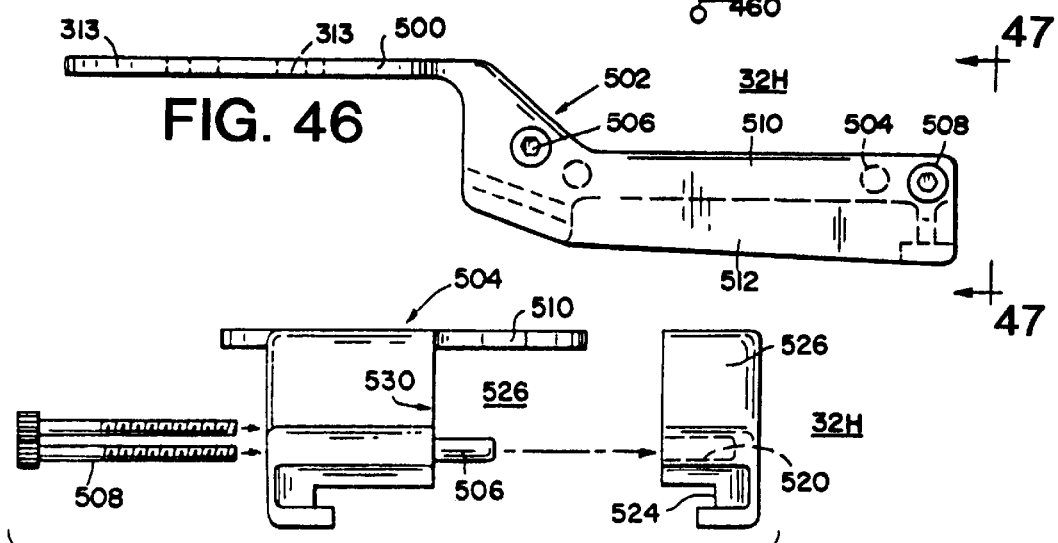
FIG. 46
FIG. 47
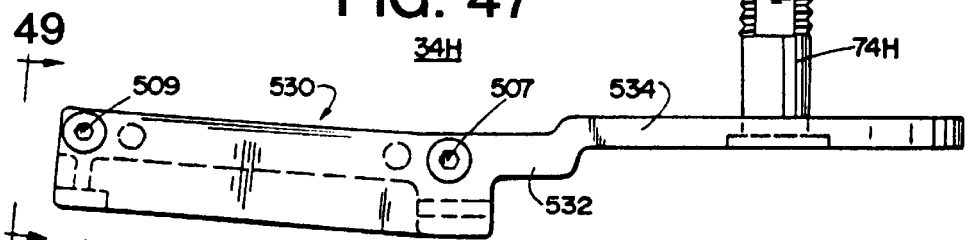
FIG. 48
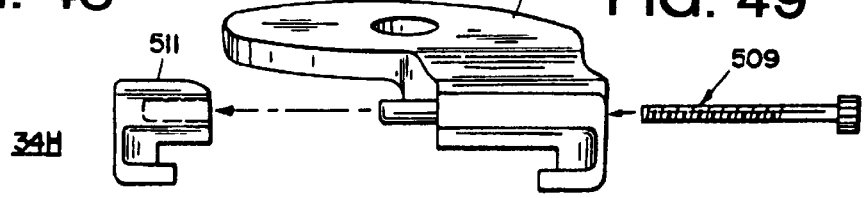
FIG. 49

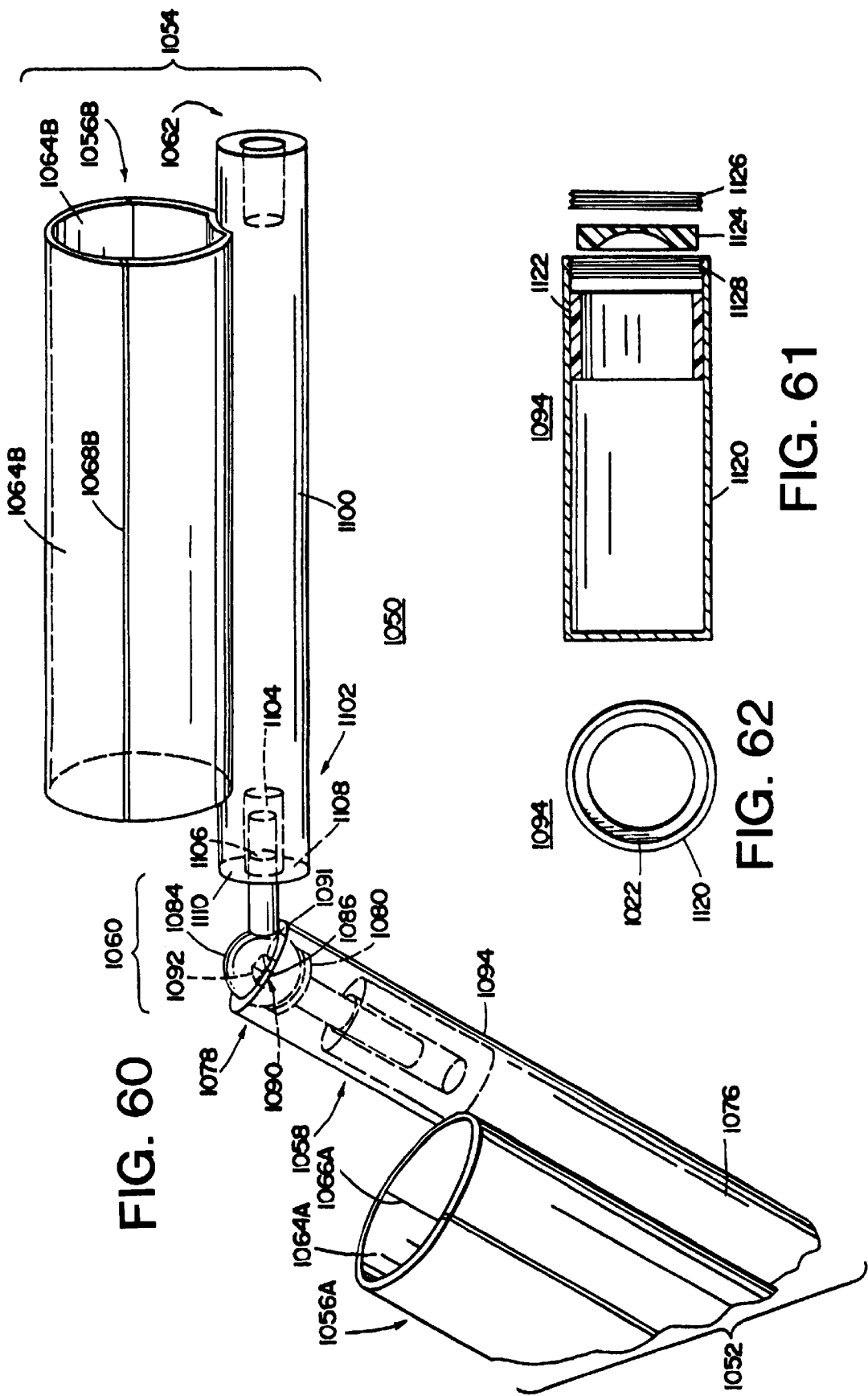

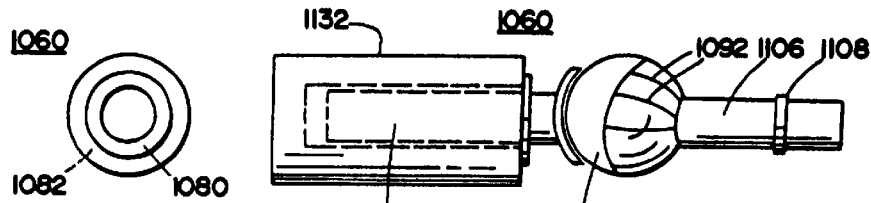
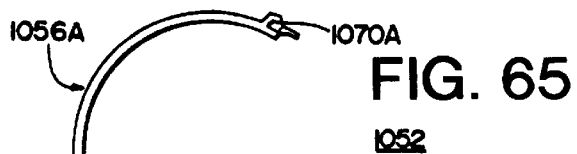
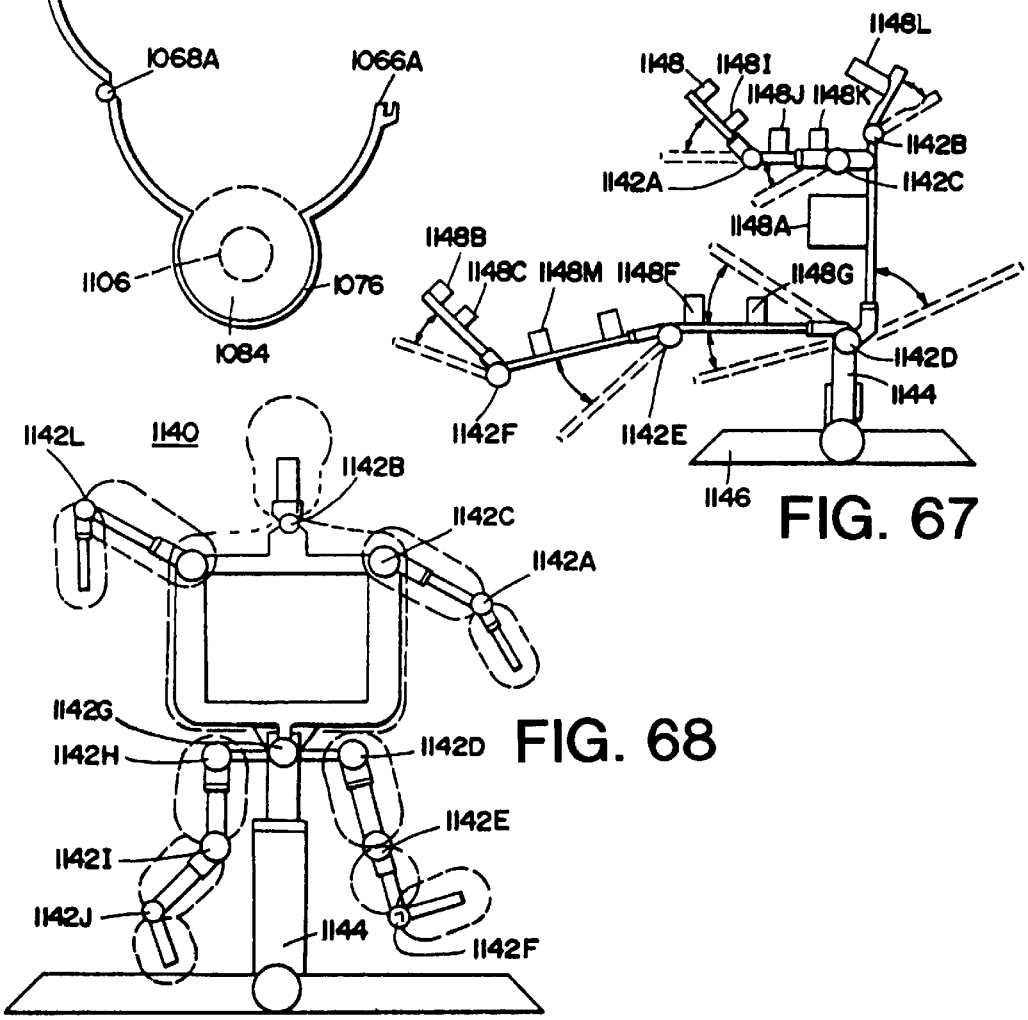

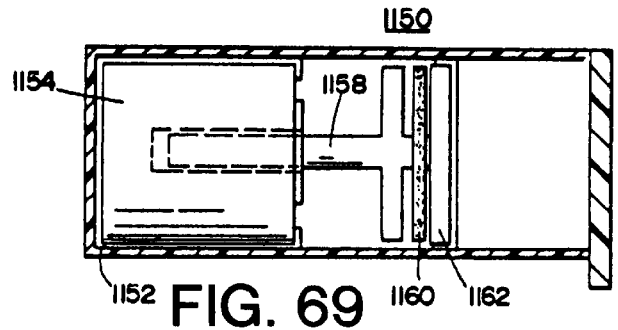
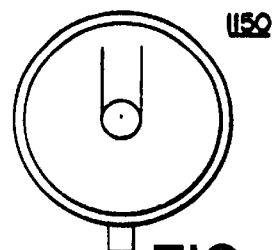
FIG. 69     FIG. 70
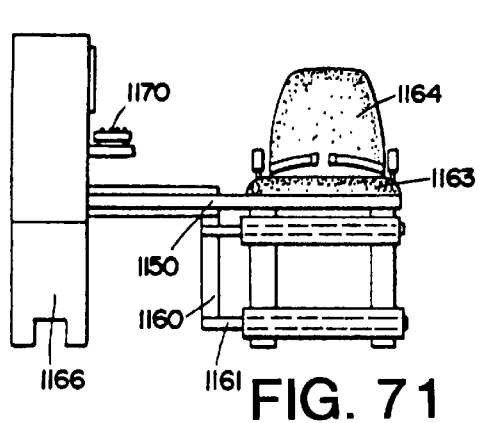
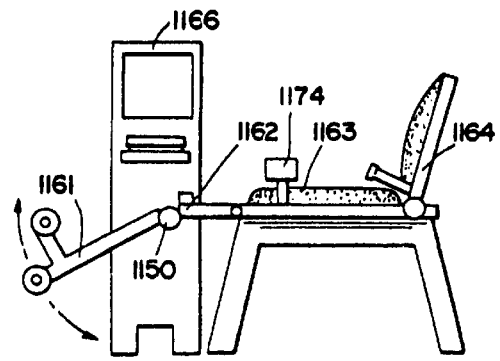
FIG. 71     FIG. 72
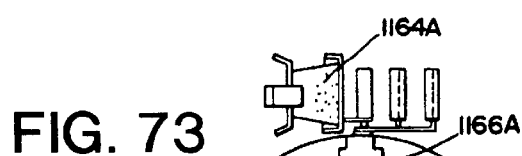
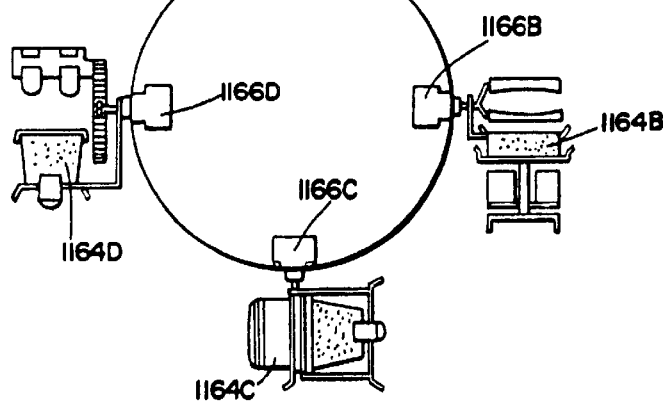
FIG. 73

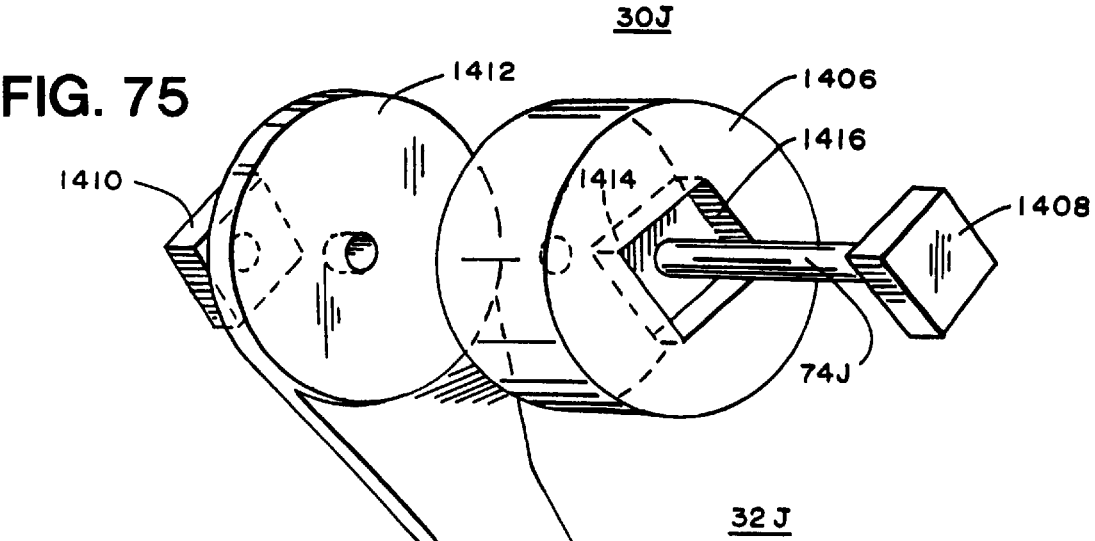
FIG. 75
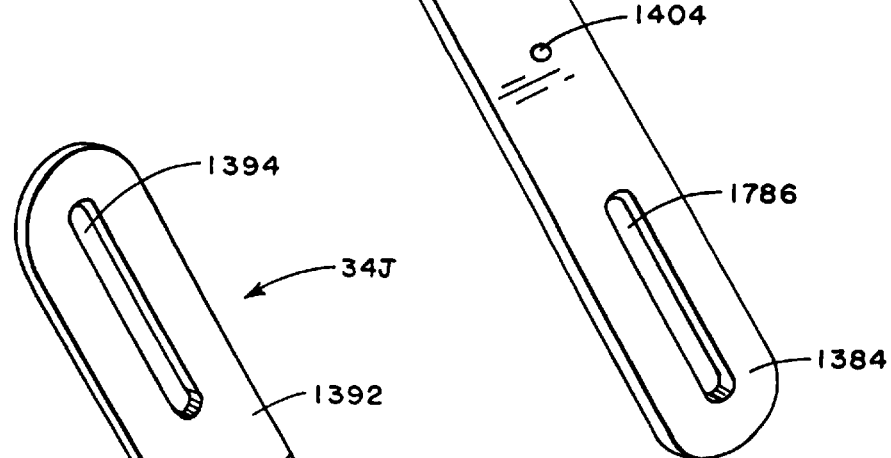
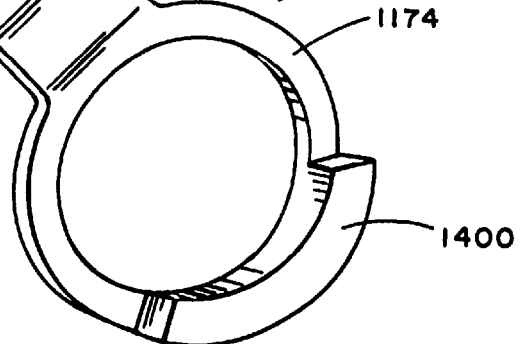
FIG. 76

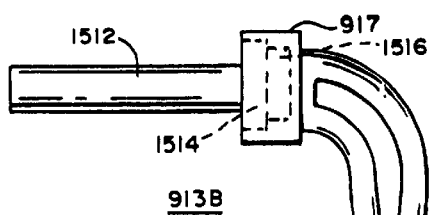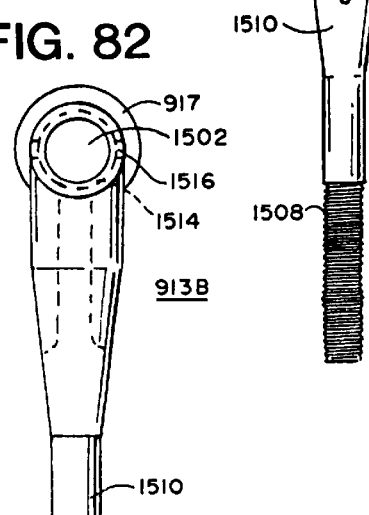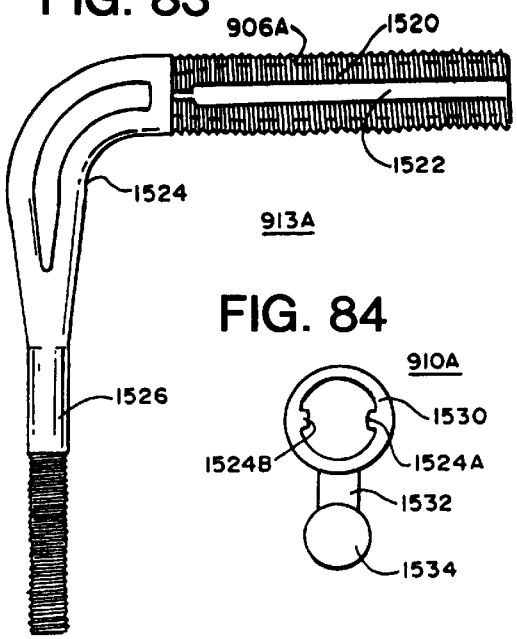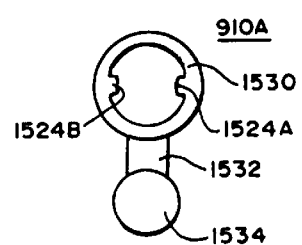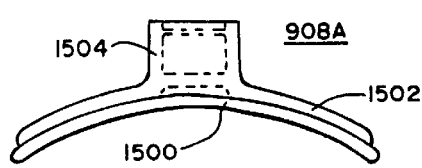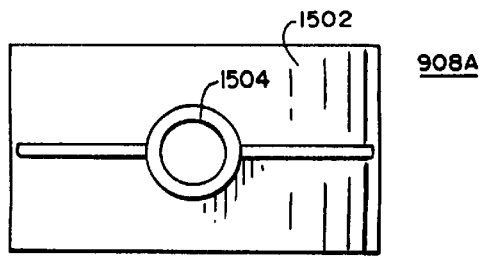

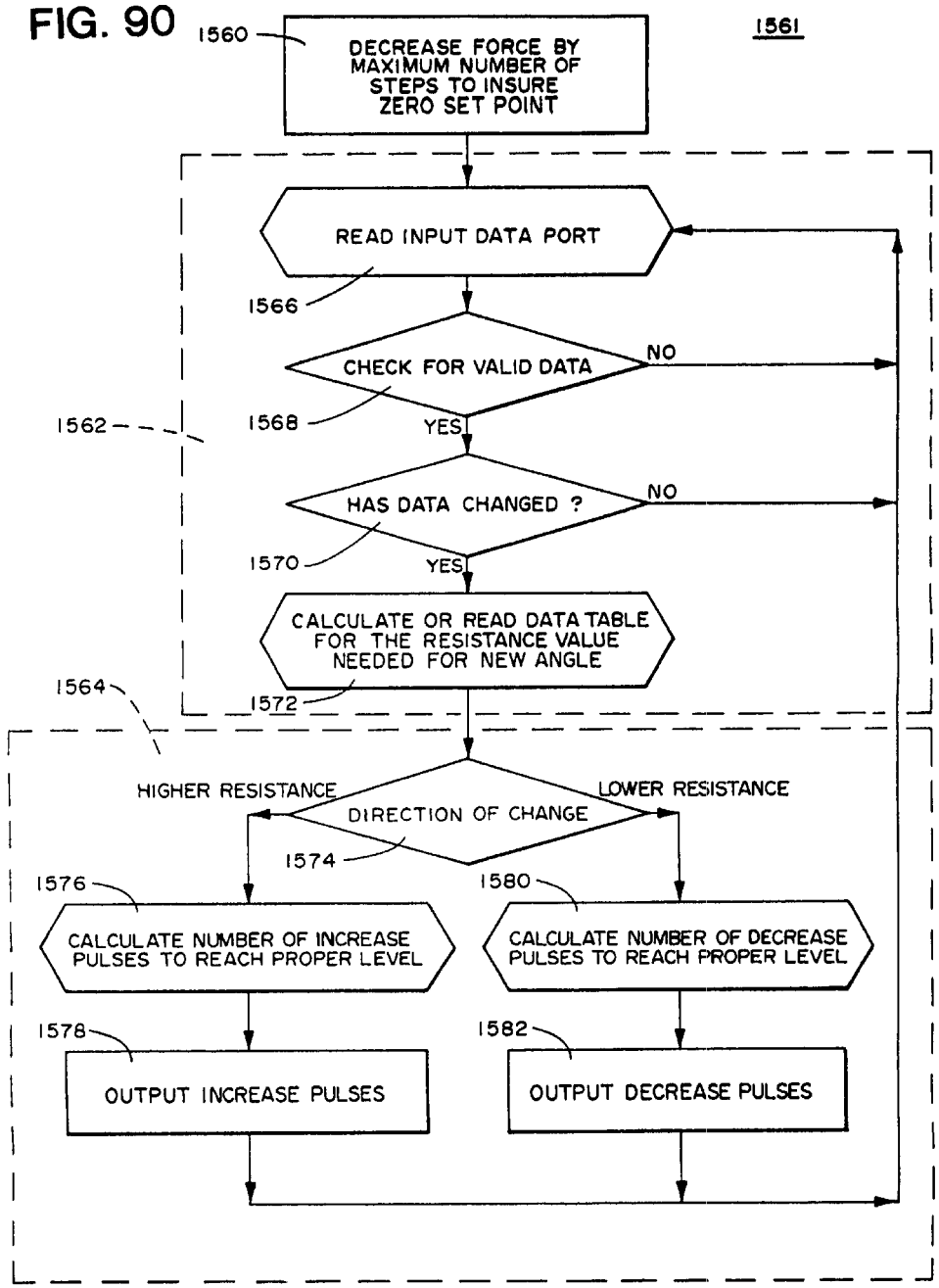

METHODS OF THERAPY OR CONTROLLED EXERCISE USING A JOINTED BRACE

RELATED CASES

This application is a continuation-in-part of U.S. application Ser. No. 08/271,022 filed Jul. 6, 1994, which is a continuation-in-part of U.S. application Ser. No. 08/089,852 filed Jul. 9, 1993, now U.S. Pat. No. 5,788,618 for EXERCISE APPARATUS AND TECHNIQUE.

BACKGROUND OF THE INVENTION

This invention relates to apparatuses and methods for providing controlled exercise and support.

Braces for jointed anatomical limb segments such as the leg and thigh or the arm and forearm are known. The braces have joints that permit motion of the limb segments, such as for example, motion of the leg with respect to the thigh about the knee, the thigh and trunk about the hip, the arm and trunk about the shoulder and the forearm and arm about the elbow. Such braces may include stops to limit motion.

In one class of exercise equipment, provision is made to attach the exercise equipment to a brace-like structure or to a brace-like fastening means that is part of the equipment. This type of brace-like equipment attaches to the limb segments to permit exercise of the braced part, such as for example, to permit or limit exercise of the leg and thigh about the knee or the arm and forearm about the elbow.

Prior art exercise techniques are conventionally classified as isometric, isotonic, and isokinetic. An additional fourth classification has become recently recognized and called individualized dynamic variable resistance. All of these techniques except isometric utilize motion of the limb for strengthening or treating an injured muscle and all of the techniques have corresponding exercise equipment associated with them.

One type of prior art isokinetic technique and corresponding exercise equipment is machine operated. The patient moves and either flexes a joint through predetermined range using motor control and resists movement by the patient with a force proportional to the speed of movement of the patient. This type of equipment has the disadvantage of being expensive, and under some circumstances, of not providing a controlled level of muscular exertion appropriate for the position of the parts being exercised since it is stationed on a fixed surface such as the floor.

Isotonic exercise equipment includes weights and a mechanism for applying the weights to the anatomical segment so that the patient exerts effort against the weights. This type of prior art exercise equipment has the disadvantages of: (1) continuously providing resistance of the same amount regardless of the position of the limb being exercised; (2) continuance of the force when the patient stops moving if the weight is elevated; and (3) being only unidirectional in a concentric (shortening muscle) sense.

A newer type of prior art exercise equipment and technique involving motion is individualized dynamic variable resistance. This equipment measures a limb's strength ability isokinetically to establish a motor performance curve. This curve is a relationship between degrees and the range of motion and resistance to that motion. During exercising, the resistance is provided over a distance corresponding to the range of motion as a fixed percentage of the maximum established by that curve. The curve is followed but at a preset level such as one-fourth of its maximum value.

In the equipment using this technique, the curve is measured and recorded and then during exercise, a feedback mechanism senses the position and obtains a signal corresponding to the proportion of resistance corresponding to that position. This signal controls the amount of force applied through a magnetic particle brake attached to the limb. Equipment utilizing this technique is disclosed in U.S. Pat. No. 4,869,497 granted Sep. 26, 1989.

This technique has several disadvantages under certain circumstances, such as: (1) continuing a resistive force after motion has stopped; (2) being adaptable only to open kinetic chain exercise; (3) being dependent to some extent on controlled speed of movement to provide the appropriate resistance; (4) the equipment is fixed to a particular locality when in use, as well as to the patient; (5) the equipment is bulky and cannot be easily moved from place to place; and (6) the user may inadvertently use other muscles to change the exercise pattern because the muscle cannot be easily isolated with equipment mounted to equipment on which the patient sits or stands or to the ground since the patient may be able to exert leverage with another part of the body. This technique also has the disadvantage of being too inflexible and not accomodating resistance programs developed for specific purposes; such as to strengthen fast twitch or slow twitch muscles individually or for a program prescribed to accomodate a particular limb position for development of particular muscles in a manner deviating from the motor performance curve.

SUMMARY OF THE INVENTION

It is an object of the invention to provide a novel exercise mechanism and technique.

It is a further object of the invention to provide an exercise device that may be attached to exsisting braces or specific designed exercise braces, such as lower extremity braces or upper extremity braces and provide for controlled exercise of the person wearing the brace.

It is a further object of the invention to provide an inexpensive and easily applied technique for providing controlled resistance therapy for persons with injured extremities or joints or possibly other body parts.

It is a still further object of the invention to provide a novel exercise device and technique that provides resistance to movement that is related in a precontrolled manner to the position of the part being exercised.

It is a still further object of the invention to provide a novel technique and apparatus to aid users in moving through an appropriate range of motion.

It is a still further object of the invention to provide a novel apparatus and technique for reducing pain during movement.

It is a still further object of the invention to provide a novel apparatus and method for maintaining proper joint alignment during movement.

It is a still further object of the invention to provide a novel apparatus and method for reducing arthrokinetic joint movement dysfunction.

It is a still further object of the invention to provide an exercise device and technique that provides resistance to movement that is related in a pre-programmed manner to the position of the part being exercised but is applied independently of speed.

It is a still further object of the invention to provide a novel exercise device and technique that permits tailored exercise programs for a wide variety of purposes, such as to strengthen principally the fast twitch muscle or the slow twitch muscle or to strengthen only certain portions of an injured muscle.

It is a still further object of the invention to provide a novel exercise device and technique utilizing motion in which the user can vary the speed along a resistance program which provides resistance to movement related to position.

It is a still further object of the invention to provide a novel exercise technique and apparatus which does not provide a force when the person doing the exercise stops attempting to move but which is nonetheless independent of speed of motion by the person doing the exercising.

It is a still further object of the invention to provide a novel exercise technique and device which permits particular muscles to be isolated since it is only attached to the patient and not to an object upon which the patient is sitting or standing.

It is a still further object of the invention to provide a novel exercise device which is coupled to images or other sensed programs so that the user can correlate muscle activity with sensed events.

It is a still further object of the invention to provide a device and method that enables equipment such as ski boots or the like to have useful amounts of motion with resistance to movement in controlled directions so as to be less likely to cause injury.

It is a still further object of the invention to provide a novel exercise device and technique in which the resistance to movement is related in a manner programmed by a therapist to correspond to the position of the part being exercised but not necessarily proportional to an average motor performance curve throughout the range of motion but instead constructed for specific purposes.

It is a still further object of the invention to provide a versatile exercise device that can be conveniently applied to either open kinetic chain exercise or closed kinetic chain exercise.

It is a still further object of the invention to provide a technique and equipment for combining resistance to movement that is related in a precontrolled manner to the position of the part being moved with electrical muscle stimulation to aid movement or prevent undesired movement.

It is a still further object of the invention to provide an exercise device and technique that provides resistance to movement that is related in a pre-programmed manner to the position of the part being moved and/or provides electrical muscle stimulation at least partly controlled by electrical myography (EMG) and/or other biofeedback measurement (e.g. force plate).

In accordance with the above and further objects of the invention, one embodiment of exercise device is part of or may be attached to a brace for a body part. It may include means for fastening the exercise device to a limb brace or brace for another body part to control the amount of force needed to flex or extend the braced extremity or limb or other body part about a joint. The means for fasteneing may include pads and means for adjusting the location of the pads to avoid irritation or damage to the body such as irritation of burns. In a preferred embodiment, the means for controlling the amount of force includes one or more frictional resistance members that are removably attachable to a conventional brace to provide a desired resisting force to movement.

The frictional resistance members may include either: (1) a mechanism that releases for free movement in one direction and moves with resistance against force in the other direction; or (2) a mechanism that provides controlled variable or constant resistance in either or both directions. Adjustable stops or limit members to control the amount or range of motion may be provided. The resisting force may be provided by force members such as springs or motors or stretchable members or pneumatic cylinders or the like.

Friction members and pressure members that work together to provide frictional force against movement are used in the preferred embodiment because mechanisms that use friction to control the amount of resistance to motion: (1) are relatively easy to adjust for different amounts of resisting force; and (2) do not provide force except to resist motion of the exercised limb. One technique for adjusting the amount of resistance is to adjust the pressure normal to frictional surfaces that move with respect to each other. The resistance stops when motion or force applied by the patient to cause motion stops and the exercise device does not move or exert force except when providing a resisting force to motion by the person using it.

In one embodiment, a knee brace or elbow brace includes first and second sections connected at a pivot point. For one use, the first section is attachable to the leg (tibia and fibula) by a first connecting means and the second section is connected to the thigh (femur) by a second connecting means. For another use, the first section is attachable to the forearm (radius and ulna) by a first connecting means and the second section is connected to the arm (humerus) by a second connecting means. In either use, a first lever in the first section removably snaps onto the first connecting means and a second lever in the second section removably snaps onto the second connecting means, with the two levers being connected to a friction control module centered at the pivot point. The friction control module controls the amount of friction or resistance against which the first and second connecting means move.

In some embodiments, frictional members are moved with respect to each other as the two levers move. The amount of friction is controlled: (1) in some embodiments, by mechanical means such as ratchets, ramps or the like in accordance with the direction of movement and/or the position of the levers with respect to each other; (2) in other embodiments, a microprocessor-controlled pressure device controls both a basic overall pressure or minimum pressure and variations in pressure to create variations in resistance to motion in different directions of movement. An overall bias pressure may be established by a tightening mechanism that applies normal pressure between two friction members.

In some embodiments, the friction members are level and flat disks, in others the disks have contoured surfaces to provide different amounts of friction at different locations in the movement of the device. In still other embodiments the friction members are not disks but have other geometric shapes with concentric spherical surfaces. The flexion and extension (or clockwise counter clockwise) friction members may be next to each other in concentric rings, or on opposite sides of each other or one beneath the other or one inside the other.

In one embodiment, the frictional members are made to be easily connected to splints that are parts of existing commercial braces. The frictional members are housed in a control module that has levers extending from it. The levers are replaceably attached to the standard splints of the braces.

With this arrangement, the control module may be attached to a brace by a person wearing the brace, used for exercise while the control module is attached to the brace and removed from the brace after exercise without removing the brace. However, the exercise device need not be fixed to a brace but can be part of an exercise chair as a substitute for other force devices or may be part of a larger exercise unit to provide controlled resistance to movement of several joints in any of several directions.

In still other embodiments, the friction may be provided by compressing frictional plates together in accordance with a planned program, such as magnetically or by rotatable screw drive means or hydraulic plunger means or other means for varying the force between the friction plates. Programs may be mechanical, built into the control module or replaceable within a control module or may be electrical and recorded permanently or changeably or be direct from outside the module.

The basic module can also be used in conjunction with other types of equipment such as ski boots or the like to provide a controlled amount of movement with resistance and thus avoid injury that might otherwise occur such as with an inflexible ski boot. Similarly, such equipment may include sensors to form visual or other sensory images while a person exercises, such as for example, images of terrain while someone is using exercise equipment simulating cross country skiing. Similarly, orthotic systems may be equipped to provide overall or relatively complete exercise environments or other simpler equipment now equipped with weights to provide isotonic exercise may instead be equipped with control modules to provide controlled resistance in accordance with the position of the anatomical segments being exercised. The equipment may be used in conjunction with, or in coordination with or as part of muscle stimulating equipment such as electrical muscle stimulation, and electrical myographic measurement of tonic or phasic muscle contractions for use in feedback systems to time electrical muscle stimulation and/or change the resistance accordingly.

To reduce pain and provide greater use of joints subject to arthrokinetic joint movement dysfunction, a programmed module provides resistance against the movement to the muscles opposing the movement of a weaker muscle. In this specification, "arthrokinetic" dysfunction means that ordinary movement of body portions about a joint result in symptomatic events such as pain and/or inflammation and/or movement in a direction at an angle to the desired movement. The resistance is programmed by the attending physician or physical therapist to provide resistance to the stronger opposing or antagonistic muscles to permit the weaker muscles or agonistic muscles to function normally.

To permit support in movement such as walking by generally weakened persons such as older persons, a programmed module provides resistance to movement in the direction of natural forces. For example, a person who is unable to walk without an aide may have programmed modules placed on the knee joint that would prevent collapse of the knee through resistance that would offset influence of gravity. The amount of selected resistance is dependent on the strength of the muscle at the positions or angles that resistance is applied. Resistance is usually programmed to increase as the patient's knee joints are bent more with or because of the force of gravity.

From the above description, it can be understood that the exercise device of this invention has several advantages, such as: (1) it can provide controlled resistance to movement in either direction; (2) it may be easily snapped onto existing braces to provide a controlled program of therapy without the need for expensive equipment; (3) it can provide a controlled and contoured resistance which depends on the position of the limb; (4) the controlled programs of resistance may be tailored to the individual and controlled by inserts into the exerciser; (5) the resistance is independent of the speed of motion; (6) there is no force applied by the equipment to a user in the absence of an attempt to move and the force is only a force of reaction; and (7) it can function as a component in virtual reality, muscle stimulation, biofeedback equipment and systems for reducing ortho-kinetic joint movement discord.

SUMMARY OF THE DRAWINGS

The above noted and other features of the invention will be better understood from the following detailed description when considered with reference to the accompanying drawings, in which:

FIG. 1 is a fragmentary perspective view of an exercise assembly mounted to the thigh and leg of a person on a brace in accordance with an embodiment of the invention;

FIG. 2 is a perspective view, partly exploded, of the exercise assembly of FIG. 1 mounted to a brace;

FIG. 3 is a fractional, plan view of a control module and fasteners for attacment of the control module to a brace in accordance with an embodiment of the invention;

FIG. 4 is an end view partly-sectioned of the fastener and brace of FIG. 3;

FIG. 5 is an elevational view, partly exploded, of still another embodiment of the invention;

FIG. 7 is a plan view of a portion of the embodiment of FIG. 6;

FIG. 8 is a side view of the portion of the embodiments af FIGS. 5 and 6, shown in the plan view of FIG. 7;

FIG. 9 is a plan view of another portion of the embobidment of FIGS. 5 and 6;

FIG. 10 is a side view of the portion of the embodiment of FIGS. 5 and 6 shown in FIG. 9;

FIG. 11 is a plan view of another portion of the embodiments of FIGS. 5 and 6;

FIG. 12 is a side view of the portion of the embodiments of FIGS. 5 and 6 shown in FIG. 11;

FIG. 13 is a plan view of still another portion of the embodiments of FIGS. 5 and 6;

FIG. 14 is a side view of a portion of the embodiments of FIGS. 5 and 6 shown in FIG. 13;

FIG. 15 is a plan view of still another portion of the embodiments of FIGS. 5 and 6;

FIG. 16 is a side view of a portion of the embodiments of FIGS. 5 and 6 shown in FIG. 15;

FIG. 17 is a fragmentary sectional view of a portion of the embodiment of FIGS. 5 and 6;

FIG. 18 is a partly exploded sectional view of still another embodiment of the invention;

FIG. 20 is a plan view of a program disk used in the embodiment of FIG. 18;

FIG. 21 is a side view of the program disk of FIG. 20;

FIG. 22 is a plan view of a lifter plate that is part of the embodiment of FIG. 18;

FIG. 23 is a side view of the lifter plate of FIG. 22;

FIG. 24 is a plan view of a lifter plate base of that used in the embodiment of FIG. 18;

FIG. 25 is a side view of the lifter plate of FIG. 24;

FIG. 26 is a sectional view of a portion of the plate of FIG. 24;

FIG. 27 is a rear elevational side view of the housing portion of the embodement of FIG. 18;

FIG. 28 is a right elevational side view of a housing of FIG. 27;

FIG. 33 is a sectional view of bolts used in the embodiment of FIG. 18;

FIG. 36 is a fragmentary simplified perspective view of an embodiment of brace which includes an addition to the previous embodiment of FIGS. 1–35;

FIG. 37 is a side view of a portion of the embodiment of FIG. 36;

FIG. 38 is a top view of a portion of the embodiment of FIG. 37;

FIG. 39 is a sectional view through lines 39—39 of FIG. 38;

FIG. 40 is a top view of a portion of the embodiment of FIG. 38;

FIG. 41 is a sectional view through lines 41—41 of FIG. 40.

FIG. 42 is a fragmentary exploded perspective view of still another embodiment of the invention;

FIG. 43 is a perspective view through lines 43—43 of FIG. 42;

FIG. 44 is a block diagram of a control system usable in the embodiment of FIG. 42;

FIG. 45 is a block diagram of a portion of the embodiment of FIG. 44;

FIG. 46 is a side view of another embodiment of lever arm;

FIG. 47 is a partly exploded end view through lines 47—47 of the embodiment of FIG. 46;

FIG. 48 is a side view of another lever that cooperates with the lever of FIG. 46;

FIG. 49 is perspective view of the lever arm of FIG. 48 looking in the direction of lines 49—49 in FIG. 48;

FIG. 60 is a schematic, partly broken away elevational view of a multiple plane exercise device;

FIG. 61 is an elevational sectional view of a housing for a program unit forming a portion of the exercise device of FIG. 60;

FIG. 62 is an end end view of the housing of FIG. 61;

FIG. 63 is an elevational view of a portion of the control module used in the embodiment of exercise device of FIG. 60;

FIG. 64 is an end view of a portion of the housing of the control module of FIG. 63;

FIG. 65 is a simplified end view of a portion of the exercise device of FIG. 60 in an open receiving postion of a limp of an exerciser;

FIG. 67 is a schematic side view of still another embodiment of exercise device;

FIG. 68 is a front elevational view of the embodiment of exercise device of FIG. 67;

FIG. 69 is a simplified sectioned side view of an embodiment of a single plane control module;

FIG. 70 is an end view of the control module of FIG. 69;

FIG. 71 is still another embodiment of exercise device using the control module of FIGS. 69 and 70;

FIG. 72 is a front view of the exercise device of FIG. 71;

FIG. 73 is a top view of a set of exercise devices of the type illustrated in FIGS. 71–72;

FIG. 75 is a simplified, exploded perspective view of a portion of the control module of FIG. 74;

FIG. 76 is a perspective view of another portion of the module of FIG. 74;

FIG. 81 is an elevational view of a portion of the tibia support FIG. 80;

FIG. 82 is an elevational view of another portion of the tibia support of FIG. 80;

FIG. 83 is an elevational view of still another portion of the tibia support of FIG. 80;

FIG. 84 is an elevational view of still another portion of the tibia support of FIG. 80;

FIG. 85 is an elevational view of still another portion of the tibia support of FIG. 80;

FIG. 86 is an elevational view of still another portion of the tibia support of FIG. 80;

FIG. 87 is a plan view of still another portion of the tibia support of FIG. 80;

FIG. 90 is a flow diagram useful in practicing the invention;

DETAILED DESCRIPTION

Figure 6:
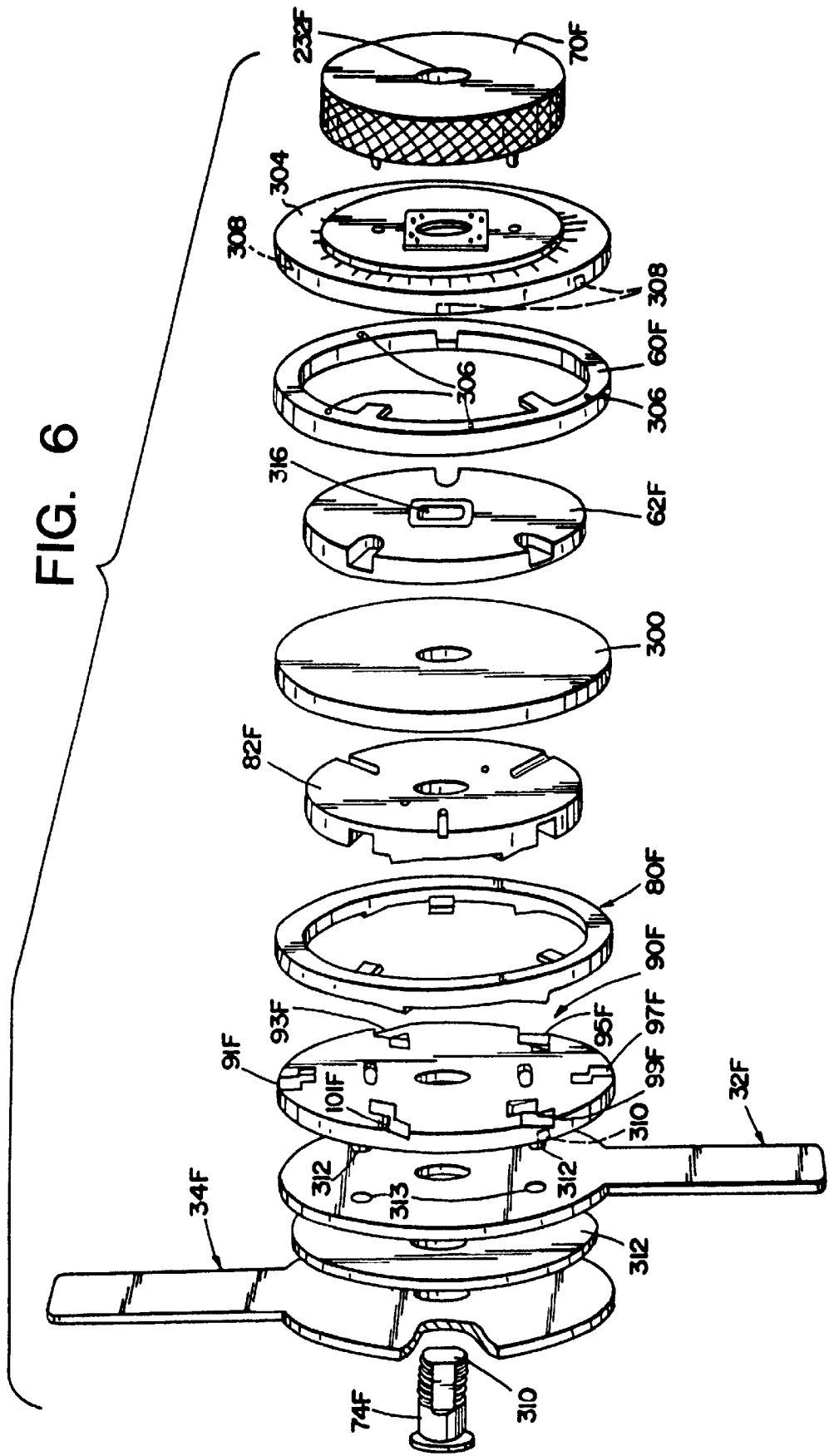
FIG. 6 is an exploded perspective view of the embodiment of FIG. 5, partly broken away and sectioned.

In FIG. 1, there is shown a fragmentary, perspective, partly-exploded view of an exercise assembly 10 mounted to a limb 12. The exercise assembly 10 includes a limb brace portion 14 and first and second exercise modules 16A and 16B, one on each side of the limb brace portion 14 (only 16A being shown in FIG. 1). In the preferred embodiment, the limb brace 14 is a standard brace that is not a part of the invention by itself except insofar as it cooperates with one or more removable exercise modules such as the exercise modules 16A and 16B.

The removable exercise modules 16A and 16B mount to the limb brace portion 14 which in this embodiment is a leg and thigh brace to control the resistance needed by limb 12 to move the brace portion 14 for limited movement about a knee. In the preferred embodiment, the resistance to movement is provided by frictional resistance.

The limb brace 14 includes a first support means 20, a second support means 22 and two pivotal joints 24A and 24B (Only 24A is shown in FIG. 1), with the first support means being fastened to the thigh and the second support means being fastened to the leg of a person. Each of two sides (splints) of the first support means is connected to a corresponding one of the two sides of the second support means by a different one of the two pivotal joints 24A and 24B so as to be capable of limited movement under the control of the knee muscles.

The exercise module 16A includes a control assembly 30A, a first lever assembly 32A and a second lever assembly 34A. The first and second lever assemblies 32A and 34A are fastened to the control assembly 30A on opposite sides thereof with the first lever assembly 32A being adapted to be fastened to the first support means 20 to move with the thigh of the person and the second lever assembly being adapted to be fastened to the second support means 22 to move with the leg of the person. Because the exercise modules 16A and 16B are essentially identical and the lever assemblies 32A and 34A are essentially identical, only the exercise module 16A and only the assembly 34A will be described herein.

The assembly 34A includes a first affixed member 33A, a second snap-on member 35A, a first fastener 37A and a second fastener 39A. The affixed member 33A is permanently attached to a portion of the control module 30A and has an open portion adapted to receive a splint member of the lower support means 22 within a groove therein and the second snap-on portion 35A fits over the opposite side of the splint member with the fasteners 37A and 39A passing through both member 33A and 35A to hold them together.

With this arrangement, the affixed members of the first and second lever assemblies may slide over corresponding portions of different ones of the support means 20 and 22 with the control module 30A overlying the joint 24A. The snap-on portion such as 35A and its corresponding part on the lever at 32A may then be slipped over the opposite side and fastened by fasteners such as 37A and 39A to the affixed member 33A to hold the lever arms with corresponding portions of the support members 20 and 22. The fasteners 37A and 39A may be bolts, screws, snap-on pins or any other suitable fastener.

The control assembly 30A includes force resistance members, such as for example friction disks, not shown in FIG. 1, and a calibration dial 41 in the embodiment of FIG. 1 which is setable to different amounts of resistance. The lever assemblies 32A and 34A are fastened to different moving parts of the control assembly 30A and are movable with respect to each other only with the programmed amount of force so that the exercise module 16A can control the force against which the knee is articulated by the patient.

With this arrangement, the control assembly 30A controls the movement of the first and second lever assemblies which in turn control the amount of force required for the knee muscles of a person to move the leg with respect to the thigh. The two control modules 16A and 16B can be easily snapped into place on the brace and the patient is able to exercise by following a convenient schedule. The amount of resistance in the control module can be set by the attending doctor into the control module in a manner to be described hereinafter.

In FIG. 2, there is shown a perspective view of the exercise assembly 10 with the limb brace portion and removable exercise modules 16A and 16B exploded away to show a right leg brace having first and second pivotal joints 24A and 24B substantially parallel to each other and adapted to be positioned on opposite sides of a knee, each of which cooperates with a corresponding one of the exercise modules 16A and 16B. The pivot joints 24A and 24B each connect a different one of two parallel thigh splint members 26A and 26B to a corresponding pair of leg splint members 28A and 28B.

On the outside pivot point 24A, the control module 30A overlies the joint, the first lever assembly 32A is fastened for movement with the thigh splint member 26A and the second lever assembly 34A is snapped onto the leg splint member 28A. The splint members are connected together by a soft framework and straps that are buckled tightly about the leg so that the splint members move respectively with the thigh and the leg bones. The pivot points include a positionable perforated plate 27A (not shown in FIG. 2 that can be positioned with respect to a base having pins such as 29A (not being shown in FIG. 2) located in it to set the maximum range of movement of the brace both in extension and flexion.

The brace itself is intended in normal use to control movement of the thigh to protect the anterior cruciate ligament against excessive rotation or extention. Periodically, the exercise assembly may be snapped in place and the muscle therapeutically exercised in accordance with a controlled program. The program is established by the physician or physical therapist, but the exercise program may be performed easily by the patient several times a day in accordance with a prescribed plan. The amount of friction may be adjusted to differ with extension and flexion of the leg and a force profile may be programmed into the device in some embodiments to conform to the desired required force for exercise. The program and friction, of course are set to be the same in the two exercise modules 16A and 16B.

As shown in FIG. 2, the affixed member, such as 33A, of the lever 34A has a large opening to receive the splint members of many different models of knee brace loosely. To provide a tight fit, the snap-on members 35A are made of different sizes and fit internally to the upper and lower portions of the affixed members, thus enabling a plastic support member to fill in the loose space and enable a standard exercise module to be used with a number of different braces.

In use, the control module 30A may be set to provide a programmed amount of resistance between the two lever arms 32A and 34A to provide a programmed amount of resistive force to movement during exercising. To select the programmed resistance, the control module 30A includes a direction-sensitive resistance-mode selector means which selects one resistance program when the first and second levers are moved together such as by the bending of the knee and another resistance program when the leg is extended causing the levers to move in the other direction. In the preferred embodiment, a direction-sensitive resistance-mode selector selects one resistive friction program when the levers move in one direction and a different resistive friction program when the levers move in the opposite direction.

In some embodiments, the two exercise modules 16A and 16B are each fastened to the brace and not to each other. The force on the opposite sides of the brace are equalized by the belts on the brace itself. However in other embodiments, the two modules may be connected by a rigid member or the brace may include a rigid member to connect the two sides together to prevent unequal force on the two sides of the limb that may cause harmful torsion and provide a tibia support belt described hereinafter. Such a rigid member is arranged to snap into openings on the lever assembly 34A and 34B. Multiple connectors may be used is needed and connection may be made to the lever arms 32A and 32B or to the brace itself.

In FIG. 3, there is shown the module 30 connected to one embodiment of clamping members 32 and 34 and having a dial 31 for adjusting the force resisting motion movably affixed to the center nut 74C (not shown in FIG. 3) so that the nuts may be tightened to establish a zero point and the dial pointer 33 set to an indicia mark for zeroing. After these settings, motion of the nut to provide less pressure provides an indication on grade marks 33 with respect to the pointer of the amount of pressure or resistance that is to be applied.

In this embodiment, the clamping means 32A and 34A are identical and consist of four apertures in each of the members 32A and 34A aligned with four corresponding apertures in the braces. In FIG. 8, four of these apertures are 180–186 are shown closed by fasteners so as to fasten the clamping members 32 and 34 to the brace members and four are shown without such fasteners, but in actual use would also include fasteners such as the combinations of a bolt and nut.

In FIG. 4, there is shown a sectional view of a portion of a brace 22 and an end of the clamping member 32A with aligned openings 188 and 190 that receive fasteners to hold the portion of the brace 22 and clamping member 32A together. The fasteners to hold the brace and clamping member together may be bolts and nuts, machine screws, spring biased plungers or any other type of device able to provide a quicker connection. As best shown in FIG. 4, the clamping members have a open portion in the bottom to fit conformingly around a portion of the brace.

In FIG. 5, there is shown another embodiment of control module 30F having as its principal parts an adjustment nut 70F, program disks 62F and 60F, inner and outer lifter plates 80F and 82F, a ramp 90F and inner and outer lever assemblies 32F and 34F respectively. These are positioned in the order named about the shaft or bolt 74F in a manner similar to that described in the previous embodiments. A urethane disk 300 is positioned between the recorders and the lifter plates and a leather disk 302 separates the outer and inner lever assemblies 32F and 34F.

As better shown in FIG. 6, the adjustment nut 70F is threaded onto the shaft or bolt 74F to exert pressure on the other elements as a major adjustment. A annular disk 304 is rotatable about and concentric with the adjustment nut 70F, with both the adjustment nut and the dial 304 having indicia on their top surface.

With this arrangement, the nut 70F may be tightened to its maximum extent and the dial 304 lifted to disengage downwardly extending posts 308 equally spaced circumferentially along the periphery of the dial 304 from a corresponding number of equally spaced circumferential apertures 306 in the outer recorder 60F. While it is lifted, zero indicators can be aligned and then, with the dial still engaging the recorder, the nut can be loosened to a predeterimined adjustment force from the zero position. The markers between the dial and the nut now indicate the looseness of the adjustment nut and thus the fixed amount of pressure between the program fricion disks and the recorders.

To provide programmed resistance to movement, the shaft or bolt 74F is fastened for rotation with the inner lever assembly 34F and includes a cut-away portion forming a partly flattened member with an elliptical cross section 310 at its uppermost end. The apertures in the inner recorder disk and the polyurethane disk 300 are elliptical and engage the corresponding elliptical section at the top of the shaft 74F formed by removing a section of the cylindrical shaft and thus move with the shaft and with the inner lever. The inner and outer recorders have upon them different tapered surfaces to provide a different thickness and are otherwise free to move up and down on the shaft to prevent different amounts of friction to surfaces which rotate against each other and underlie these tapered sections.

To provide frictional movement either between the outer recorder 60F or the inner recorder 62F which are locked together by fingers, the inner lever assembly 32F (FIG. 5) is mounted for rotation with the ramp member 90F since it receives downwardly extending posts 310 in its openings 312 and moves with respect to the inner lever assembly 34F (FIG. 6) because it is separated therefrom by a disk 312 in a manner similar to the prior embodiments. The handle ramp 90F includes a plurality of circumferentially spaced ramp members 91F, 93F, 95F, 97F, 99F, and 101F positioned to engage the inner and outer lifter plates 80F and 82F. These lifter plates have ramps on their bottom surfaces which selectively engage the ramp 90F to either raise the inner or the outer lifter plate depending on the direction of the matching surfaces between the bottom of the lifter plate 80F and the ramp plate 90F.

When the outer plate 80F is lifted in one direction, the polyurethane disk 300 is pressed between it and the outer recorder 60F to create friction as the lifter plate rotates with the outer assembly 32F. Similary, if the inner lifter plate is lifted, it presses on the urethane disk 312 further in and opposite to the inner program 62F so that as the assemblies 32F and 34F move with respect to each other carrying their respective ones of the lifter plate 80F and the inner recorder 62F.

Thus, either the outer lifter plate 80F or the inner lifter plate 82F is engaged by the ramps on the ramp plate 90F to move it while the other one does not move with respect to the polyurethane disk 300 and the respective one of the inner and outer program disk 60F and 62F which move with the lower handle 32F, being so constrained by the elliptical cross section 310 at the top of the shaft or bolt 74F.

In FIG. 7, there is shown a plan view of the inner program disk or recorder 62F showing the generally elliptical section 316 which is engaged at all times with the elliptical portion 310 (FIG. 6) of the shaft or bolt 74F (FIG. 6). Inwardly extending openings 318 serve to engage for movement the outer program disk or recorder 60F (FIG. 6) in a manner to be described hereinafter.

As best shown in FIG. 8, the inner program disk or recorder 62F includes raised portions and lowered portions such as those shown at 320F which is raised and 322F which is lowered so that, as it rotates with respect to the inner lifter plate 82F (not shown in FIG. 8), the frictional force is varied so as to provide a controllable program which typically starts lower, increases to a peak and then is reduced. This program is easily changeable and can be prepared at the option of the physical therapist for the appropriate exercise variation during extension of the limb.

In FIG. 9, there is shown a plan view of the outer program ring 60F having an annular ring like section with inwardly extending members 324 adapted to engage the radially extending notches 318 (FIG. 7) in the inner program disk 62F (FIG. 7). With this arrangement, the outer program disk also rotates with the inner lever assembly 34F (FIG. 6) since it rotates with the inner program disk which rotates with the top of the shaft or bolt 74F.

As best shown in FIG. 10, the outer program disk or recorder 60F also includes a contour surface having raised portions such as that shown at 328 and lower portions such as shown at 330, which may differ as in the inner program disk by a few hundreths of an inch so as to vary pressure when the outer program disk is selected during flexion of a limb. The lifter plates, ramps and inner and outer programs may be reversed so that an inner program disk controls flexion and the outer program controls extension. Similarly, the programs need not be recorded on the upper surface but could be on the lower surface and could be on a conical surface that is moved upwardly or downwardly to engage cooperating members.

In FIG. 11, there is shown a plan view of an outer lifter plate 80F which also has inwardly extending members that can be lifted free of the inner lifter plate in a manner to be described hereinafter. As best shown in the elevational view of FIG. 12, the lifter plate includes ramps such as ramps 352, 354, and 356 on its upper surface adapted to engage the ramp plate 90F (FIG. 15). On the bottom surface of the lifter plate, there are a plurality of raised nodes 360 adapted to engage the urethane disk 300. When the ramp plate 90F is rotated in one of clockwise or counterclockwise direction, which in the preferrred embodiment is flexion, the outer lifter plate rides upwardly to permit movement of the ramp plate 90F with respect to it. Thus, with one direction of motion, friction and pressure is exerted on the urethane layer 300 and in the other it is not.

In FIG. 13, there is shown a plan view of the inner lifter plate 82F having an inner circular aperture 358 adapted to receive the shaft or bolt 74F and rotate with respect to it and on its outer surface having openings 360, 362 and 364 adapted to engage the inwardly extending members 350, 352 and 356 so as to rotate the outer member unless the outer member has been lifted free from it.

As best shown in FIG. 14, the inner lifter plate includes a plurality of ramps 370, 372 and 374 extending upwardly to engage the handle ramp 90F and a plurality of nodes 380, 382 and 384 extending downwardly to engage the urethane disk 300. The nodes, during motion of the inner ring, exert pressure on the urethane layer 300 selectively to cause a predetermined pressure. In the embodiment, of FIGS. 5–14, a single-plane bi-directional variable range of motion pre-programmed velocity-independent resistance is provided.

In FIG. 15, there is shown a plan view of the ramp disk 90F having a central opening 370 to receive the shaft 74F (FIG. 6) and a plurality of circumferentially spaced ramps 91F, 93F, 95F, 97F, 99F and 101F in an inner circle and a plurality of ramps 103F, 105F, 107F, 109F, 111F and 113F in an outer circle, with the ramps on an inner circle facing in the opposite direction as the ramps on the outer circle so that the ramps on the outer circle lift the outer lift plate 80F and the ramps on the inner circle engage with ramps on the inner plate 82F. As best shown in FIG. 16, the handle ramp 90F is mounted to the outer handle 32F by a plurality of posts 370 and 372 being shown in FIG. 16. These posts engage similar openings circumferentially spaced in the outer handle assembly 32F so that the outer handle assembly and the ramp disk 90F move together.

With this arrangement, rotation of the handle and the ramp disk 90F together in one direction will cause the ramps 97F to engage the inner lifter plate 82F and thus drive both the inner and the outer plate since they are interlocked together. However, it does not lift the inner plate but does lift the outer lifter plate since the outer lifter plate rides upwardly on the outer ramps at the same time that the inner ramps are engaging drivingly.

In FIG. 17, there is shown in a sectional view of FIG. 15: (1) the positioning of the ramp 97F in the inner ring of ramps and the ramp 109F in the outer ring of ramps; (2) the different slopes such as that shown at 376F in the outer ring of ramps and 378F in the inner ring of ramps and (3) the flattened portion at the top of each ramp. With this structure, the lifter plate rides up the ramp and then stops in a stable position, being held by the other of the inner or outer lifter plates with its ramps in that stable flattened portion for driving in the lower position.

In FIG. 18, there is shown a partly exploded sectional view of another embodiment of control module 30G similar to the emobodiment of FIGS. 5–17 having as its principal parts the inner and outer lever assemblies 32G and 34G, two interfitting centrally located bolts or shaft 44G and 47G, a lever separating disk 45G, first and second adjustment nuts 70G and 71G, first and second program disks 60G and 62G, first and second reader plates 63G and 65G and first and second lifter plate and base. The first cam includes a lifter base 82G, a lift plate 610G and the second cam includes a lifter base 81G and a lift plate 612G.

To hold and control the motion of the cams and cam followers together, the bolts 44G and 47G and corresponding housings 620G and 621G cooperate. The outer lever assembly 34G has four holes 623G (not shown in FIG. 28) formed in its bottom to fit with posts from the inner housing 620G. Base friction between the rotating elements is established by the adjustment nuts 71G and 70G at least one of which is threadable upon the bolt 44G and 47G. The program disks 60G and 62G rotate with the bolts 44G and 47G, lever assembly 32G, the cam lifter 82G and 81G, and the lifter plates 610G and 612G. The reader plates 608G and 609G rotate with housings 620G and 624G and the outer lever assembly 34G. This causes friction on the friction disks 313 and 310 when the lift plates are engaged and lever assemblies are moving with respect to each other.

With this arrangement, the program disks or friction disks are positioned one under the other together with the lifter base (cam) and lifter plates (cam follower members) which engage to read programs upon them. When the levers move in one direction, one set such as the lower set of lifter plates are engaged and when moving in the other direction the other of the lifter plates are engaged. The program disks are conveniently mounted inside the housing to permit easy insertion. The disks 312G and 310 (FIG. 6) may be polyurethane members or another such material that will permit controlled friction.

In the embodiment of FIG. 8, the housing is in two parts, being split at its center location so as to include two portions: (1) the housing coupler 622; and (2) the outer housing 624 which thread together as shown in FIG. 28 or which may be snapped together.

The bolts 44G and 47G are adapted to fit one into the other near the center of the control module. The two adjustment nuts 71G and 70G are located on the outer surface where the housing is opened. When the two parts of the module are separated, the adjustment nuts can be individually adjusted to establish friction on each housing half and the program disks 60G and 62G and nuts can be easily changed. Moreover, if force in only a single direction is desired, the top portion may be omitted.

In this embodiment, the two parts of the module are the inverse of each other in the order of its parts so that one of the two sets of lifter base, lifter plates, program disks and adjustment nuts is the inverse of the other. This simplifies manufacturing but more significantly permits quick access by separating the two housings with a catch or screw threads to the adjustment nut for ready calibration and for easy insertion of different program disks. For easy insertion of program disks, the program disks are located next to the adjustment nut in each of the two parts and each of the parts of the module control the resistance to movement in a different one of the flexion and extension directions.

Figure 19:
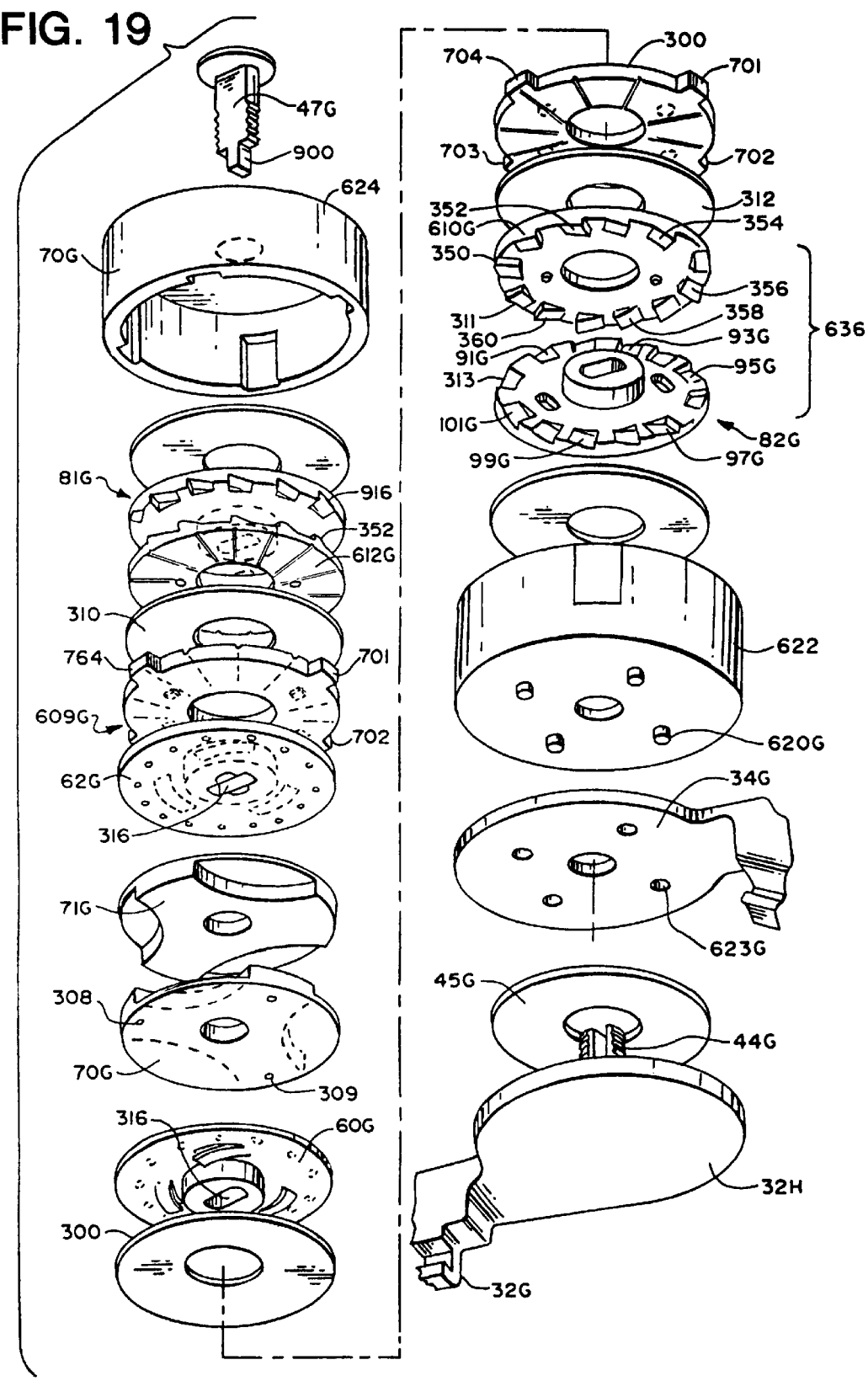
FIG. 19 is an exploded perspective view of the embodiment of FIG. 18.

As better shown in FIG. 19 which is a bottom exploded perspective view except for lift plate 82G shown in a top view, the adjustment nut 70G is threaded onto the shaft or bolt 44G, and the adjustment nut 71G is threaded onto the shaft or bolt 47G of the upper and lower sections respectively to exert pressure on the other elements as major calibration adjustments. The shaft or bolt 44G includes a female slot that receives a male parallelopiped portion that causes the two bolts to engage and rotate together. The nuts permit individual calibration of the two sections and contain indicia cooperating with indicia on the housing or other members, such as the program disks 62G and 60G.

The disks 62G and 60G include apertures that receive a part on the nuts 71G and 70G respectively to lock them in position, and the disks 62G and 60G include elongated slots that receive similar shaped portions of the bolts 47G and 44G respectively to cause the disks 62G and 60G to rotate with their respective bolts. Both of the adjustment nuts 70G and 71G and the dials have indicia on their top surface to indicate their positions.

With this arrangement, the nuts 70G and 71G may be tightened to its maximum extent and then backed off to disengage corresponding downwardly extending detents 308 and 309 into equally-spaced circumferentially positioned holes along the periphery of the recorder disks. In the alternative the equally-spaced circumferential apertures may be in a corresponding dial 304 shown at 308 embodiment of FIGS. 6–15 that is freely rotatable and settable by inserting a part from the nut into it rather than in a corresponding recorder or program disks 62G and 60G. While such a dial 304 (FIG. 6) is lifted, zero indicators can be aligned and then, with the dial still engaging the recorder, the nut can be loosened to a predetermined adjustment force from the zero position. The indicia between the dials and the nuts now indicate the looseness of the adjustment nuts and thus the fixed amount of pressure between the friction disks and the recorders or program disks.

To provide programmed resistance to movement, the shafts or bolts 44G and/or 47G are fastened for rotation with the inner lever assembly 32G respectively and includes at their upper ends a cutaway portion having flat sides to form a generally elliptical cross section. The apertures in the program disks 60G and 62G and the lifter base 82G and 81G have a generally elliptical side with flat sides and rest on the generally elliptical portions (flat sided portions) at the top of the corresponding shafts 47G and 44G to move with the shafts and with the inner levers. The inner and outer recorders or program disks 62G and 60G have upon them different tapered surfaces to provide a different thickness and are otherwise free to move up and down on the elliptical section to prevent different amounts of friction to surfaces which rotate against each other and underlie these tapered sections.

The lifter plates 610G and 612G each include a different plurality of circumferentially spaced ramp members (350, 352, 354, 356, 358 and 360 being shown on plate 610G) positioned to engage the ramps (91G–101G being shown on lifter base 82G) on lifter base 81G and 82G (lifter base 82G being shown from a top perspective view). The lifter plates have parts 311 that enter the openings 313 in the lifter base. These posts limit rotation of lifter plates with respect to the lifter base to keep the ramps engaged. As this rotation occurs, the lifter plates may be raised by ramps 350–360 traveling along ramps 91G–101G.

When the outer lifter plate 612G is lifted in one direction, the polyurethane disk 310 is pressed between it and the outer reader 609G to create friction as the lifter plate rotates with the lever outer assembly 32G and the reader rotates with the lever assembly 34G. Similarly, if the inner lifter plate 610G is lifted, it presses on the urethane disk 312 opposite to the inner reader 608G so that as the assemblies 32G and 34G move with respect to the friction urethane disk. Thus, either the outer lifter plate 612G or the inner lifter plate 610G is engaged by the ramps on a lifter base to move it while the other one does not move with respect to the respective one of the polyurethane disks 300 and 312. The respective one of the inner and outer program disk 60G and 62G move with the lower handle 32G.

In FIG. 20, there is shown a plan view of the program disk or recorder 60G or 62G showing the generally flat-sided elliptical section 316 which is engaged at all times with the complementary generally elliptical portion of the corresponding shaft or bolt 44G or 47G (not shown in FIG. 20).

As best shown in FIG. 21, the inner program disks or recorders 62G includes two rows of raised ramp portions and lowered portions such as those shown at 320G which is raised so that, as it rotates with respect to the lifter plates 82G and 81G (not shown in FIG. 21), the frictional force is varied to provide a controllable program that typically would start out lower, increase to a peak, and then be reduced. This program is easily changeable and can be prepared at the option of the physical therapist for the appropriate exercise variation during extension of the limb. Three leaf springs to maintain tension are formed in each program disk as shown for example at 321G.

In FIG. 22, there is shown a plan view of an outer lifter plate 81G of FIG. 19 which also has inwardly extending members that can be separated and become free of the lifter base 81G (FIGS. 24 and 25) in a manner to be described hereinafter. As best shown in the elevational view of FIG. 23, the lifter plate (612G or 610) includes ramps such as ramps 352, 353, 354, 355 and 356 on its upper surface adapted to engage corresponding ramps on the lifter base 81G (FIG. 24).

When the ramp plate is rotated in one of clockwise or counterclockwise direction, which in the preferred embodiment is flexion, the lifter plate 612G is lowered or moved in the direction of the ramp plate 81G, and when rotated in the other direction, the lifter plate 612G rides upwardly to permit movement over the lifter base 81G with respect to it causing the reader plate 609G to exert pressure on polyurethane disk 310 (FIG. 19). Thus, with one direction of motion, friction and pressure is exerted on the urethane layer 310 and in the other it is not. In the other section, the ramps are reversed on lifter disk 610G so as to cut in a similar manner with reversed direction of rotation.

In FIG. 24, there is shown a plan view and in FIG. 25, there is shown an elevational view of the lifter base 81G having a central opening 370 to receive the shaft 74G (FIG. 6) and a plurality of circumferentially spaced ramps 91F, 93F, 95F, 97F, 99F, 101F, 103F, 105F, 107F, 109F, 111F and 113F (FIG. 24). With this arrangement, rotation of the base ramp disk 81G together in one direction causes the ramps 91F–113F to engage the inner lifter plate 612G (FIG. 19) and thus drive the lifter plate up into urethane disk 312.

In FIG. 26, there is shown in a sectional view through lines 36—36 of FIG. 24: (1) the positioning of the ramps; (2) the different slopes such as that shown at 104C; and (3) the flattened portion 376 at the bottom of each ramp. With this structure, the lifter plate rides up the ramp and then stops in a stable portion, being held by the other of the inner outer ring of ramps in that stable flattened portion for driving in either an elevated position or a lower position.

Figure 29:
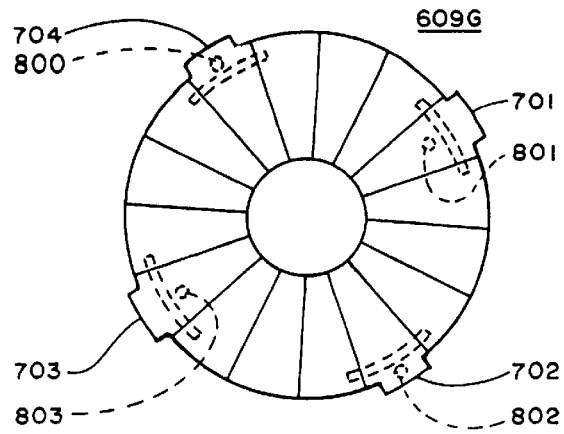
FIG. 29 is a plan view of the roller reader plate of the embodiment of FIG. 18.
Figure 30:
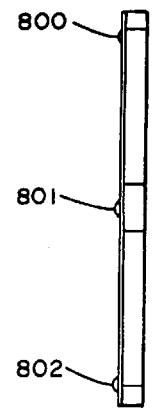
FIG. 30 is a side view of the plate of FIG. 28.

In FIGS. 27 and 28, there are shown a rear elevational side view and a right elevational side view of the upper housing member 624 (FIG. 19) adapted to receive bolt 47G (FIG. 18) in a central aperture and having: (1) internal notches to receive projections 701–704 from reader plate 609G (FIG. 30); and (2) notches 70G adapted to match external detents 708 on housing 622 (FIG. 29). As shown in FIGS. 29 and 30, the reader plates 609G and 608G each include four different ears 701–704 that engage internal notches 701–704 in housing 624 to be held against rotation thereby. Rollers 800, 801, 802 and 803 ride against the outer track and inner track program contour 320G and 321G (FIGS. 20 and 21), thus forcing the back of the roller plate to press the polyurethane disks 310 and 312 against the lifter plate 610 and 612 for programmed motion as the lifter base plates 81G and 80G are moved. The inner and outer tracks 320G and 321G (FIGS. 20 and 21) face the rotters 800–803, two of which (800 and 802) are aligned with the outer track 320G and two (801 and 803) with the inner track 323G. The two plastic disks 300 one of which shown broken away from program disk 60G (FIG. 6) and the other disk 62G covers the four rollers and includes slots to permit isolation of tension in the plastic disk adjacent to the rollers. The two rollers and two tracks are for different directions of movement such as flexion and tension.

Figure 31:
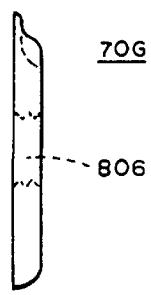
FIG. 31 is a side view of an adjustment nut used in the embodiment of FIG. 18.
Figure 32:
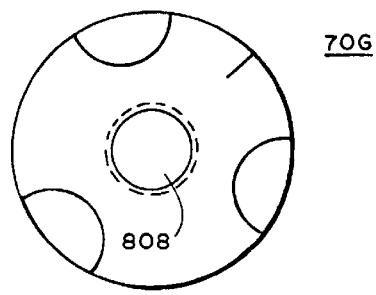
FIG. 32 is a plan view of an adjustment nut of FIG. 31.
Figure 34:
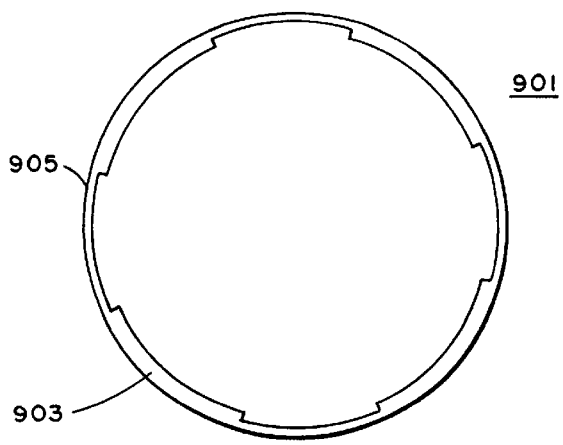
FIG. 34 is a rear elevational side view of a housing that is used in the embodiment of FIG. 18.
Figure 35:
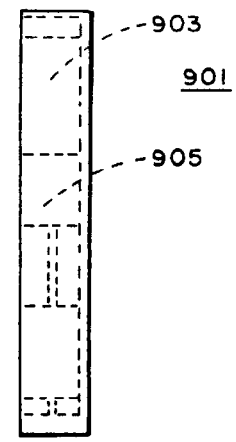
FIG. 35 is a right elevational side view of the housing of FIG. 34.

In FIGS. 31 and 32, a side elevational view and plan view of one of the flat tension adjustment nuts 70G and 71G are shown having corresponding internal threaded openings 806 and 808. These nuts have matching and engaging complementary slots and wedges on their ends 47G and 44G (FIG. 18). As best shown in FIG. 33, the bolts 47G and 44G have interfitting parts 900 and 902 that engage to lock the bolts together while permitting to pull apart to separate the top and bottom sections of the control module. The matching covers 901 are shown in the plan view of the drawing and sectional view in FIGS. 34 and 35 respectively. External threads permit control of friction by receiving individual adjustment nuts. Separate covers, FIGS. 23 and 35, may close the two sections if only one side is to be used. The cover 901 has downwardly extending detents 903 separated by notches 905 that match the corresponding parts of the bottom sections of FIGS. 27 and 28.

In FIG. 36, there is shown a fragmentary perspective view of a brace in accordance with the invention having a two side support 904, which may for example be a tibia support, locking the right and left sides of a brace together. For this purpose, the two-side support 904 includes a rigid interlocking brace section 906 and a cushion section 908. The section 906 keeps the right and left sides 912A and 912B in position with respect to each other and the cushion section 908 keeps the tibia or other body part in position. The rigid portion 906 has an adjustable lock 910 in the center and corresponding fasteners for sides 912A and 912B for locking to the leg braces. The cushion portion is adjustable to be pulled tightly against the leg.

As best shown in FIG. 37, the locking section 910 includes a pin 914 that fits in any of a series of holes 916 in side 918 of the support. The selection of aligned holes 916 to receive pin 914 determines the length of the top portion of the rigid brace section 906 (FIG. 36). The cushion has a different end extending through a different one of the openings 922 and 924 and extending over the top of the brace for fastening, such as by velcro at 926 and 928 respectively. As best shown in FIGS. 38–41, the sides 918 and 920 include: (1) interfitting top portions containing openings so as to conveniently slide together; and (2) a portion of the velcro hook-and-loop fastener for the cushion 908 (FIG. 37). The embodiments of FIGS. 15–41 provide a single-plane, bi-directional, variable range-of-motion and a preprogrammed velocity-independent resistance. The means for fastening the brace to a leg are not shown in FIG. 36 but may include pads and a means for adjusting the location of the pads to avoid irritation or damage to the body such as irritation of burns.

To reduce pain and provide greater use of joints subject to arthrokinetic joint movement dysfunction, a programmed module provides resistance against the movement of the muscles opposing the movement of a weaker muscle. In this specification, the word, "arthrokinetic" dysfunction means that ordinary movement of body portions about a joint result in symptomatic events such as pain and/or inflammation and/or movement in a direction at an angle to the desired movement. In using this invention, the resistance is programmed by the attending physician or physical therapist to provide resistance to the stronger opposing or antagonistic muscles to permit the weaker muscles or agonistic muscles to function normally.

Some causes of arthrokinetic dysfunction are poor tracking or alignment of movement because of weak or tight muscles, compression forces of joints during movement or adhesive restriction of movement. For example, patello-femoral pain may be caused by: (1) poor tracking due to weak vastus medialis obliquus (VMO), tight hamstrings or tight illiotibial band; (2) compression of joints due to chondromalacia of the patella, patella alta/baja, narrow femoral/trochlear groove or genu varum/valgum; or (3) adhesive restriction due to poor patellar mobility.

Figure 55:
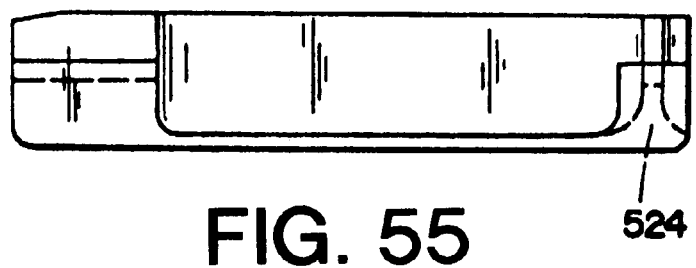
FIG. 55 is a side view of the portion of handle clamp of FIG. 54 taken through lines 55—55.

Facilitation of medial and lateral knee stability, co-contraction of anterior and posterior musculature, and reduction of patello-femoral compression can all be enhanced through application of a hamstring resistance program using the module of embodiments of FIGS. 1–55. There are three distinct flexion programs that will provide safe, stabilizing resistance to build strength. Depending on the patient's condition, different programs may be selected to compliment the needs of the patient and maximize abilities.

The HFP (constant resistance or flat plane program) can be used with patients who will be performing moderate activity levels such as: (1) exercising at a moderate level on the stairmaster, stationary cycle, or leg press; and (2) walking less than 2 mph, climbing and descending stairs, partial squats, knee flexing while sitting, and step downs. By performing these exercises while using the HFP, knee strength, patellar tracking, and patellar mobility are safely increased or improved without compressive irritation and inflammation.

The HIP (increasing resistance) can be used with patients who will be performing minimal activity because of weakness or high pain levels. This program selection is ideal for the tentative, cautious, distrusting, or chronic patients. Normal stride length and cadence will be difficult with ambulation, so speed of activity needs to remain slow. Completion of desired range of knee flexion is a must, therefore the patient must "deliberatly complete" each repetition.

For example, to permit support in movement such as walking by generally weakened persons such as older persons, a programmed module provides resistance to movement in the direction of natural forces. For example, a person who is unable to walk without an aide may have programmed modules placed on the knee joint that would prevent collapse of the knee through resistance that would offset influence of gravity. The amount of resistance selected is dependent on the strength of the muscle at the positions or angles that resistance is applied. Resistance is usally programmed to increase as the patient's knee joints are bent more with or because of the force of gravity.

The HDP (lowering resistance program) can be used with patients who wish to perform kinetic activities at a higher level of resistance and speed. This is an ideal way to normalize closed kinetic chain activity provided strength is not a major issue at the vastus medialis obliquus (VMO). Quick facilitation of hamstrings activity decreases the pull of the vastus lateralis through reciprocal inhibition at the early stage of knee flexion or eccentric activity, therefore allowing for symmetrical patellar balance and allignment upon the first degrees of knee flexion.

Some embodiments of the invention described above can apply resistance through two separate, range-of-motion programs that vary the preset overall resistance independently in both directions (flexion and extension). This means that the user can benefit from preset patterns of resistance when participating in closed kinetic chain activity while wearing the exercise device. For example, during a closed kinetic chain activity wearing this system, a patient is able to feel appropriate resistance at knee extension during "swing" phase of gate and appropriate resistance at knee flexion during "step through" or "push off" phases of gate across the same knee. Also, a program patterned resistance can be applied across the joint, in a safe, protected and proper manner, at the patient's home, and not the clinic. In addition, by applying resistance through a bracing system that varies in both directions, the user can now enhance or decrease eccentric contractions in weight bearing situations.

Changing the programs is easy because of their location within the system. This means more convenience for the person changing the program, and less chance of an assembly error after changing programs, which could cause malfunction of the device during usage.

The system protrudes out less from the brace, thus allowing the patient to use the brace during everyday walking, versus just attaching the device for exercise only. This helps the patient during early ambulation, by using an incline program to ease the patient into the range of motion stops set on the brace.

The use of a ramp engagement system, instead of a one way clutch or ratchet mechanism, permits programming of resistance to vary through the range of motion in one direction, while eliminating all resistance in the other direction. This allows the clinician to isolate the greatest deficits of strength within the patient's range of motion, and then apply appropriate consistant resistance to the isolated ranges of weakness in a 'safe' manner, and within the patients own home. This also allows the patient to more quickly adapt to resistance forces that are applied at weaker degrees of the range of motion. In addition, now because of the capability of being able to apply a varied range of motion of resistance across joints through bracing, the clinician can now provide a range of motion program specific to the user, that eliminates inconsistant force against movement.

Unlike isotonic resistance systems, some embodiments of this invention produce resitance that is immediately eliminated as movement stops, creating a safer exercising system; and although isokinetic systems provide this same safeguard because they are accommodating resistance machines that use a variable torque motor or hydraulic/air pressure, the velocity of movement affects the amount of resistance applied to the user, unlike this embodiment in which velocity of movement has no effect on the preset resistance. To the patient, this means he or she does not have to accommodate pain or weakness by slowing down a prescribed workout, since slowing down velocity of movement to reduce resistance to the weakest parts of the range of motion may actually decrease efficacy of the program specifically designed to strengthen these weakest parts.

Moreover, resistance produced by this invention can be isolated to one direction at a time. In the clinical setting, this now allows a patient recovering from a knee ligament injury to exercise earlier, because he can now exercise safely and properly during flexion movements only, (which may be safe 2–3 weeks after surgery) and not extension movements (which may not be safe until 6 weeks after surgery).

Another advantage of this invention is it's relative small size. With the addition of a fastening attachment, this allows the first opportunity for the clinician to apply resistance across a joint through conventional bracing. This allows the clinician to educate and facilitate the patient on safe patterns of appropriate resistance in their own home, and outside of the medical community. Applying resistance in this manner also provides development of neuromuscular coordination and the antagonistic and assistance muscles, this is because it is applied to the patient in a closed kinetic chain activity (resistance device is attached to the patient) versus an open kinetic chain activity (resistance device is attached to the floor).

In FIG. 42, there is shown a perspective view of another control module 30H having a shaft or bolt 74H, an inner lever 34H, a center friction disk 380H, an upper handle assembly 32H, and an electronic program module 382H. In this embodiment, the friction disk 380H is firmly attached to and electrically connected to the lower handle assembly 34H and rotates with respect to and is intermittently electrically connected to the upper handle assembly 32H to provide an electrical connection between the electrical programming section 382H and the friction assembly that includes the upper and lower handle assemblies and the friction disk 380H with this arrangement, pressure between the handle assemblies and the friction disk is controlled by the program section 382H during flexion and extension. The friction disk may be part of the inner or outer handles rather than a separate disk in some embodiments.

In this embodiment, the shaft or bolt 74H is threaded through aligned openings 384, 386H, and 388 in the inner handle assembly 34H, friction disk 380H and outer handle assembly 32H to hold the units together. The electronic program control 382H is fastened for rotation with and electrically connected to the upper handle assembly 32H.

In one embodiment, the lower handle assembly 34H includes a surface 385H that is magnetic and adapted to be pulled inwardly by a variable magnetic force. An outer conductive band 387 is adapted to cooperate selectively with electrical portions of the friction disk 380H and a plurality of openings 398H circumferentially spaced from each other and underlying the friction disk 380H, are in contact with the conductors passing therethrough to form an electrical path interconnecting all of the conductors which pass normally through the disk 380H from top to bottom. In another embodiment, a motor 426 engages the bolt 74H with its output shaft to drive the bolt in the manner of a ball screw and the lower plate or inner plate has cooperating threads in its central aperture that engage the threads of the bolt in the manner of a ball screw and nut to move the two levers toward or away from each other as the motor rotates.

To cooperate with the friction disk 380H in generating friction, the upper assembly 32H includes a plurality of conductors 400H circumferentially spaced around its periphery and adapted to electrically contact different ones of the conductors passing through the surface of the friction disk 380H. Its bottom surface circumferentially engages the top surface of the friction disk 380H. The circumferential conductors 400H are electrically connected to the electronic control module 382H and spaced so that they are electrically connected to the ring of conductors 402H passing through the friction disk 380H, which conductors 402H contact and are energized by the conductive band 386H in the bottom assembly 34H. With this arrangement, the clock pulses applied to certain ones of the conductors 400H energize the conductive band in the lower assembly and provide timing pulses that are affected by both the time the clock pulses are applied by the electronic control panel 382H and the spacing between the outer and inner lever assemblies 32H and 34H.

The electronic pressure control module 382H is electrically connected to a strong magnetic coil in its lower surface with the ability to attract the magnetic portion 382H of the lower lever assembly 34H and thus force the two assemblies 32H and 34H together with increasing or decreasing force depending on the current transmitted by the computer module through its coil to vary the field. In this manner, the electronic pressure control module may control the frictional force and resistance to motion in flexion and extension and may indeed even serve as an electronic brake stopping motion or releasing the members to move freely.

Clock pulses are applied through selected ones of the conductors extending to the bottom of the upper lever assembly 32H and electrical signals are returned from the lower assembly 34H through the conductive band when it is energized by clock pulses transmitted through conductors 402H at selected positions. In this manner, the spacing of the conductors in the upper lever assembly 32H determines the transmission of clock pulses and the retiming of reception of clock pulses in relation to the positions of the upper and lower lever assemblies 32H and 34H with respect to each other by virtue of the irregular spacing of the conductors passing through the upper assembly. In this manner, a code is generated for application to the upper electronic assembly 382H in relation to the spacing of the upper and lower lever assemblies with respect to each other and a program to be described hereinafter within the electronic control assembly.

Of course, while the code in the embodiment of FIG. 42 is generated by electrical contact between the moving members, other mechanisms can be used, such as an optical or magnetic reader that senses indicia with the magnetic or optical reader being in the upper handle assembly and the indicia in the lower lever assembly. In addition, many other techniques, well known in the art, can be utilized to provide coded signals to the electronic module 382H. Similarly, many different mechanisms may be utilized by the electronic resistance to motion module 382H to control the amount of force exerted in resistance to movement, including the control of pressure to solenoids or the tightening or loosening of a mechanical device in the form of a solenoid that urges the upper and lower lever assemblies together or loosens them. For example, instead of exerting magnetic force directly on the lower assembly, the shaft 74H could extend upwardly through a solenoid coil and be pulled or released against the bias of a spring in proportion to resistance to motion or hydraulic or pneumatic control could be used.

In FIG. 43, there is shown a view taken through lines 43—43 of FIG. 42 showing the outer handle assembly 32H and the plurality of conductors 400H passing through and adapted for engagement with an electrical connection to the module 382H (FIG. 42) at a plurality of locations. The module 382H is fastened to and moves with the lever assembly 32H so as to permit permanent electrical connection to the conductors 400H passing therethrough so that the electrical resistance program can selectively energize certain of those conductors and receive signals from certain others of those conductors.

In FIG. 44, there is shown a block diagram of the resistance program module 382H having an input decoder 412, an output decoder 414, a buffered parallel-to-serial converter 416, a buffered serial to-parallel converter 418, a microprocessor 420, a timing pulse output 422, interfaced drivers 424 and a magnetic brake coil and/or motor 426. The microprocessor 420 applies coded signals through the buffered serial-to-parallel converter 418 through the decoder 414 to output conductors in the outer lever assembly 32H (FIG. 42).

The coded signals interact through conductors on the friction disk 380H (FIG. 42) to interconnect through the conductive rim of the inner lever assembly 34H to provide a series of coded pulses thereto. These pulses are electrically connected through other conductors 402H in the friction disk 380H back to the microprocessor 420 by way of the decoder 412 in the buffered parallel-to-serial converter 416 to indicate the position of the outer and inner lever assemblies 32H and 34H. This position is compared with stored program values which send signals to the interface drivers 424, that control the magnetic brake coil and/or motor 426: (1) in one embodiment, resulting in varying current applied to the magnetic brake coil 426 to alter the attraction between the outer and inner lever assemblies 32H and 34H in accordance with the program; or (2) in another embodiment, resulting in a constant current being applied to a motor for a fixed time, with the bolt 74H being threaded into the output shaft of the motor to change the pressure by tightening or loosening the friction surfaces as the bolt is moved further away or toward the motor. The motor is used when the attraction between the surfaces provided by the magnetic field is insufficient.

In one embodiment, a display 423 is provided of the position for analysis on a monitor and a second display 425 provides images from a fixed program to the patient. The later display may include an interactive program such as for a ski slope with images and resistance to movement provided by the friction modules that change as the patient moves the braces. Moreover, virtual reality may be obtained by using two different displays one in front of each eye to provide a three dimensional view and sound through earphones. Feedback signals can be used to select image and sound programs in response to the user's movement and friction can be varied in accordance with the program.

In FIG. 45, there is shown a block diagram of the relevant functions of the microprocessor 420 having a comparator 450, a clock 452, a serial memory 454, a program memory 456 and a digital-to-analog converter 458. The comparator 450 receives signals from the decoder 412 (FIG. 44) through the buffered parallel-to-serial converter and compares them with stored signals in the memory 454 under control of the clock 450. Recognition of matched signals in the comparison result in signals being applied by the comparator 450 to the program memory 456, which in turn sends signals to the digital to analog converter 458 to vary analog signals on the conductor 460. The clock 452 provides clock pulses through the output conductor 422 to the buffered serial-to-parallel converter 418 (FIG. 44) for decoding in the decoder 414 (FIG. 44) and application to the conductors 410 (FIG. 44) in the outer lever assemly 32H (FIG. 42).

With this arrangement, coded signals are transmitted and collated with the position of the outer and inner lever assemblies to indicate the position of the lever arms and their direction of movement. This in turn causes a readout of stored programs collated with the positions to control a magnetic brake coil and thus control a resistance to movement.

The position code is provided by the connection between conductors in the friction disk that are evenly spaced for each position so as to be combinations that are a different linear distance apart and cooperate with similar spacings in the outer lever assembly 32H. The direction of movement is indicated by a numerical sequence in conductors formed similar to a vernier calibre so that each increment of movement indicates a sequence of movement in one direction and increments of movement in the other direction energized the same conductors in the reverse sequence. This is accomplished by evenly spaced conductors as combined with conductors of a slightly different spacing. The embodiment of FIGS. 42–45 provides (1) a single-plane, bi-directional, variable range-of-motion and preprogrammed electromagnetic velocity-independent resistance; and (2) in addition, uses a solenoid, stepper motor, or other methods, to actuate reader plate in or out against friction pad based on computer generated program for each direction, from a microprocessor control unit. This embodiment has several advantages such as: (1) the computer generated program allows the clinician or user to quickly create any custom program and this allows for an infinite number of program choices so that patients are able to immediately use specialized programs tailored to their specific situation; (2) specific programs can be altered at the clinic based upon clinical use, findings, or evaluations; (3) increased resistance capabilities allow the device to be placed into large stand alone machines in addition to the bracing systems; (4) sensors can determine if resistance is adhering to preset program, and make any adjustments to increase the relaibility of adhering to the preset program.

In FIG. 46, there is shown a side view of an embodiment of outer lever assembly 32H having a disk portion 500, a step down portion 502 and a clamp portion 504. The disk portion 500 is disk shaped having a central opening to receive the shaft 74F (FIG. 6) and four openings 313 surrounding it to receive posts from the ramp disk 90F (FIG. 6) to hold the upper lever assembly 32F to a ramp disk such as that shown at 90F in FIG. 6.

The clamp system 504 is adapted to clamp quickly onto a brace and includes for that purpose posts 506 and 508 extending outwardly (into the paper in FIG. 46), an upper wall 510, a lower wall 512 that extends part way toward the upper wall forming a generally C-shaped configuration. The transition section 502 connects the disk portion 500 and the clamp portion 504 at an angle to accommodate the elevation of the outer lever assembly 32F (FIG. 6) above the inner lever assembly 34F (FIG. 6).

In FIG. 47, there is shown a partly exploded, perspective end view in the direction of lines 47—47 of FIG. 46 showing the C-shaped portion 530 and facing inverse C-shaped portion 526 that form a clamp. The C-shaped 530 portion has a top 510 and the inwardly extending portion 522 that slips over one side of the brace and the inverse C-shaped portion 526 has a top and inwardly extending portion 524 that receives the other side of the brace.

The portion 526 matches with this first portion and contains an opening 520 adapted to receive the post 506 and a similar opening parallel to it to receive the post 508 (FIG. 47) so that the two members may be snapped together. In actual practice the post 506 has a retainer on one end that fits within a lip of the opening 520 so that it cannot be fully retracted but only opened to accommodate the brace. When inserted fully, a spring biased detent 520 snaps into a groove, from which it can be removed by pushing downwardly. Generally, 520 is L-shaped so as to grip the post 506 from the lower end and removable by depressing the spring biased pin 520.

In FIG. 48, there is shown a side view of an inner lever assembly 34H similar to the assembly 34F except that it includes a clamping mechanism 530 identical to the clamping mechanism 504 except reversed so as to be adapted for the inner lever assembly rather than the outer lever assembly. However, the transition portion 532 is relatively level since it does not have to be stepped downwardly from the disk portion 534 of the inner lever asssembly 34H.

In FIG. 49, there is shown an end, perspective, partly-exploded view in the direction of lines 49—49 in FIG. 48 showing the bolt 509 positioned to clamp the end member 511 to hold it thereon similar to the operation of the lever arm 32H.

In FIGS. 50–54, there are shown a top view of the first lever 32H, a top view of a second lever 34H, a side view of a clamping mechanism for the first lever 32H, a bottom view of the clamping mechanism for the first lever 32H, a side view of the clamping mechanism for the second lever 34H and a bottom view of the clamping mechanism of the second lever 34H. These parts permit ready clamping of the module of this invention to a leg brace.

Figure 50:
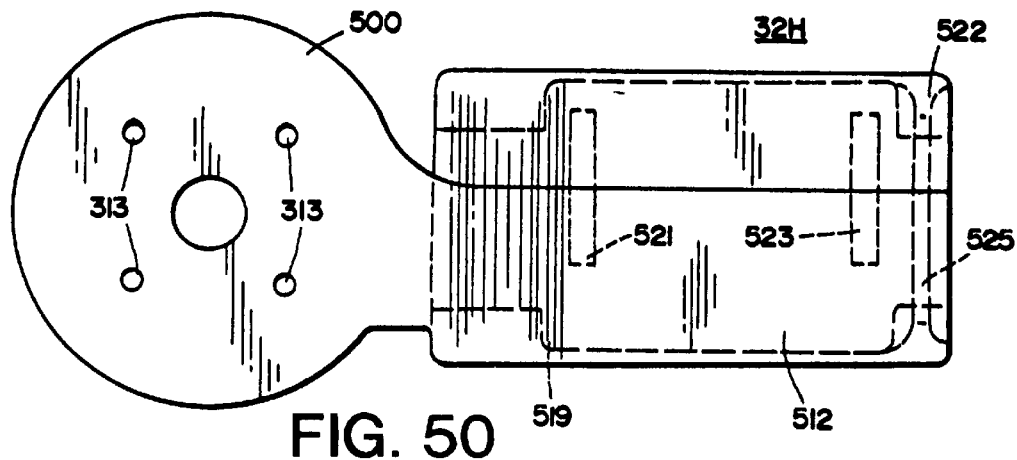
FIG. 50 is a plan view of the lever arm of FIG. 46.
Figure 51:
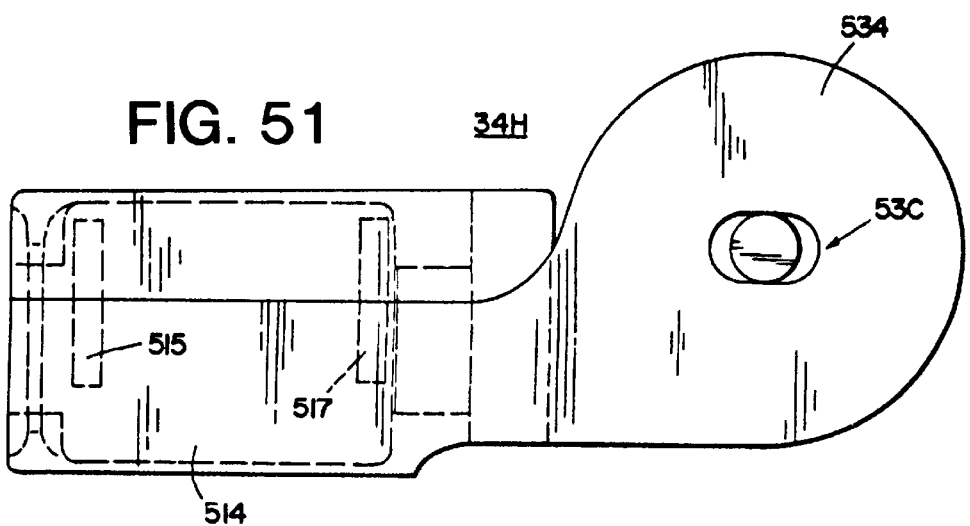
FIG. 51 is a plan view of the lever arm of FIG. 48.
Figure 52:
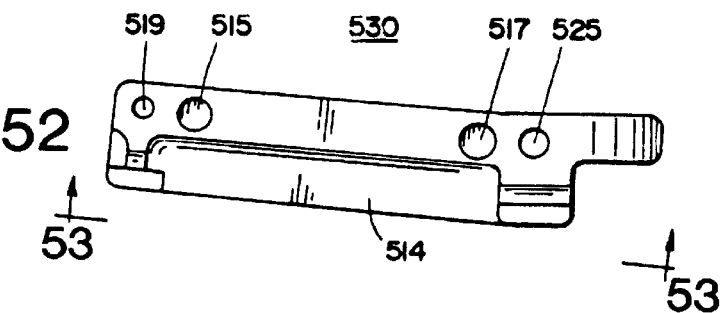
FIG. 52 is a side view of a movable portion of the handle clamp of FIG. 46.
Figure 53:
FIG. 53 is a side view of the portion of the handle clamp of FIG. 52 taken in the direction of lines 53—53.
Figure 54:
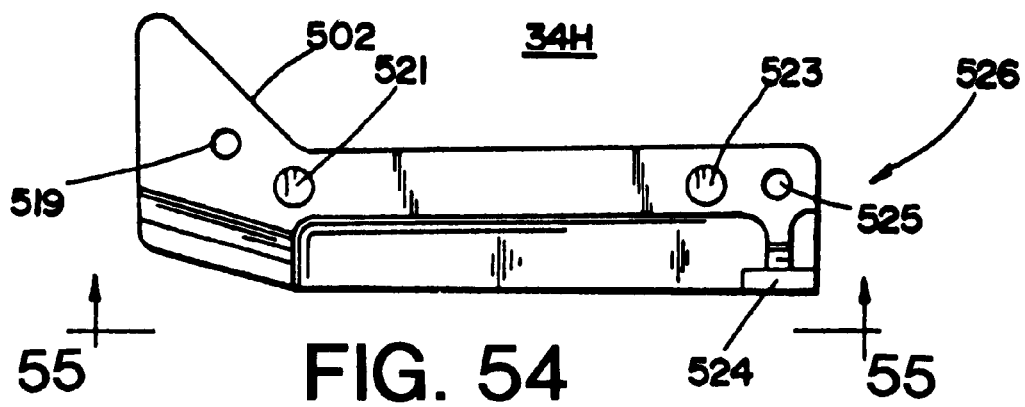
FIG. 54 is a side view of a movable portion of the handle clamp of FIG. 48.

The second clamping portion shown in FIGS. 52 and 53 engage with the lever mechanism of FIG. 50 so that the two sides can be moved together and clamp against a brace. Similarly, the second portions of FIGS. 54 and 55 cooperate with the lever assembly of FIG. 51 so that they slide apart and together and clamp over the brace.

The first lever 32H includes posts 521 and 523 which fit within the clamping section 526 as well and permit sliding of the clamping section and lever assembly together within a range permitted by the screws 519 and 525. Similarly, the second lever section includes posts 515 and 517 that extend between the clamping section and the lever itself as shown in FIGS. 64 and 65 and permits sliding between the two so that they may fit over the brace and be snapped together.

Figure 56:
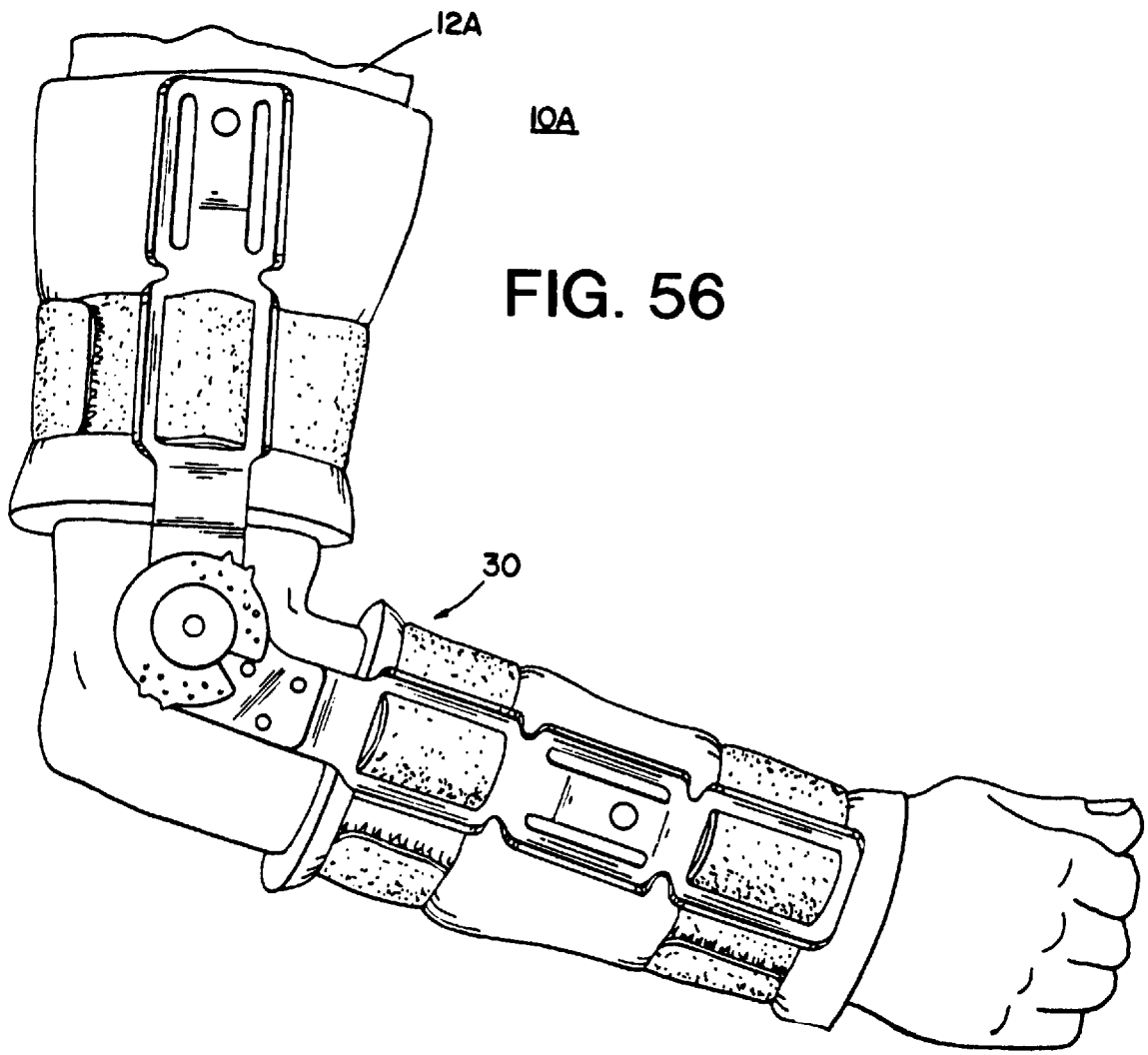
FIG. 56 is perspective view of another embodiment of the invention illustrating the use of the invention on an elbow.

In FIG. 56, there is shown a prospective view of exercise assembly 10A designed to include an arm brace similar to the leg brace of exercise assembly 10 (FIG. 1) and adapted to receive a control module 30 which may be snapped in place in a similar manner to permit exercise of an arm 12A without removing the arm brace. This arm brace is identical in every respect to the leg brace except for the settings of range of movement and the program for resistance of movement that are altered to accommodate the nature of an elbow injury rather than a knee injury. As in this case, different friction surfaces are selected depending on whether the lever assemblies are being moved closer together or further apart and these surfaces may also be contoured to vary the amount of friction in either direction.

Figure 57:
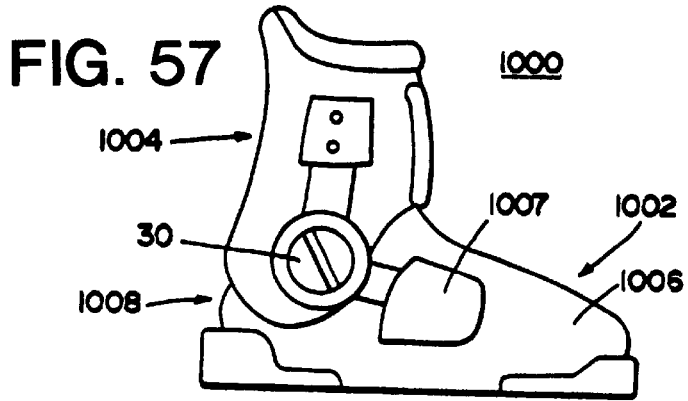
FIG. 57 is an elevational view of a ski boot designed in accordance with an embodiment of the invention.

In FIG. 57, there is shown an elevational view of a ski boot 1000 having a toe portion 1002, a heel portion 1008, a back portion 1004, and a module 30 having its lever arms connected to the toe portion and back portion in the vicinity of the ankle.

In this embodiment, the toe portion 1006 and the back portion 1004 are stiff, but they are movable one with respect to the other and the heel portion 1008 has flexible material between a hard heel seat so that the boot portion 1004 may move back and forth. To accomodate movement about the module 30, the lever arms slide within pockets 1005 and 1007.

Figure 58:
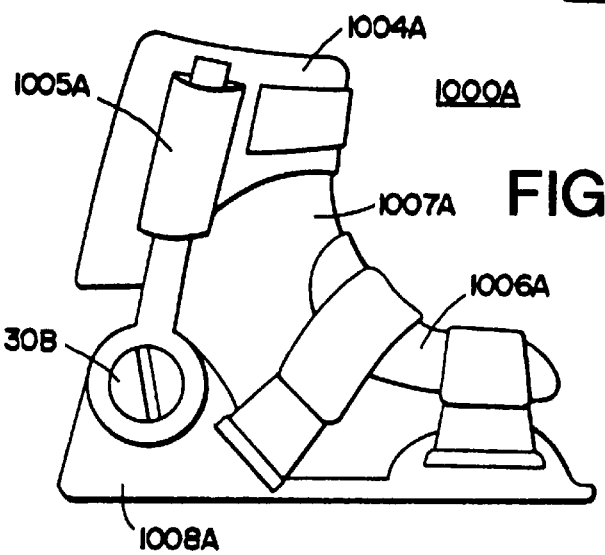
FIG. 58 is an elevational view of another embodiment of ski boot designed in accordance with an embodiment of the invention.

In FIG. 58, there is shown another embodiment of ski boot 1000A similar to the embodiment of FIG. 56, except that a single module 30B is mounted to a relatively stiff heel portion 1008A with a space between the stiff back portion 1004A and the heel portion. The stiff toe portion 1006A which is clamped by regular clamps to the heel portion is separated from the stiff back portion by a flexible material 1007A so as to permit motion back and forth. The single lever arm of the module 30B extends upwardly into a slidable portion 1005A and, the module itself has its second portion firmly mounted to the heel 1008A.

Figure 59:
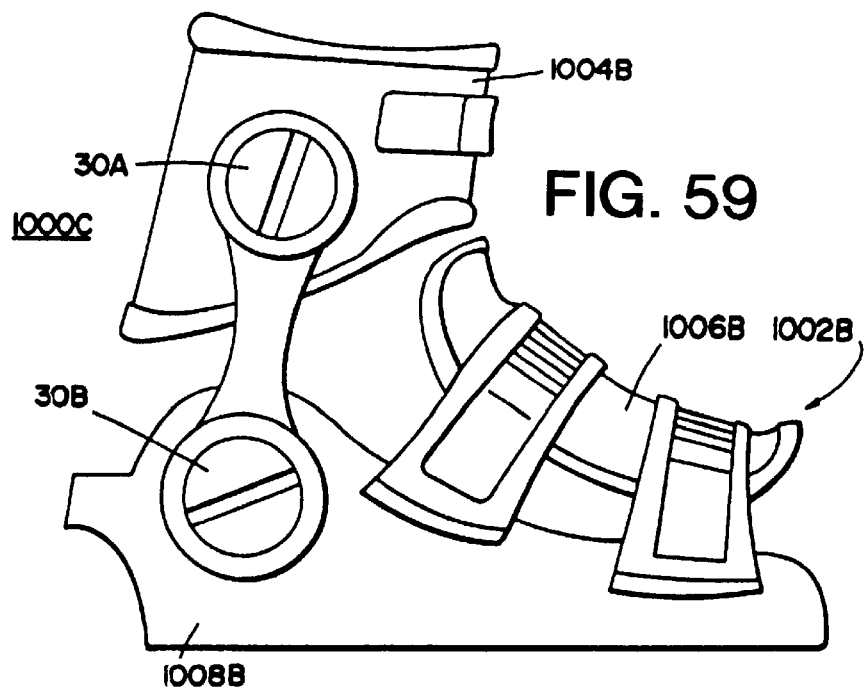
FIG. 59 is an elevational view of still another embodiment of ski boot designed in accordance with the invention.

In FIG. 59, there is shown still another embodiment of ski boot 1000C similar to the embodiment of FIG. 57 but having two modules 30A and 30B connected together by a single arm to permit still further variations in the movement of the stiff portion 1004B of the boot with respect to the stiff bottom portion 1008B with these portions being connected by flexible material. In each of these embodiments, the module 30A may be of the type having feedback sensors which may be electrically connected to a computer arrangement for virtual imaging.

The exerciser embodiments of FIGS. 1–55 may be attached to exsisting braces such as lower extremity braces or upper extremity braces and provide for controlled exercise of the person wearing the brace or may be part of another controlled resistance device. They provide controlled resistance therapy for persons with injured extremities or joints or possibly other body parts, with the resistance being movement that is related in a precontrolled manner to the position of the part being exercised. They provide an exercise device and technique that provides resistance to movement that is related in a pre-programmed manner to the position of the part being exercised but is applied independently of speed.

This equipment permits tailored exercise programs for a wide variety of purposes, such as to strengthen principally the fast twitch muscle or the slow twitch muscle or to strengthen only certain portions of an injured muscle. The user varies the speed along a resistance program which provides resistance to movement related to position but which does not generate an external force so unless the user is applying force, no resistance is applied by the equipment and the mechanism is released.

In another embodiment, the exercise device is coupled to images or other sensed programs so that the user can correlate muscle activity with sensed events. With this arrangement, the user can visualize on a cathode ray tube such as a head mounted unit, an activity such as skiing and the screen shows the terrain so the user can adjust his position accordingly. Sensors indicate the result of his actions and provide a controlled resistance related to his motion. Some equipment such as ski boots or the like are provided with a programmed resistance using the exerciser to provide protective and useful amounts of resistance to movement in controlled directions.

The resistance to movement during exercise is related in a pre-controlled manner to the position of the part being exercised, but the relationship between position and resistance is not proportional to an average motor performance curve but instead constructed for specific purposes. This exercise device can be conveniently used in either open kinetic chain exercise or closed kinetic chain exercise.

In a preferred embodiment, the means for controlling the amount of force includes one or more frictional resistance members that are removably attachable to a conventional brace or other fastener to provide a desired resisting force to movement. The frictional resistance members may include either (1) a mechanism that releases for free movement in one direction but only moves with resistance against force in the other direction; or (2) a mechanism that provides controlled variable or constant resistance in either or both directions. Generally, adjustable stops or limit members to control the amount or range of motion are provided. However, the resisting force may be provided by force members such as springs or motors or stretchable members or pneumatic cylinders or the like.

Friction members and pressure members that work together to provide frictional force against movement are used in the preferred embodiment because mechanisms that use friction to control the amount of resistance to motion are relatively easy to adjust for different amounts of resisting force by adjusting the pressure normal to frictional surfaces that move with respect to each other.

In the preferred embodiment, a knee brace or elbow brace includes first and second sections connected at a pivot point.

For one use, the first section is attachable to the leg (tibia and fibula) by a first connecting means and the second section is connected to the thigh (femur) by a second connecting means. For another use, the first section is attachable to the forearm (radius and ulna) by a first connecting means and the second section is connected to the arm (humerus) by a second connecting means. In either use, a first lever in the first section removably snaps onto the first connecting means and a second lever in the second section removably snaps onto the second connecting means, with the two levers being connected to a friction control module centered at the pivot point. The friction control module controls the amount of friction against which the first and second connecting means move.

In the preferred embodiment, frictional members are moved with respect to each other as the two levers move. The amount of friction is controlled: (1) in one embodiment, through a ratchet member that causes the two disks to be forced against each other in one position but releases them so they are separate in another position; (2) in another embodiment, through a ramp mechanism that is engaged to push the disks together in one direction of motion with motion in the other direction causing the two members to be separated by one of them sliding downwardly on the ramp; and (3) in still another embodiment, a microprocessor-controlled pressure device that controls both a basic overall pressure or minimum pressure and variations in pressure to create variations in resistance to motion in different directions of movement. An overall bias pressure may be established by a tightening mechanism that applies normal pressure between two friction members.

In some embodiments, the friction disks are level and flat and in others they are contoured to provide different amounts of friction at different locations in the movement of the device. The flexual and extensional friction members may be next to each other in concentric rings, or on opposite sides of each other or one beneath the other.

In the preferred embodiment, the frictional members are made to be easily connected to splints that are parts of existing commercial braces. The frictional members are housed in a control module that has levers extending from it. The levers are replaceably attached to the standard splints of the braces. With this arrangement, the control module may be attached to a brace by a person wearing the brace, used for exercise while the control module is attached to the brace and removed from the brace after exercise without removing the brace.

In other embodiments, the friction may be provided by compressing frictional plates together in accordance with a planned program, such as magnetically or by rotatable screw drive means or hydraulic plunger means or other means for varying the force between the friction plates.

The basic module can also be used in conjunction with other types of equipment such as ski boots or the like to provide a controlled amount of movement and resistance and thus avoid injury that might otherwise occur such as with an inflexible ski boot. Similarly, such equipment may include sensors so as to form visual or other sensory images while a person exercises, such as for example, images of terrain while someone is using exercise equipment simulating cross country skiing. Orthodic systems may be equipped to provide overall or relatively complete exercise environments or other simpler equipment now equipped with weights to provide isotonic exercise may instead be equipped with control modules to provide controlled resistance in accordance with the position of the anatomical segments being exercised.

In FIG. 60, there is shown a simplified fragmentary, partly sectioned elevational view of a multiple-plane exercise device 1050 including as its principal parts a first lever arm and holder assembly 1052, a second lever arm and holder assembly 1054 and a control module 1060. The control module 1060 connects the first and second lever arm and holder assemblies 1052 and 1054 in a manner similar to that of the embodiments of FIGS. 3 and 10–69 and the exercise device of FIG. 60 is adapted to be fastened to body portions on opposite sides of a limb to control the amount of force necessary to move about that joint.

While the previous embodiments control only pivotal motion in a single plane, the exercise device 1050 controls motion in a multiplicity of different planes and directions, providing for rotary motion of one body part with respect to another and pivotal motion in a number of different planes and combinations of rotational and pivotal motion between the body parts. It provides resistance that is controlled independently of speed and can be programmed to vary the resistance as a function of time, or as a function of position and as a function of speed at the option of the programmer.

The first and second lever arm and holder assemblies 1052 and 1054 each include a different one of the two holders 1056A and 1056B respectively and a different one of the corresponding first lever arm assemblies 1052 and second lever arm assemblies 1062. The holder 1056A is fastened to the lever arm assembly 1058 and shaped and designed to hold a body part for one side of the joint which moves with respect to a second body part and the holder 1056B is fastened to the lever arm assembly 1062 for movement therewith and sized and shaped to hold the second body part that moves about a joint.

The module 1060 that connects the first and second lever arm and holder assemblies 1052 and 1054 is mounted in juxtaposition with the joint or portion of the body that connects the two body parts that move with respect to each other. The word joint in this specification not only includes conventional joints such as elbows or the like but also other body parts that permit or control the articulation of one body part with respect to another. Thus, while holders best adapted for an elbow or a knee are shown in FIG. 59, it is obvious that different shapes and sizes of holders may be fastened to the lever arm assemblies and adapted to connect to other body portions to control articulation about the neck, or back.

The first and second holders 1056A and 1056B are similar and in this specification their corresponding numbers except for the respective suffixes A and B. Thus only one will be described which is generally the holder 1056B.

The holder 1056B includes a tubular sleeve wall 1064B, a holder opening 1066B, a hinge 1068B, three latch members 1070B, 1072B and 1074B. The sleeve wall 1064B is adapted to open about the sleeve opening 1066B by pivoting about the hinge 1068B. When closed, the latch members 1070B, 1072B and 1074B hold it closed. They may be a hook and loop fabric holder or a mechanical latch of any type.

With this arrangement, the two holders 1056A and 1056B can be mounted on different sides of a joint or other body part that controls articulation to permit movement in a variety of planes under the control of the control module 1060 and an appropriate program where variations are to be made in friction with respect to time, position or velocity.

The first lever arm 1058 includes a first lever body 1076 and a program unit 1078. The first lever body 1076 is a support adapted to be fastened to the holder 1056A and to mount the program section 1078 rigidly thereto and may be of any shape such as the tubular shape shown in FIG. 60 but can be a flat shape or round shape or any other appropriate shape.

The program unit 1078 includes a first friction surface 1080, a drive unit 1082, and a holding unit 1088. It is fitted to cooperate with a universal joint and a friction surface, which are part of the control module 1060. With this arrangement, the drive unit 1082 exerts force under the control of a program on the first friction surface 1086 which engages the friction surface 1086 of the universal joint 1084 to vary the resistance against a force applied between the two lever arm and holder assemblies 1052 and 1054. The control of the drive system may be pneumatic or electrical and may operate the drive unit 1082 in the manner of a stepping solonoid or a pneumatic or hydraulic piston under the control of a computer.

The universal joint 1084 includes a cylinder having upon it the friction surface 1060 and is held captive within the program unit 1078 with the friction surface engaging the friction surface 1080 along a solid arc. In embodiments providing for ultamatic changes in the pressure between the friction surfaces, the friction surfaces can be uniform but, on the other hand, variations in either of the friction surfaces as to thickness or coefficient friction may be used to program the resistance at different angles between the first lever arm and, holder assembly and the second lever arm and holder assembly 1052 and 1054.

To cooperate with the control module 1060 and the first lever arm assembly, the second lever arm assembly 1062 includes a second lever body 1100 and a universal joint unit 1102. The body portion 1100 is tubular and fastened to the sleeve 1056 to move therewith and connected at its end to the universal joint unit 1102.

The universal joint unit 1102 includes a housing for a portion of the control unit 1060 including the universal joint stem 1006, a spring 1104, a retainer ring 1108 and a detent member 1106. The detent 1110 is on the stem 1106 and is pressed upwardly against the retainer ring 1108 on the end of the universal joint unit 1100 so that the spring biases the stem 1102. The stem 1102 fastened at its other end to the universal joint ball within the universal joint unit 1078 held by the first lever arm 1058. With this arrangement, the stem 1106 has some leeway and can be biased inwardly against the force of the spring 1104 and nonetheless, is in contact with the friction disk 1080 and captured within the universal joint member 1078.

The control module 1060 includes an end ball forming a portion of the universal joint 1084. The diameter of the ball is greater than an opening in the end of the universal joint unit 1078 so as to be captured as part of the first lever arm 1058 but connected to the stem 1106 which extends into and is held by the detent 1006 and retainer ring 1108 of the second lever arm 1062. With this arrangement, the friction surface 1080, which is pressured by the drive unit 1082, controls the resistance against force that attempts to move the two lever arms apart in accordance with a controlled program.

At the top of the spherical portion of the universal joint extending from the housing 1094 are a plurality of markings 1092 and mounted at the end of the unit is a sensor 1090 which senses the markings and provides signals on conductors 1091. The sensor generates signals on conductors 1091 indicating the position of the first lever arm and holder assembly and the second lever arm and holder assembly with respect to each other. This signal may be fed to the computer which in turn, supplies signals to the drive unit 1082 to control the pressure and thus the frictional resistance to be applied at that location.

The control module 1060 includes and cooperates with the drive system 1082, first friction surface 1080, second friction surface 1086, universal joint 1084, holding unit 1088, sensor 1090, markings 1092 and stem 1106. With this arrangement, the control module 1060 interconnects the first lever arm and holder assembly and the second lever arm and holder assembly to control the amount of resistance to force in accordance with location and in some embodiments time or speed of movement, and to provide information to a central controller as to the position of the first lever arm and holder assembly with respect to the second lever arm and holder assembly.

In FIGS. 61 and 62, there are shown a longitudinal sectional view and an end view respectively of the housing 1094 which cooperates with the control module 1060 (FIG. 59) to control the amount of frictional resistance created by the exercise device 1050 (FIG. 60) including an outer housing wall 1120, a cylindrical bushing 1122, a retainer ring 1124 and an externally threaded retainer nut 1126. The retainer ring 1124 is sized to close the wall 1120 and having a curved interior and an opening adapted to confine rotatably the spherical portion of the universal joint 1086. The retainer nut 1126 cooperates with the internal threads 1128 on the wall 1120 to hold the retainer ring in place confining rotatably the cylindrical portion of the universal joint 1086 to cause it to cooperate with the friction surface. The friction surface is complimentarily shaped to the sphere shown at 1080 in FIG. 60. The bushing is adapted to receive and confine the drive unit 1082 (FIG. 60) which in turn retains the solonoid that controls the outward pressure exerted by the frictional surface 1080.

In FIGS. 63 and 64, there are shown a longitudinal sectional view and an end view respectively of the control module 1060 having a drive unit 1082, a first friction surface 1080, a universal joint 1084, a stem 1106 for the universal joint and a retainer ring 1108. The solonoid 1130 operates in a step by step fashion to push the first friction surface 1080 against the friction surface 1086 on the universal joint 1084.

The stem 1106 provides a coupling to the second lever arm and housing 1054 (FIG. 60) but the resistance to movement in a pivotal direction or circular direction in this embodiment is provided by the interface between the first friction surface 1084 and the second friction surface 1086.

On the side of the ball joint facing away from the solonoid 1130 and extending beyond the second arm assembly, there are a plurality of markings 1092 which may be physical projections sensed by a physical sensor or optical markings sensed by a photocell arrangement to convey the position of the first and second lever arm and holder assemblies 1052 and 1054 with respect to each other. The stem 1106 includes a retainer ring 1108 that limits the motion of the stem so to maintain it within the second lever arm assembly 1062.

In FIG. 65, there is shown an end view of first lever arm and holder assembly 1052 having a first lever body 1076 and a first holder 1056A attached to each other. The universal joint 1084 and stem 1106 extend from the lever arm assembly 1076. The holder 1056A includes a latch member indicated at 1070A which snaps into its mating latch member at the opening line 1066A, a hinge 1068A and two half tubular cylinder members which snap together about a body part. With this construction, the holder 1056A may be opened, snapped over a body part such as for example a thigh with the control module fitting over the joint such as for example the knee joint and the second holder opened and snapped in place so that the first and second lever arms are mounted to body parts on opposite sides of the joint to control the resisting force to their movement.

The embodiment of FIGS. 60–65 provides a multi-plane, multi-directional, variable range-of-motion, preprogrammed electromagnetic, velocity-independent resistance. It uses solenoids, stepper motors, pneumatic cylinders, hydraulic cylinders, ball screw arrangements or any other means to actuate curved reader plates in or out against a curved ball joint. The curved ball joint may use friction or electromagnetic fields between a ball joint and its curved plate to apply changing amounts of resistance to the multi-directional, multi-plane movements of one lever arm with respect to the other while maintaining movement of the system shaft with respect to the housing controlled by a preset computerized program that sets the resistance at every degree along a three dimensional three plane range of motion, independently of any direction.

With the embodiment of FIGS. 60–65, multi-plane resistance is provided to parts connected at multi-plane joints such as a hip or shoulder. It may also be used to provide inhibiting action on one side such as for example a stroke patient with left cerebral vertebral accident disfunction may have the proximal joint (such as the left hip) inhibited during standing, sitting or lying down positions and in multi-direction patterns of movement of left hip abduction, flexion, extension or rotation to compensate for the dysfunction and to increase right extremity awareness, activity and strength. Moreover, other distal-joint, multi-direction patterns of movement can be facilitated or inhibited through neuromuscular timing during full limb activity such as for example one can decrease knee extension spasticity during hip extension.

Figure 66:
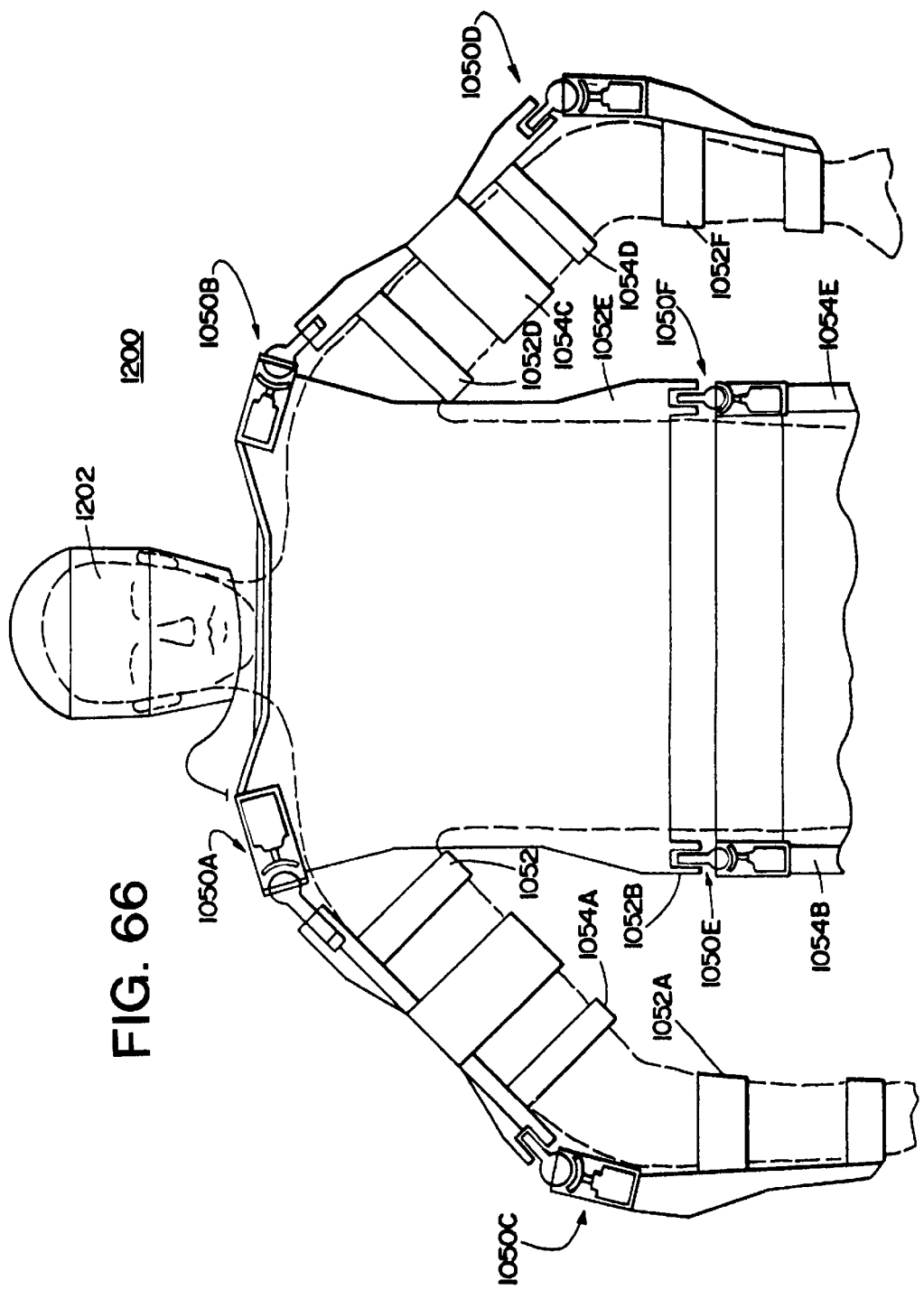
FIG. 66 is a fragmentary elevational view of an exerciser assembly using the multiple plane control unit of FIG. 63.

In FIG. 66, there is shown still another exercise apparatus 1200 having a plurality of individual exercise units 1050A–1050F on a corresponding plurality of joints. Each of the units 1050A–1050F corresponds generally to the unit 1050 in FIG. 60 and operates in the manner, having corresponding ones of the control modules 1060A–1060F lever holding assemblies 1052A–1052F and 1054A–1054E. The units control resistance to force by a subject about the shoulder, elbow and back to which they are attached but can also control other joints such as the neck. With this arrangement, each joint can be controlled for exercise purposes. A screen 1202 may be used to provide images in an interactive system that simulates a sport such as explained in connection with FIGS. 44 and 45.

In FIG. 67, there is shown a schematic side elevational view of an exercise device having a support base 1146, an expandable piston 1144 such as a pneumatic piston, holders for body parts such as 1148A–1148M and control modules in accordance with the emodiments described in the specification located at the joints which are to move during exercise such as the control modules 1142A–1142F. The piston 1144 is mounted to the base 1146 with a swivel type mounting so as to be capable of expanding upwardly or downwardly and communicates with a back rest and a seat rest through the control module 1142D.

To permit movement about joints: (1) the back rest communicates with a shoulder rest at control module 1142C and with a head rest through control module 1142; (2) the distal end of the upper arm support communicates with a lower arm support through the control module 1142; and (3) the seat rests communicate with the lower leg through control module 1142E and with the foot rest through control module 1142. This arrangement permits the controlled articulation against controlled pressure at each of the principal joints of the body.

In use, a patient may be fastened in place through the back rest holder 114A, the seat rest holders 1148F and 1148G, the lower leg rest holders 1148E and 1148D and the foot rest holders 1148C and 1148B. The head, shoulder and arm rests are fastened to the patient through the holder 1148L, the holder 1148K, the holder 1148G, the holder 1148I and the holder 1148H respectively. As shown in FIG. 68, the exercise device 1140 may be lifted with the piston 1144 so that the patient is fastened in place in a standing position. In either position, the position of the joints is secured as described in connection with the embodiments of FIGS. 60–65 and resistance to force controlled.

In FIG. 69 and 70 there are shown a longitidinal sectional view and an end view of another embodiment of control module 1150 having a housing 1152, a stepper motor 1154, 1156, a friction control shaft 1158, a retainer plate 1162 and a friction pad 1160. With this arrangement, the friction member 1158 is adapted to be fastened to one holder to control frictional movement of that holder and the stepper motor 1152 is mounted in a fixed position with respect to a programmer. Accordingly a central unit controls the friction at a joint to provide controlled resistance for exercise. The control module may also be used to control pressure between two mating sections of a universal joint such as in the embodiments of FIGS. 60–68.

In FIG. 71, there is shown the control module 1150 mounted to a stationary unit 1166 in juxtaposition with a chair 1164 so that the control 1150 controls a joint 1162 connecting the seat 1163 and the lower leg support 1161 so that the patient may exercise the knee joint under the control of the module 1150. In FIG. 71, there is shown a side elevational view of the chair 1164 showing a grip in addition to the grip about the leg rest 1161 but at a higher level such as shown at 1174. That unit may be used for arm exercise and the lower unit may be used for leg exercise.

In FIG. 73, there is shown a central control console having four circumferentially spaced control units 1166A–1166D and adjoining chairs 1164A–1164D to permit a single central control computer 1172 to control several modules which can accommodate individual patients in leg exercises or arm exercises or the like.

In the embodiment of FIGS. 60–68, multi-joint, multi-plane, multi-directional, variable range of motion, preprogrammed electromagnetic velocity independent resistance exercise may be provided. Generally, in addition to the advantages of other embodiments, this advantage has the ability to provide computer control preset resistance to multiple joints based on preset resistance values given to each joint for every combination of joint range of motion in respect to other participating joints. It can provide both flexion and extension over a wide range of motion which is preset and with the appropriate resistance for each. They are especially useful for virtual reality vision exercise embodiments and total body exercise with or without the television vision or simulated action.

The embodiments of FIGS. 60–68 provides multi-joint, multi-plane, multi-directional, variable range of motion preprogrammed electromagnetic velocity-independent resistance, virtual-reality helmet type of activity either standing or sitting down and the embodiments of FIGS. 71–73 provide single plane, multi-directional, variable, range of motion, preprogrammed velocity-independent control with virtual reality if desired. Helmet or glasses utilizing computer imagery provide images coordinated with computer monitoring of the program to vary the preset multiple joint resistance for each joint as described above. The range of motion for each joint is predetermined by one of many programs that sets the resistance value based on: (1) the range of motion position of the selected joint and the range of motion location of all other joints in relation to the selected joints; (2) the direction the limb connected to the selected joint is moving and what direction other limbs are moving in relation to the selected joints; (3) the three dimensional coordinates of the virtual reality video tape. With the use of a viewer that can artificially generate a functional closed kinetic chain activity visualization, the exerciser can see hiking or other environments as exercising with the resistance being adjusted in accordance with the motion of the exerciser in simulated hiking or rowing or skiing or the like.

Figure 74:
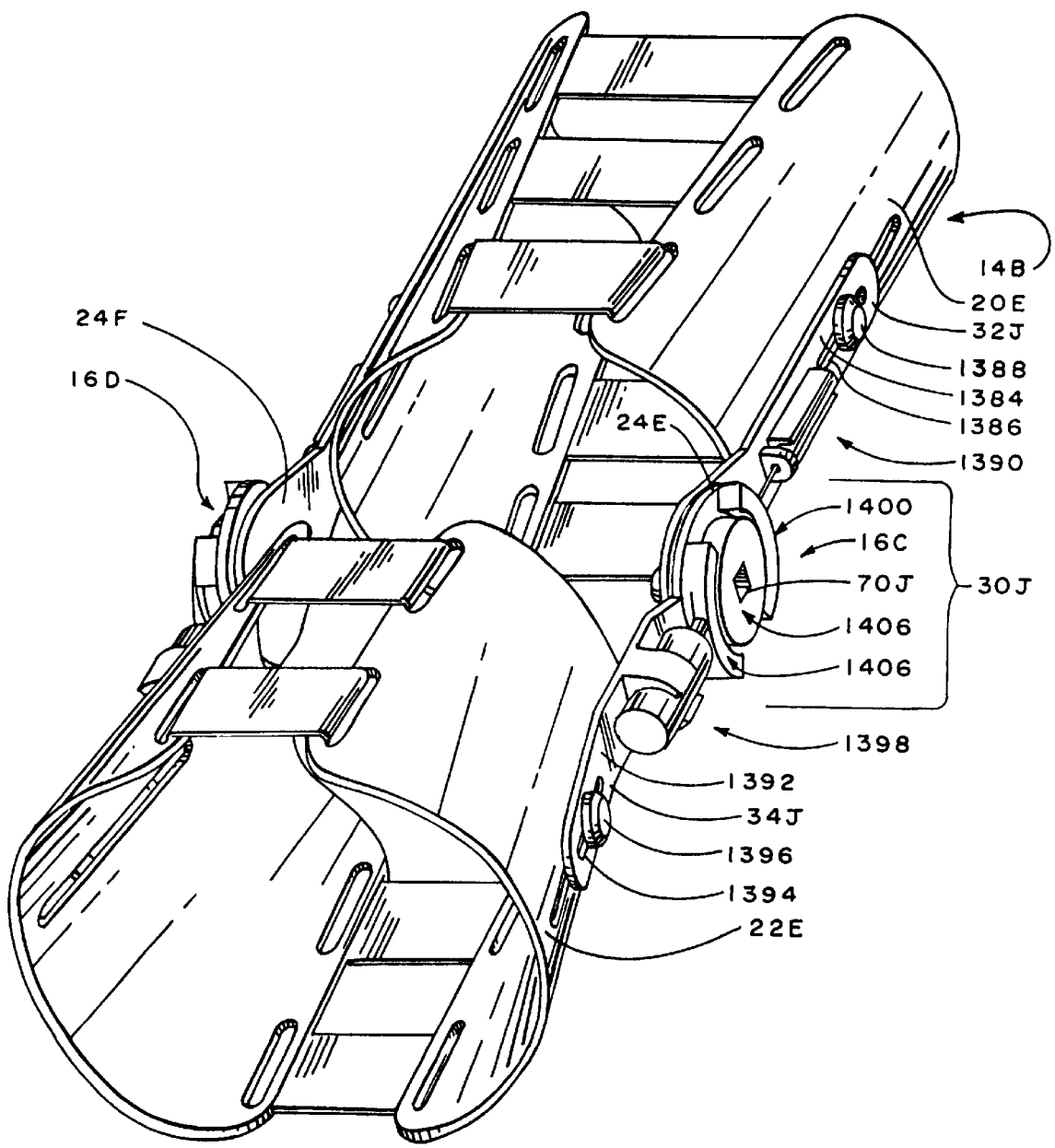
FIG. 74 is a perspective view of a knee brace showing an electrically controlable module for varying the resistance to movement of the leg with respect to the thigh.

In FIG. 74, there is shown still another exercise assembly 10E including a brace portion 14B and right and left exercise modules 16C and 16D respectively. As in the embodiments of FIGS. 1 and 2, the control modules 16C and 16D interconnect two portions of the brace about a joint that is to be protected and/or exercised. In the embodiment of FIG. 74, the exercise assembly 10E is adapted for a knee brace 14B but the exercise modules 16C and 16D may be used with other types of braces such as elbow braces or the like and for other types of exercise equipment in which controlled resistance is to be provided in two directions.

The brace 14B may be any of many standard braces and is not by itself part of the invention. It includes in a manner typical of knee braces, a first support means 20E and a second support means 22E connected together by pivotable joints 24E and 24F in a manner known in the art. The control modules 16C and 16D are each adapted to be interconnected over a respective one of the pivotable joints 24E and 24F. The right and left exercise modules 16C and 16D are identical and only the module 16C will be described.

The control module 16C includes a control assembly 30J, and first lever assembly 32J and a second lever assembly 34J. The first and second lever assemblies 32J and 34J are fastened to the control assembly 30J on opposite sides thereof with the first lever assembly 32J being adapted to be fastened to the first support means 20E to move with the thigh of a person and the second lever assembly being adapted to be fastened to the second support means 22E to move with the leg of the person.

The first lever assembly 32J includes a first lever arm 1384, a slot 1386 in the first lever arm, a positioning bolt 1388 and a position sensor 1390. The slot 1386 is alignable with a similar slot in the first support means 20E so that it can be positioned therewith and movably fastened in place by the positioning bolt 1388. The position sensor 1390 is mounted to the first arm 1384 and used to sense the position of the first support portion 20E to the second support portion 22E of the brace and thus the amount of extension or flexing of the limb or body portions about their joint.

The second lever assembly 34 similarly includes a second arm 1392, a slot 1394, a positioning bolt 1396 and an actuator 1398. With this arrangement the second arm has its slot 1394 aligned with a similar slot in the second support member 22E to be movably fastened by the nut 1396 with the actuator 1398 facing and contacting the control module 30J in line and diametrically opposite to the sensor 1390 on the opposite side. The actuator 1398 adjusts the pressure and the sensor 1390 senses the angle between the members surrounding the joint.

The control module 30J includes a shaft 70J, a first friction disk and pad 1400 and a second friction disk and pad 1402. The actuator pushes the pads against the friction disk to vary the force between the friction disk and the pad and thus the resistance to movement of the limbs or other body parts about the joint. The slot and bolt arrangement allows movement of the actuator, sensor and module as one unit so as to be able to adjust for the eccentric motion of the joint during flexing and extension.

In FIG. 75, there is shown a portion of the first lever assembly 32J and a portion of the control module 30J including the first lever arm 1384 and the first slot 1386 in the lever arm. As shown in this view, the control assembly 30J includes a friction disk 1406, a shaft 74J, a shaft head 1408, a shaft nut 1410 and a first arm base member 1412. The shaft head 1408 is a right regular parallelepiped having sides larger than the diameter of the cylindrical shaft 74J. The shaft 74J has a threaded end 1414 which engages threads in a central tapped hole of the shaft end nut 1410 to hold the friction disk 1406 to the base 1412. Aligned apertures sized approximately the same as that of the diameter of the shaft 74J extend through the friction disk and the base 1412 to provide aligned openings for the shaft to pass therethrough and be tightened by threading of the nut 1410 over the threaded end thereof. A parallelepiped shaped aperture 1416 is sized to receive the head 1408 so as to cause the friction disk 1406 to rotate together with the arm 1384.

In FIG. 76, there is shown a fragmentary perspective view of the inner lever 34J having a second lever arm 1392, a holder 1410 for the actuator 1398 (FIG. 74) and the slot 1394 for fastening to the second support means 22E. The control assembly 30G has an annular support ring 1174 and a friction base and pad 1400. The actuator 1398 presses the friction base and pad 1402 (FIG. 74) against the friction disk 1406 and also against the pad 1400 in accordance with an electrically controlled program to alter in a preprogramed manner the amount of frictional resistance against movement of the first and second levers 34J and 32J with respect to each other.

An optical sensor suitable for sensing position signals such as the sensor 1390 may be obtained from the Polyscientific Division of Litton Industries, 1213 North Main Street, Blacksburg, Va. 24060-3100 such as under the part number F03573-2. This linear sensor provides a digital signal which may be connected back to the computer (not shown in FIG. 74). Suitable actuators such as used in the actuator 1398 may be obtained from ETREMA Products, Inc., a Subsidiary of EDGE Technologies, Inc., 2500 North Loop Drive, Ames, Iowa 50010 such as that sold under catalog number 50/6m.

Figure 77:
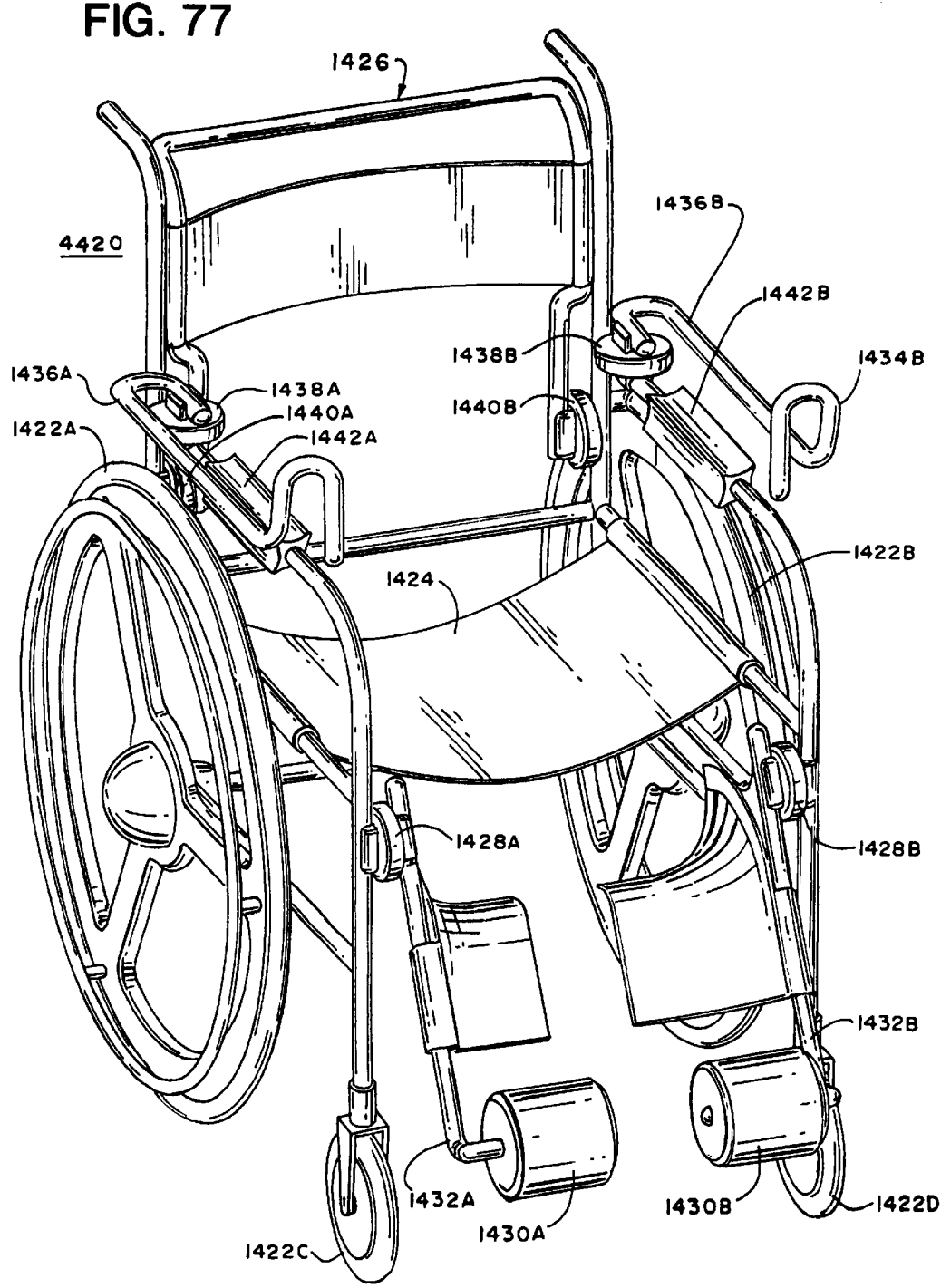
FIG. 77 is a perspective view of an execise aparatus adapted for use in a wheel chair.

In FIG. 77, there is shown a perspective view of a wheelchair 1420 having four wheels 1422A–1422D, a back rest 1426 and a seat 1424 supported on a frame in a conventional manner to permit a person to sit on the horizontal support 1424 while it is supported on the four wheels by the frame and lean back against the back rest 1426. Arm rests are provided on each side as shown at 1442A and 1442B.

The wheelchair 1420 also includes an arm exerciser having first pair of right and left control modules 1438A and 1438B, a corresponding pair of exercise shafts 1436A and 1436B and a corresponding pair of hand grips 1434A and 1434B. The control modules 1440A and 1440B are mounted on opposite sides of the wheelchair frame and are mounted to the frame so that they provide resistance along horizontal axis to movement in a preprogramed manner. They may be designed in the manner of any of the other control modules or in the manner of the control modules of FIGS. 74 through 76.

The control modules 1438A and 1438B are mounted between the frame of the chair on opposite sides of the chair to accommodate both the right and left arm, with the module 1438A accommodating outward lateral movement by the right arm and the module 1438B being positioned to accommodate outward movement by the left arm. These two modules have a vertical axes and connect corresponding ones of the horizontal arm exercise shafts 1436A and 1436B to the frame at one end of the arm shafts. The hand grips 1434A and 1434B are mounted to corresponding arm exercise shafts to provide a convenient hand grip for a person resting in a wheelchair to have controlled arm exercise about the control modules.

A programed degree of resistance in accordance with the movements of the hand laterally outward may be provided. Moreover, the modules 1438A and 1438B may be mounted to corresponding control modules of similar structure but independently programable and having axis that are horizontal and transverse to the axis of the modules 1438A and 1438B. In turn, these modules may connect corresponding ones of the arm exercise shafts 1436A and 1436B so that these arm exercise shafts may be moved with a predetermined pattern of resistance outwardly under the control of the corresponding ones of the modules 1436A and 1436B and under the control of the additional modules in a vertical direction to provide two degrees of motion to the exerciser. Thus, two of the single plane two dimentional control modules may be connected together to provide three dimentional multiple plane exercise movement.

In a similar manner, the back rest 1426 is connected to the fram by two modules 1440A and 1440B, one on each side of the backrest. These two modules form a connection between the wheelchair frame and the back rest 1426 to permit controlled resistance to forcing the back rest 1426 backwardly and thus permit exercise about the waist.

To permit leg exercise, the control modules 1428A and 1428B are mounted to the frame on opposite sides with a horizontal axis and connect corresponding ones of the leg support shafts 1432A and 1432B to the frame to provide controlled resistance therebetween. The foot rests 1430A and 1430B are connected to the opposite ends of the corresponding leg support shafts 1430A and 1430B to permit exercise of the person's legs by swinging them upwardly against the resistance provided by the corresponding ones of the control modules 1428A and 1428B.

While exercise mechanism have been shown for multiple limbs in connection with a wheelchair, these exercise mechanisms may be utilized in other types of human support structures such as ordinary chairs or beds or frameworks for supporting a person who is in a standing position. In all of these types of structures, patterns of motion in one or two dimensions for exercise may be provided with control modules at the pivot points to provide resistance against movement in accordance with the program within the control module.

Figure 78:
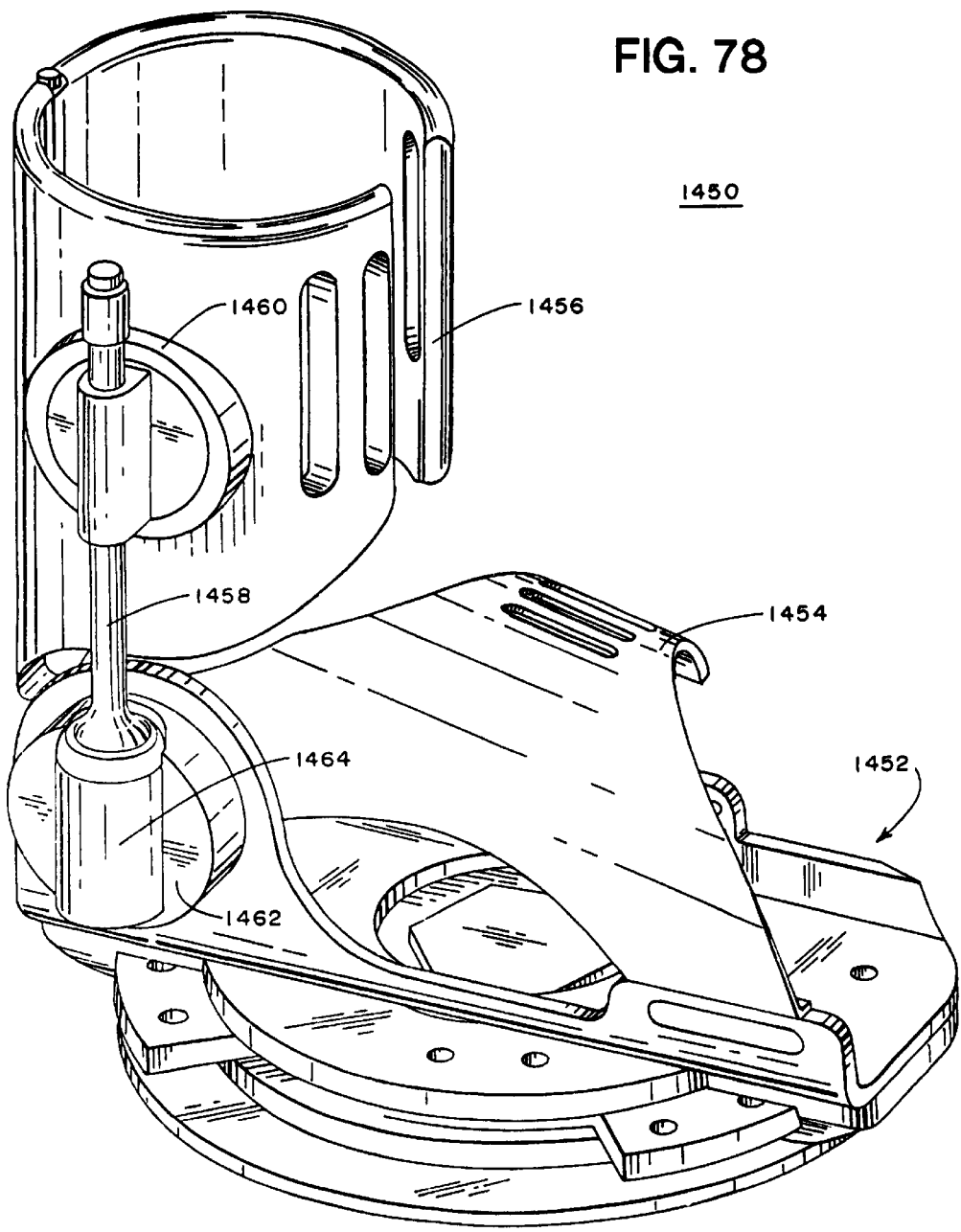
FIG. 78 is a perspective view of binding utilizing a controlled resistance support for use on snow boards.

In FIG. 78, there is shown a perspective view of a snow board binding 1450 using the control modules described above and having a base 1452, a boot latch 1454 and a leg latch 1456. The base 1452 is adapted to be mounted to the snow board in fixed position and supports the boot latch 1454 which is hinged and adapted to fasten the front part of a boot in place to the base 1452. The leg fastener 1456 is mounted to the boot fastener 1454 by a shaft 1458 which connects mountings 1460 and 1462 adjustably to each other.

The mounting 1460 is rigidly fixed to the leg latch 1456 and the mount 1462 is rigidly connected to the boot fastener 1454. The shaft 1458 is positioned to slide along a vertical axis about the mount 1460 and has, at its lower end, a three dimensional control module 1464 to provide universal joint motion with controlled preprogramed resistance between the shaft 1458 and the shoe portion 1454. Thus the shaft 1458 may pivot in any direction about a point in the control module 1464 to permit movement of the body with respect to the snow board during use.

The module 1464 is designed in the same manner as the module 1060 of FIG. 63. In the alternative, it may include two two-dimensional control modules such as the control modules disclosed in connection with FIGS. 74–76 mounted at right angles to each other so that one provides pivotable action about an x-axis and the other provides pivotable action about a transverse y-axis. The pivoting may be resisted by a preprogrammed amount of resistance in the manner described above to reduce the probability of accidents while still permitting motion. The resistance can be adjusted to provide firm support to permit weight shifting on the board but yield in some positions to avoid injury.

Figure 79:
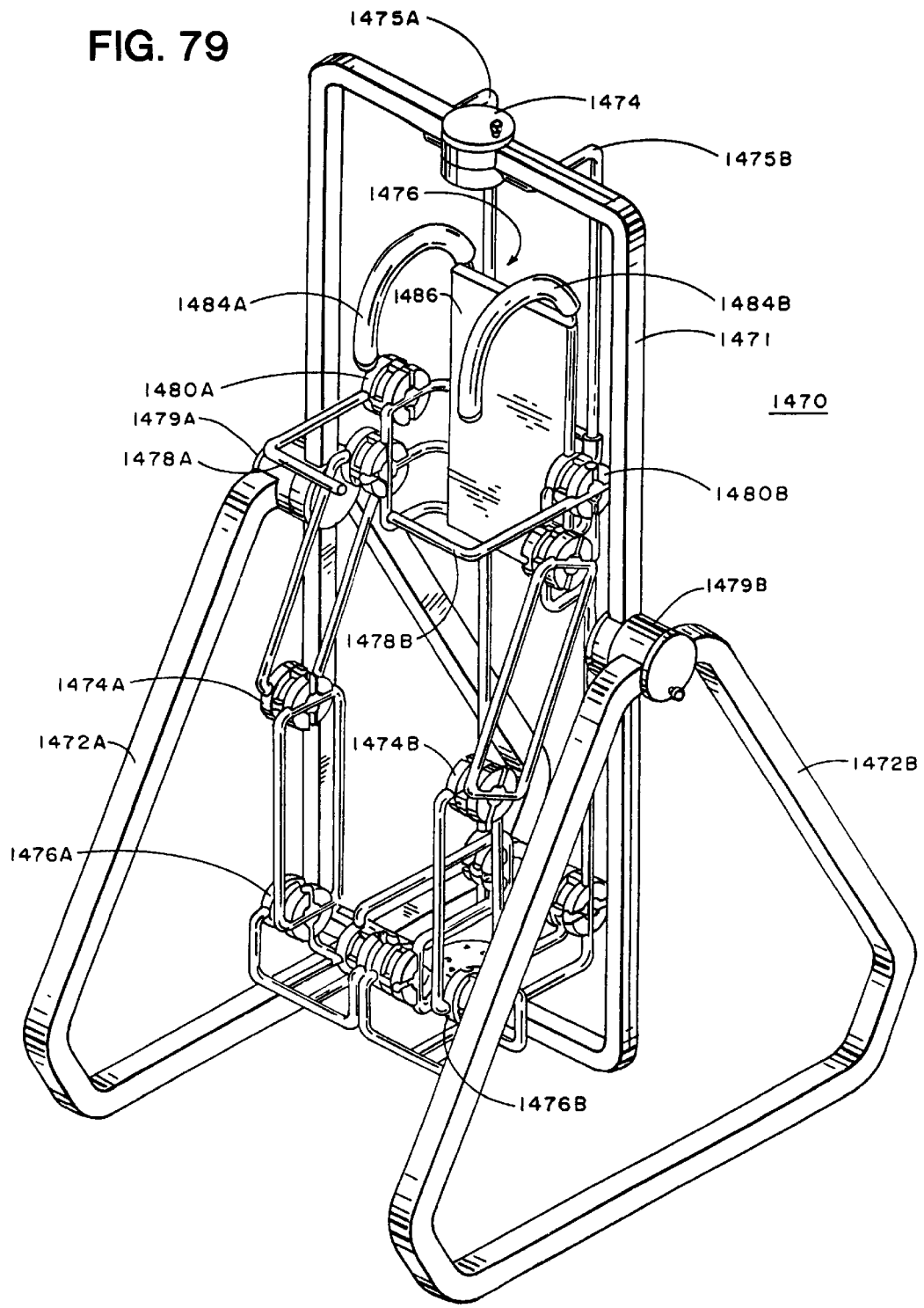
FIG. 79 is a perspective view of a type of exercise apparatus.

In FIG. 79, there is shown a standing exercise machine 1470 using the control modules described above and having a stationary frame including stationary members 1472A and 1472B adapted to rest upon a floor, a pivotable frame including member 1471 and a shoulder and back frame 1476. The pivotable frame member 1471 is a steel tube having a cross-section of a square and being shaped to form a rectangle pivotably connected to the staionary frame 1472 and to the shoulder and back frame 1476.

The shoulder and back frame 1476 includes a back rest 1486 and right and left shoulder hooks 1484A and 1484B mounted to the top of the flat panel-like back rest 1486. With this arrangement, a person exercising may press his back against the flat panel-like back rest 1486 with the shoulder supports 1484A and 1484B respectively extending in curvilinear fashion over the right and left shoulder so that the backrest and shoulder support 1476 may move with the exerciser. The backrest 1476 is relatively small having a vertical dimension of between six inches and five feet so that it may bend with the back and not touch the floor when standing vertical in its normal position.

To permit twisting action, the shoulder and back rest 1476 is mounted to the pivotable frame 1471 by a control module 1474. The control module 1474 may provide a resistance program to provide preprogrammed resistance at different angles during a pivotable action of the frame for a person holding the back and shoulder rest and twisting the upper torso.

To permit bending at the waist as an exercise, the pivotable frame 1471 is pivotably mounted at a central location about waist high to the stationary frame 1472A and 1472B by control modules 1478A and 1478B respectively to permit a person holding the shoulder rests 1484A and 1484B to bend in an action such as touching the toes.

To permit arm exercises, a hand grip mechanism 1478A and 1478B are positioned for right and left hands and mounted to the should and back rest by control modules 1480A and 1480B so that a person may exercise their arms by pivoting them upwardly and downwardly.

To provide squatting motion, the twist frame is formed of rails 1475A and 1475B which are slidably mounted to the back and shoulder support by sleeves on each side corresponding thereto and is mounted by control modules 1474A and 1474B and 1476A and 1476B to permit the downward movement of the back and shoulder rest 1476 while a person standing within the mechanism bends the knee to perform squatting operations upward and downwardly. The control modules may be adjusted as all of them to provide a controlled pattern of exercise.

Figure 80:
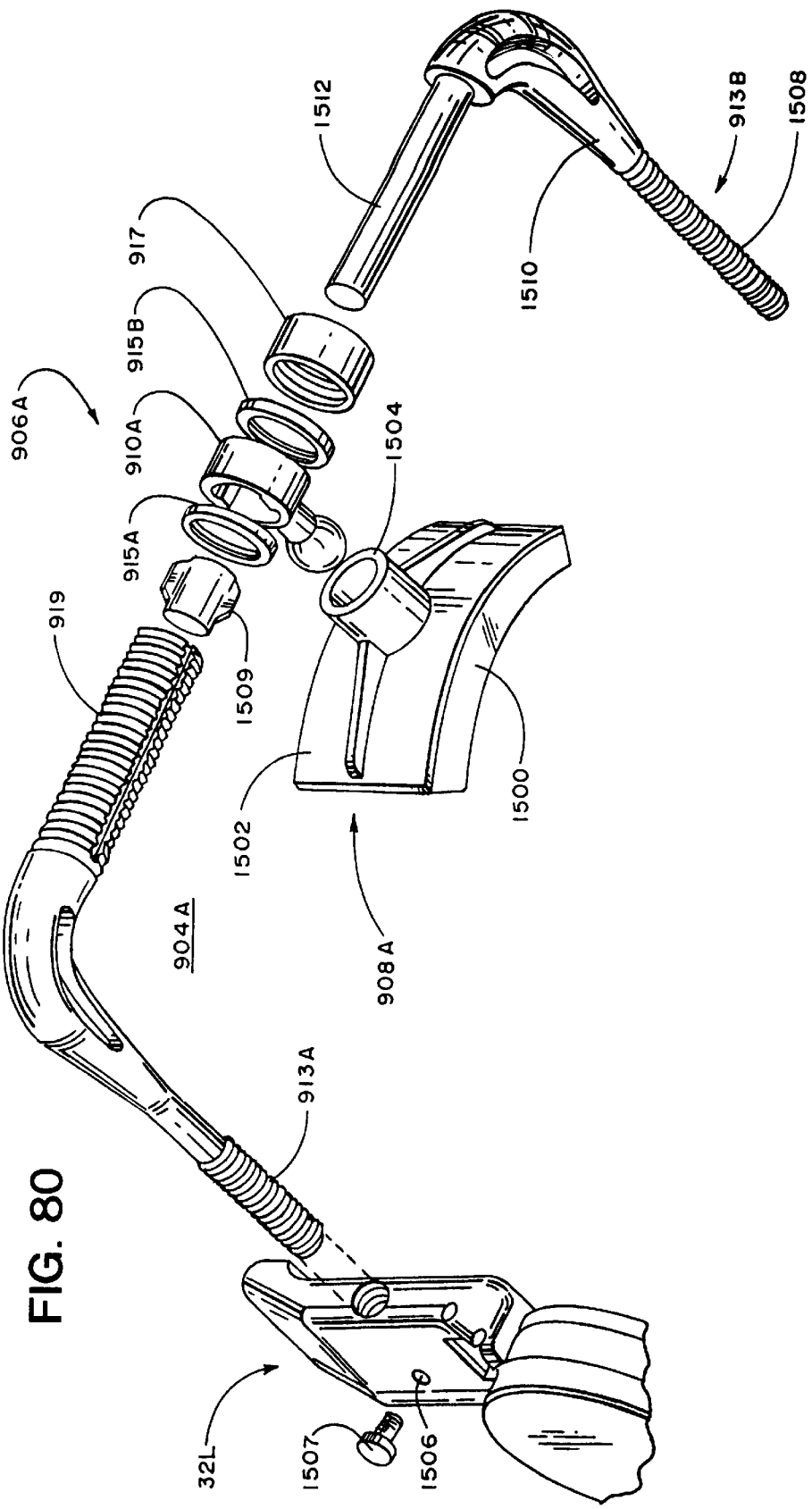
FIG. 80 is a fragmentary exploded perspective view of a tibia support useful in an embodiment of the invention.

In FIG. 80, there is shown a fragmentary, exploded, perspective view of a brace in accordance with the invention having a two-side support 904A, which may for example be a tibia support similar to the tibia support of FIG. 36, connecting the right and left sides of a brace together. For this purpose, the two-side support 904A includes a rigid interlocking brace section 906A, a cushion section 908A and right and left side sections 913A and 913B respectively.

The brace section 906A connects the right and left sides 913A and 913B in position with respect to each other and enables the cushion section 908A to be positioned to support body portion such as for example the tibia in position. For this purpose, the rigid portion 906A has a slidable fastener 910A, two threaded lock rings 915A and 915B, a split ferrule 1509, an internally threaded receiving socket 917, reduced shaft portion 1512 and a threaded, hollow base portion 906A. The reduced shaft portion 1512 fits within the threaded, hollow base portion 906A and forces the ferrule 1509 therebetween when the receiving socket 917 is threaded onto the base portion 906A. The slidable fastener 910 may be moved into a location to position the cushion section 908A and locked in place with the threaded lock rings 915A and 915B.

The cushion section 908A is mounted to a downwardly extending portion of the lock 910 so as to be moved from place to place by the lock 910A for positioning over the tibia. It includes a bottom cushion portion 1500 and a top support 1502 that is rigid enough to hold the body part in place with the cushion 1500 pressed against the skin of the patient. An upwardly extending socket 1504 from the rigid support 1502 receives a ball joint from the locking member 910A. It is pivotable thereabout but held in place laterally and longitudinally. A threaded screw 1507 may be forced against the members 913A and 913B through an internally tapped opening such as shown at 1506 in the adapter 32L for attachment to a brace.

In FIG. 81, there is shown a side elevational view of the left side support 913B having a first end 1508 with external threads thereon, a connecting portion 1510 and a reduced diameter brace portion 1512. The threaded end 1508 is adapted to fit within an opening in the adapter for a brace where it is held by a threaded screw and supports the connecting portion 1510 which extends outwardly and curves inwardly to form the brace portion.

The reduced diameter section 1512 is adapted to fit within the hollow, externally-threaded brace portion 919 to form an interfitting connection for the rigid center portion 906A of the brace. The internally-threaded receiving socket 917 is positioned on the right side member 913B between the reduced shaft portion 1502 and the connecting portion 1510 and includes within it an internally-threaded recess 1514 for receiving the end of the externally threaded portion 919 of base portion 906A and a reduced diameter recess that engages the end of the ferrule 1509 and forces it between the reduced diameter portion 1512 and inner wall of the hollow portion 919 to lock the two together as the receiving socket 917 is threaded onto the external threads of the hollow portion 919.

In FIG. 82, there is shown a front elevational view of the right side support 913B showing the central cylindrical shaft 1502 that fits within and correspondingly sized opening in the left side member 1913A to form the rigid center portion 906A, with the socket 917 at the opposite end.

In FIG. 83, there is shown an elevational view of the left side member 913A having the externally threaded shaft 906A, an internal bore 1520 extending longitudinally through the central axis of the section 906A, a pair of slots in a plane perpendicular to the plane of the side member 913A, one of which is shown at 1522, a connecting portion 1524 and an end mounting portion 1526 having a threaded end. The threaded end of the portion 1526 is inserted in the adapter and extends upwardly parallel to the end 1508 with a connecting section providing a connection with the perpendicularly extending end 106A. The distance between the external threads 906 are also sized to engage the internally threaded cylinder 917 which presses the ferrule 1526 between the shaft 1502 and the internal bore 1522 to adjust the distance between the sides 913A and 913B by holding the shaft firmly at a fixed location within the bore 1520.

In FIG. 84, there is shown the positioning member 910A having a cylindrical sleeve member 1530 which fits over the member 906A and is movable thereon, a downwardly extending shaft 1532 and a ball 1534. The ball 1534 is fastened to the sleeve 1530 by the downwardly extending rigid member 1532 and resides within the cushioned tibia support 908A.

In FIG. 85, there is shown an elevational view of the positinoing member 908A, having a socket 1504 adapted to receive the ball 1534 movably so as to permit adjustment of the sleeve 908A laterally along the member 906A by moving the slide 1530 therealong.

In FIG. 87 there is shown a top view of the tibia support 908A showing the socket 1504 which receives the ball 1534 which it can be inserted with pressure through its top and be locked in place. In FIG. 86, there is shown an internally threaded one of the rings 915A which is identical to the ring 915B. These narrow rings may be moved along the shaft 906A by threading them. They are intended to tightly confine the sleeve 1530.

With this mechanism, as best shown in FIG. 80, the two sides 913A and 913B may be inserted in apertures within the adapters 32L and 34L and held in place by the detents being pressed against them. The sleeve 910 may be positioned appropriately for the patient by threading the two rings 915A and 915B until the cushion 1500 is properly located. The two members 913A and 913B may be firmly fastened with the shaft 1502 within the bore 1520. The length may be adjusted and the two pulled together for firmness by threading the internally threaded sleeve 917 on the threads of the shaft 906A until the ferrule 1514 forms a tight friction seal between the outside of the shaft 1502 and the inner wall of the opening 1520 so as to firmly hold the shaft 1502 within the opening at a distance which is appropriate for the length between the adapters 32L and 34L with the two sides 1526 and 1510 parallel to each other.

Figure 88:
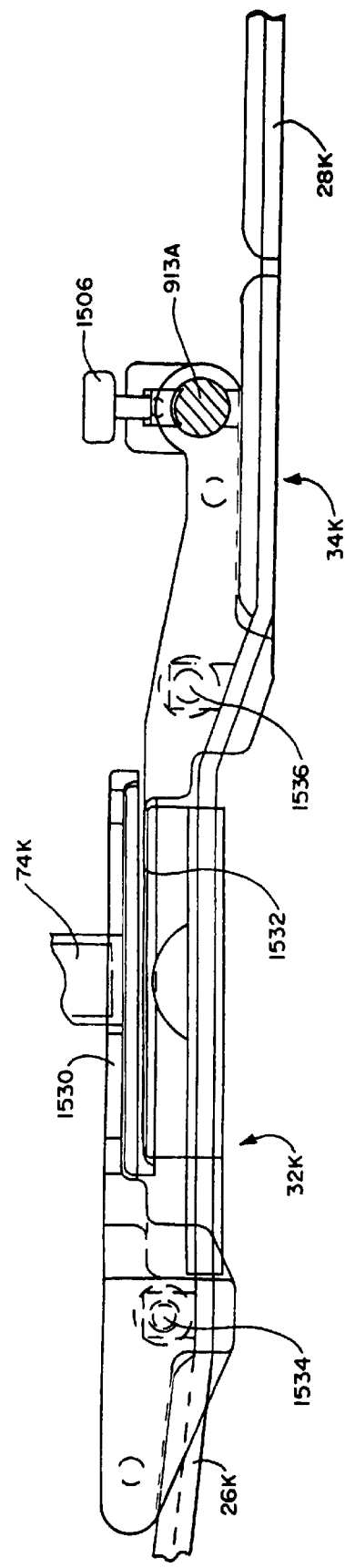
FIG. 88 is a fragmentary elevational view of a portion of a control module shown attached to a brace illustrating the manner of attachment.

In FIG. 88, there is shown first and second lever arms 32K and 34K fastened to first and second sections 26K and 28K respectively of a knee brace. These two lever portions 32K and 34K have their respective central disks 1530 and 1532 overlapping and interconnected to a control module over a knee joint. A bolt of the control module 74K being shown in fragmentary form.

The lever portions are adapted to snap over the brace parts in a manner similar to that described with respect to FIGS. 46–49 except that a single bolt holds the two snap on portions of the levers together, with the bolt 1534 holding a first portion snapped over the brace part to a second portion including the disk portion for the lever arm 32K and a bolt 1536 holding together the two portions of the lever arm 34A over the brace. Also, one of the two pairs of locks 1506 is shown engaging an end portion 913A (FIG. 80) to hold one side of the two side support 904A (FIG. 80) in place.

Figure 89:
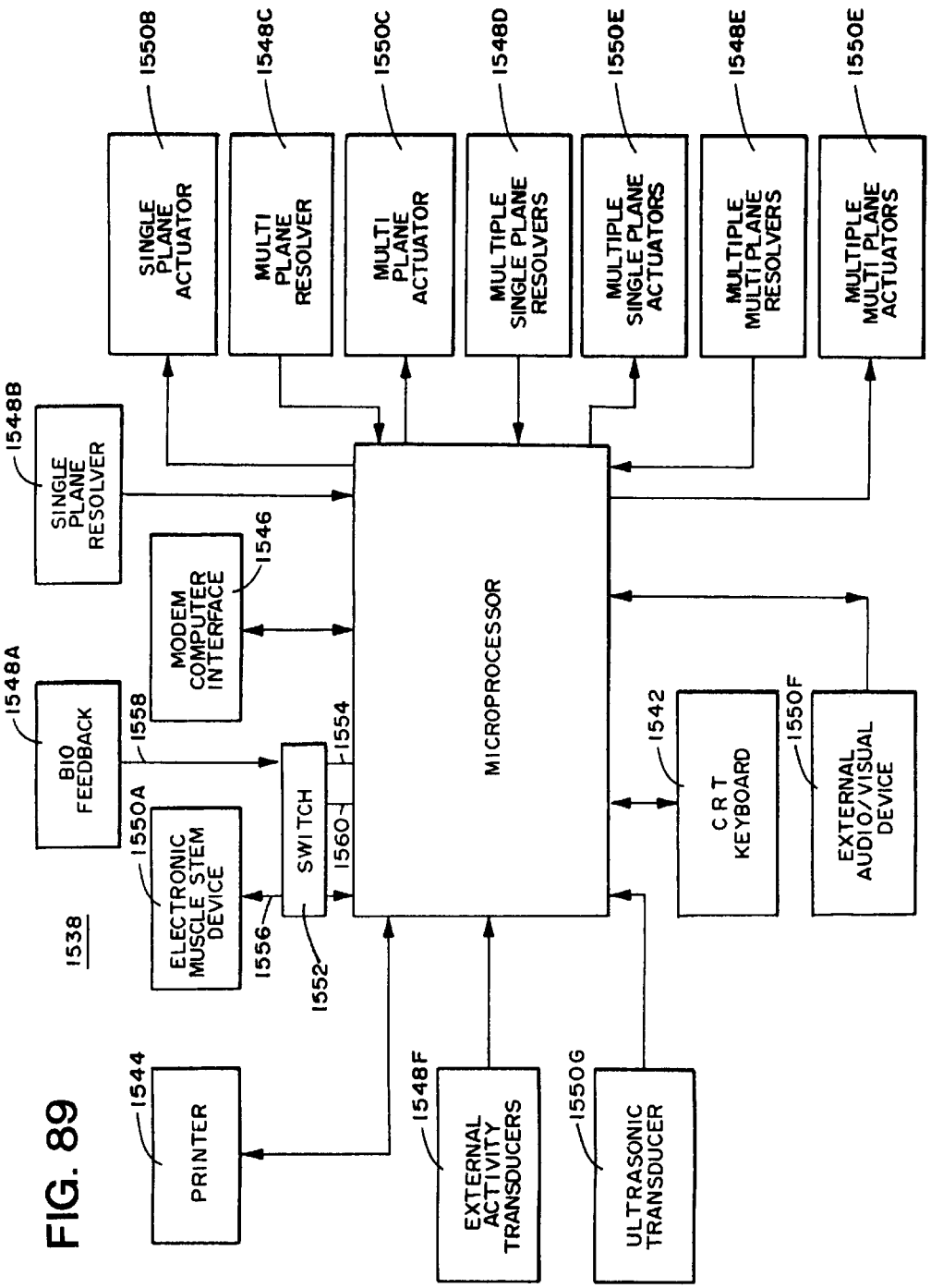
FIG. 89 is block diagram of a microprocessor controlled system useful in an embodiment of the invention.

In FIG. 89, there is shown a block diagram of the microprocessor control system 1538 having a microprocessor 1540, a combination cathode ray tube and keyboard 1542, a printer 1544, a modem 1546, a pluraltiy of sensors 1548A–1548F and a plurality of actuating devices 1550A–1550G. The CRT and keyboard combination 1542, the printer 1544, and the modem computer interface 1546 are all electically connected to the microprocessor to permit the transmission of information into the microprocessor and reading out of information from the microprocessor either to a user at a local station or at a remote station. The sensors 1548A–1548F send signals to the microprocessor representing: (1) positions of limbs about a joint or other body parts about a joint; (2) conditions of the muscle as represented by myotonic electrical activity; and/or (3) timing of activities such as signals from external transducers indicating a foot striking a floor or a certain amount of acceleration of a body part or a temperature or the like from the environment.

The actuating devices 1550A–1550G may: (1) change resistance in accordance with different recorded programs in the control modules being used by the user and the position of the user; or (2) apply electrical myographic signals or ultrasonic signals or heat or the like in conjunction with data in the microprocessor 1540 to which they are electrically connected. The sensors 1548A–1548F supply signals to the microprocessor 1540 which may be used to access data which can in turn be used to control the actuators as to time or amplitude or the like.

To provide communication between the microprocessor and the operators, a local station is provided with both display and entry means. For example a cathode ray tube may display data from the microprocessor and data can be entered by an operator through a keyboard although it can also be entered by tape or any other means. In the alternative, the microprocessor may send information for a printout to a printer 1544. For remote printing or viewing or transmission of data to another microprocessor or the like, a modem can be electrically connected so that a remote user may share some of the activity involved in providing exercise or therapy or the like to a user.

In the preferred embodiment, the microprocessor 1540 includes a microprocessor referred to as a smart block microprocessor core module, utilizing Z-world Engineering Z-180 microprocessor with two serial ports, Motorola 6800 Peripheral Interface Drive, bus connector, time/date clock, watchdog timer and power fail detector. The microprocessor may be purchased from Z-world Engineering, 1724 Picasso Avenue, Davis, Calif. 95616.

To provide for muscular stimulation to strengthen a muscular motion at a predetermined time, the EMS activator 1550A, has electrodes which may be held against the skin at one or more locations to stimulate selective muscles in a manner known in the art. This muscle stimulation may be utilized to strengthen muscles or to equalize muscle tone which are unequal in strengths on two sides of a body part such as the tibia. Thus, the patient may exercise without the leg being twisted by the unequal muscle strength or may walk with a brace or the like.

The stimulation of the muscle may be used alone and permit patients to be ambulatory when they otherwise would not be ambulatory. Patients which are subject to knee buckling under certain conditions may have a signal applied at the proper time to avoid the knee buckling. Several muscles may be stimulated in a timed sequence which may be timed by events such as a measured impact of the kind made by a heel striking a floor or a certain amount of stress being applied to a brace with a control module on it or the like. The signal for stimulation may be controlled by more than one source such as for example particular positions of bending a joint together with force on the joint or particular myotonic electrical activity generated by muscle action either by itself or in conjunction with force or angular position or any of the other sensing techniques.

The muscles may be stimulated in connection with varying the resistance of the control module as described herein above. Thus at particular levels of force or myotonic activity and joint position, either the resistance may be changed to provide additional support such as increasing the resistance of a control module within a knee brace to avoid buckling of the knee under certain conditions either together with recruiting additional muscle fiber through stimulation or as an alternative to strengthening the muscle depending on a signal received from the muscle itself.

Thus the microprocessor together with sensors and actuators may control resistance in the module to depend on the force needed to bend the module, conditions such as the weight being placed on an external transducer, time from a particular impact such as a foot striking the ground and signals which are generated by muscular activity. This resistance can be utilized to provide support, such as against knee buckling or provide a controlled resistance curve for exercise. The resistance may be mechanically programmed or may reside in a lookup table of the microprocessor, addressed by the signals coming from transducers or may be calculated by the microprocessor in the case of some simple curves which are subject to calculation.

The transducer for providing electrical stimulation to the selected muscles may be any of several commercial units such as for example the RESPOND II model manufactured by Medtronic and available form Medtronic, Inc., 7000 Central Avenue N.E., Minneapolis, Minn. 55432, United States of America, although there are other commercial units that can be used. The technique of using electrical muscle stimulation either for exercise or to aid handicapped persons in their movements is described in numerous publications such as "The Use of a Four Channel Electrical Stimulator as an Ambulatory Aid For Paraplegic Patients", Bajd, et al., *PHYSICAL THERAPY,* volume 63, n7, July, 1983, pages 1116–11120; "Electrically Elecitated Co-Contraction of Thigh Musculature After Anterior Cruciate Ligment Surgery", Delitto, et al., *PHYSICAL THERAPY,* volume 68, n1, January, 1988, pages 45–50; and "Muscular Strength Developmet by Electrical Stimulation in Healthy Individuals", Corrier, et al., *PHYSICAL THERAPY,* volume 63, n6, June, 1983, pages 915–920. The conditions for application are discussed in detail in "Electrotherapeutic Terminology in Physical Therapy", by the Section on Clinical Electrophysiology, American Physical Therapy Association, ISBN number 912452-77-3 available from the American Physical Therapy Association, 111 North Fairfax Street, Alexanderia, Va. 22314-1488.

The electrodes are generally positioned over the muscle within flat flexible fabric material approximately four inches by two inches with the electrodes protruding from the bottom surface. They may be held in place by bindings or any other suitable means such as straps or by being attached to the brace. The pulse duration varies with circumstances but is generally within the range of one half of a microsecond to 750 microseconds. The frequency may vary between a DC current up to a frequency of 750 pulses per second with a current in the range of one to 50 miliampers and a voltage of between 50 to 300 volts. The particular preferred voltages and currents are generally determined by the attending physical therapist or physician but typical ones are provided in the aforementioned manual on electrotherapeutic terminology.

The biofeedback transducers may be any of several known existing devices such as the Myotrac Rapic Scan transducers sold by Thought Technology Ltd. availabe from Thought Technology Ltd., RR #1 Rt. 9N, #380 West Chazy, N.Y. 12992 or the Cyborg, EMG sold under the model numbers J53 dual portable EMG and J33 portable EMG available from Cyborg Corporation, 342 West Avenue, Boston, Mass. 02135.

To provide isolation between the biofeedback transducers 1548A and the EMS device 1550A, a two-position relay switch 1552 is controlled by the microprocessor through a control signal on conductor 1554 to close the relay contacts against a conductor 1556 to the electronic muscle device to cause a high voltage signal to be applied at the time indicated by the microprocessor 1540 at the selected frequency and power. In the absence of a control signal on conductor 1554, a biofeedback signal from the unit for biofeedback 1548A is transmitted through a conductor 1558 and the normally closed contacts of the relay switch 1552 to the microprocessor through conductor 1560.

With this arrangement, signals may be periodically applied to the muscle to stimulate the muscle at the preprogrammed time such as when the biofeedback signal indicates that muscle contraction is at its maximum to enable full use of a limb working against the control module resistance or to stimulate the muscle to continue walking together with support in the opposite direction from a control module or against further resistance from the control module.

The external audio/visual devices 1550F may be monitors to be viewed by a therapist while exercise or therapy is being performed. They may be a screen mounted to the back or to a belt of a patient or may be connencted to a virtual reality head mask such as that shown in 1202 in FIG. 66 to provide sounds and three-dimensional views to be coordinated with exercise or training. A suitable description of the equipment useful in preparing the virtual reality display for use is provided in "Virtual Realty" in International Directory of Research Projects edited by Jeremy Thompson, JET Publishing, Aldershot, United Kingdom, ISBN 0-88736-862-X.

In FIG. 90, there is shown a block diagram 1561 of a software program for controlling a single plane control module comprising the start step 1560 for decreasing the force by the maximum number of steps to obtain a zero set point, the steps 1562 for fetching the appropriate data from a data lookup table within the memory of the computer and the steps 1564 for sending pulses to the control module to reach the desired potential. Any of the electrically controlled control modules may be used such as that shown in FIGS. 42–45 and FIGS. 74–76.

To obtain data from the microprocessor 1540 (FIG. 90), a series of steps 1562 includes the sub routines including the step 1566 of reading the input data port, the step 1568 of checking for valid data, the step 1570 of determining if the data has changed and the step 1572 of calculating or reading a data table for the incremental value needed for the new angle. The step 1566 causes an interrogation of the position of the single plane module from the control unit of the module. This readout, is compared with expected range of values in the decision step 1568 and if the value is not reasonable, the program goes back to step 1566. If it is then the decision block 1570 receives the data and compares it to the last readout. If it is the same, the program again recirculates back to the step 1566. If there has been a change, the new address is used to read a data table to provide values for changing the resistance in the control module and transmitting it to the series of step 1564.

To select the proper value, the incremental change called for by the steps of the subroutine 1562 are applied to the decision step 1574, which determines if the resistance is higher or lower. If it is higher, a signal is sent to the step 1576 to calculate the number of increased pulses to reach the proper level. These pulses are used in the step 1578 to cause the stepping motor in the actuator to move to a new position and thus provide a new resistance against movement in the control module. On the other hand, if the resistance is lowered, a signal is applied to step 1580 to calculate the pulses necessary to reach the proper level. This number is applied to the output decrease pulse terminal by the step 1582 to cause the lever arms to move to a new position and thus reduce the resistance to movement by the user.

Figure 91:
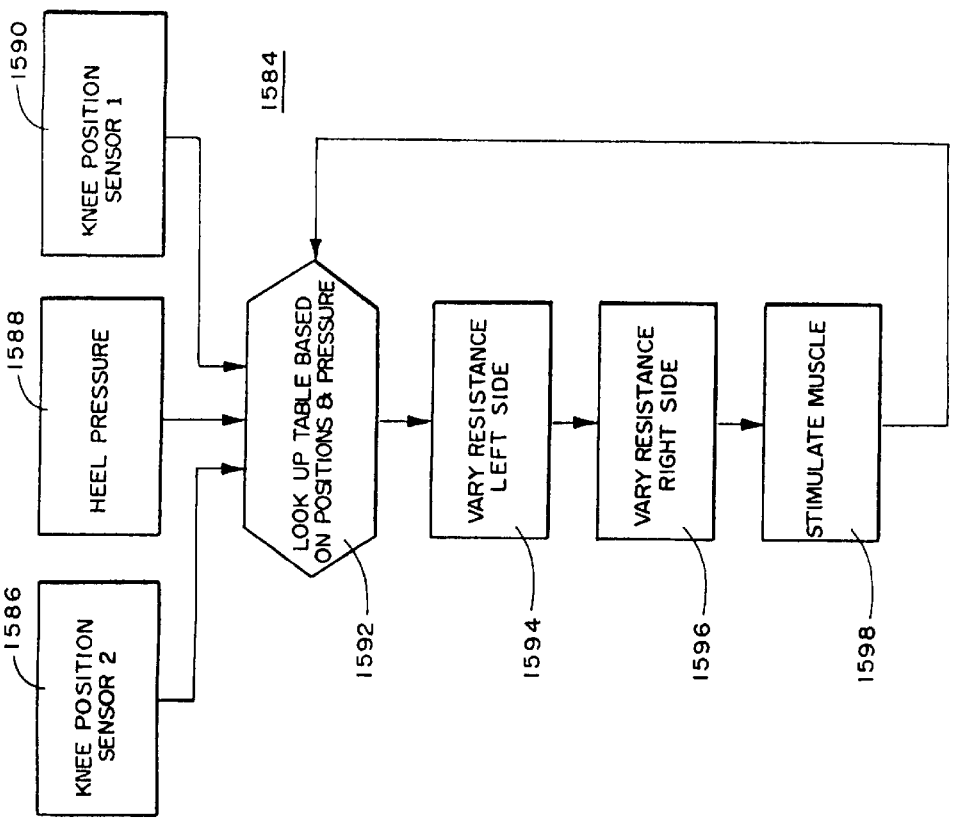
FIG. 91 is another flow diagram useful in practicing the invention.

In FIG. 91, there is shown a flow diagram 1584 including the step 1586 of reading a right or left side knee position sensor, the step 1588 of measuring the heel pressure, the step 1590 of sensing the other of the right or left hand position sensors, the step 1592 of using the readings received from the steps 1586, 1588 and 1590 to obtain a signal from a lookup table in the microprocessor 1540, the step 1594 receiving the signal from the microprocessor and varying the left side resistance, the step 1596 of receiving the signal and varying the right side resistance and the step 1598 of stimulating the muscle with an electrical signal, after which the loop is repeated to continue the steps so that the muscle is repeatedly stimulated at a predetermined frequency. The lookup table may for some values provide a zero bite in its transmitted word so that the right or the left side resistance modules may be unaltered or they may be each altered at a different value and the muscle may or may not be stimulated.

For example, some patients may have muscles in a knee which are not capable of being electrically stimulated to greater strength. In such a case, the word transmitted from the lookup table will have a zero value for EMS stimulation but will have values for the right and left resistance intended to keep the two resistances equal on each side of a knee brace but high enough so that the knee is prevented from buckling. On the other hand, there may only be a muscle stimulation signal for other patients. The particular values to be utilized will be determined by the therapist and preprogrammed into the computer by testing the patient ahead of time.

Figure 92:
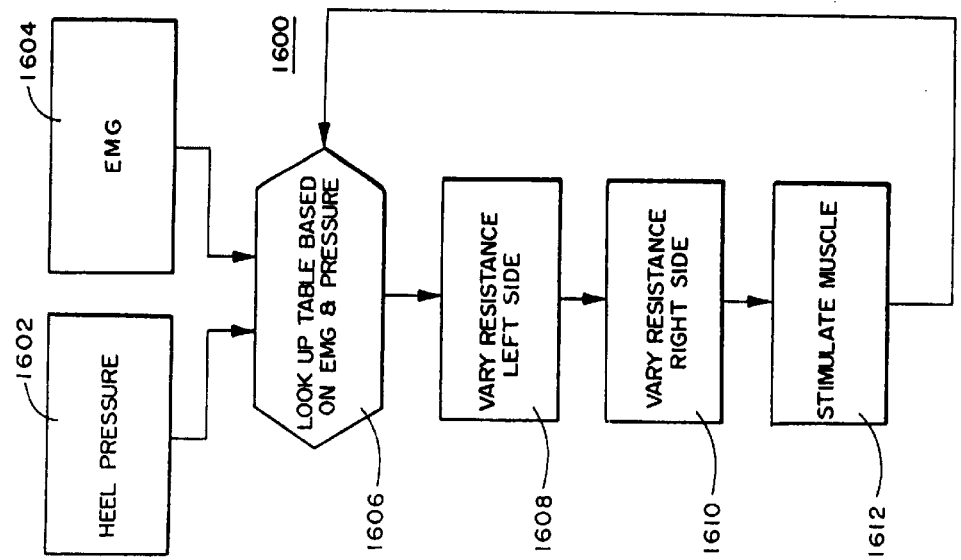
FIG. 92 is still another flow diagram useful in practicing the invention.

In FIG. 92, there is shown a program 1600 for changing the resistance in response to an EMG signal and a heel pressure signal only to detect the muscle condition such as maximum contraction during a walking operation. The program may then determine what values of resistance or stimulation should be used from a lookup table.

The program 1600 includes the step 1602 of measuring the heel pressure, the step 1604 of measuring the electrical myographic activity, the step 1606 of looking up a control word or sequence of words based on addresses from the steps 1602 and 1604, varying one of the right or left side resistances shown at step 1608, the step 1610 varying the other of the right or left side resistances and the step 1602 of stimulating the muscle. Again, the control word selected may have zero values for any of the resistances to be varied or the muscle stimulation electrical signal to be applied in accordance with the prerecorded information provided by the therapist. Thus, this program may be used for an exercise routine that enables a patient to walk when the patient otherwise would not be able to walk. This system may provide the timing of the stimulating signals in response to both a signal from the muscle indicating a maximum value and a timed position from the pressure transducer indicating where the portion of a step by the patient that is taking place.

Figure 93:
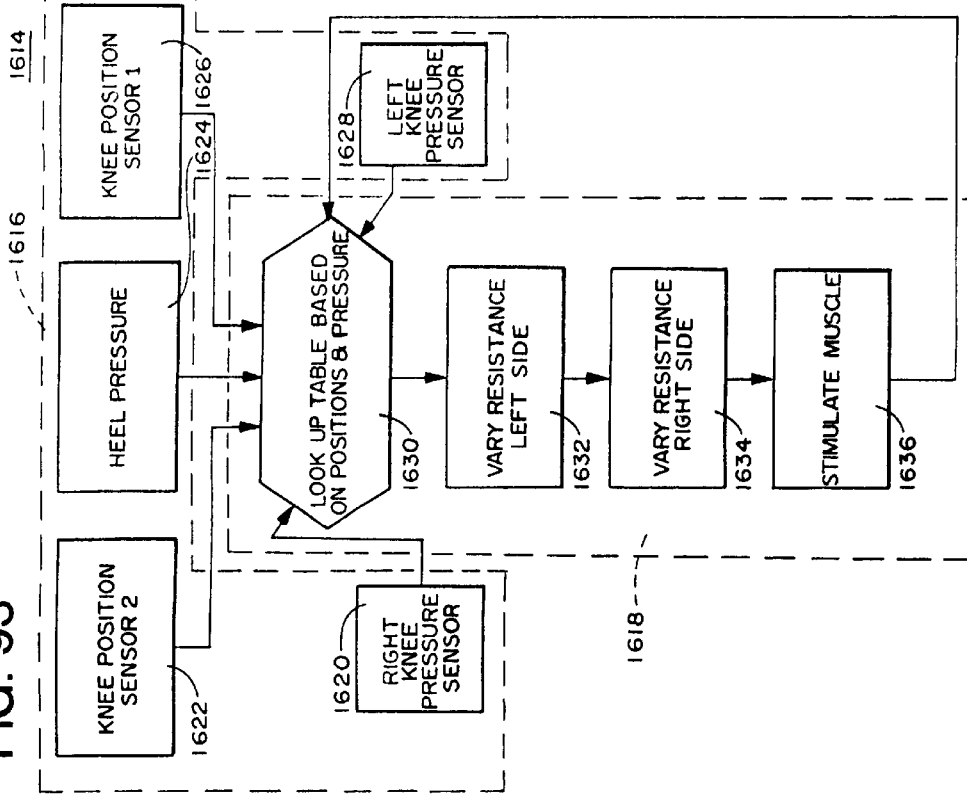
FIG. 93 is still another flow diagram useful in practicing the invention.

In FIG. 93, there is shown a program 1614 including the steps 1616 of: (1) sensing the pressure on a body part or other relevant sensed force such as heel pressure or acceleration of movement of a body part; (2) applying signals in response thereto and the steps 1618 of: (1) controling the time-resistance pattern applied by control modules, and if appropriate, the time of application of muscle stimulating electrical signals.

With this arrangement, both resistance and timing of a stimulating signal may be controlled by the amount of pressure applied to a knee, the pressure applied to a heel or the like indicating motion. Thus, twisting motions, such as those of a patient having a weakend patella, may be detected and corrected for by stimulating the weakened muscle and thus providing equal pressure and/or changing the resistances on each side.

To obtain control words for controlling the timing of and the amount of a muscle stimulation and the variations in the resistance, the group of program steps 1616 includes the step 1622 of sensing the position of one side of a body part such as a knee, the step 1626 of sensing the position of the other side of the body part, the step 1624 of sensing heel pressure, the step 1620 of sensing the pressure on one of the two sides of the body parts and the step 1628 of sensing the pressure on the other of the two body parts. This same arrangement may be used to sense the condition of two body parts such as two legs but an additional heel sensor would be included.

This information is applied to the group of steps 1618 which in turn responds with control words to stimulate muscles and/or to vary the appropriate resistances of a control module. The group of steps 1618 for this purpose includes: (1) the step 1630 of looking up in the prerecorded lookup table in the internal memory of the microprocessor 1540 the control words called for and preprogrammed by the therapist and applying the control words sequentially to the control modules; and (2) the resulting sequence of steps 1632, 1634 and 1636 setting the amount of resistance on any of the right or the left side and the nature of any muscle stimulation that is to be applied.

Figure 94:
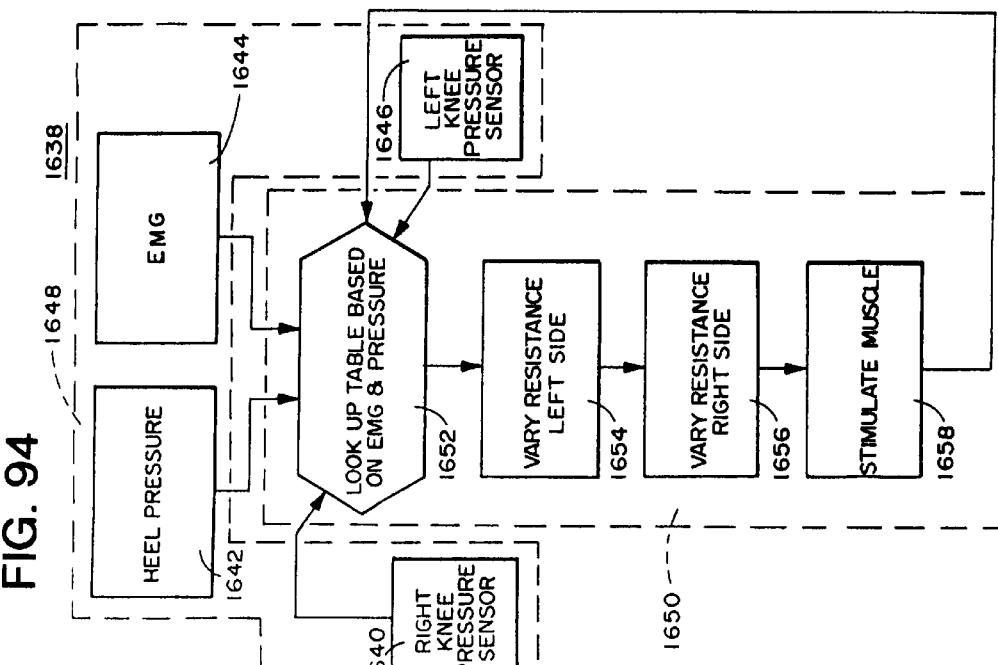
FIG. 94 is still another flow diagram useful in practicing the invention.

In FIG. 94, there is shown a flow diagram of a program 1638 for controlling the amount and timing of resistance changes and muscle stimulation based on biofeedback from the muscle electrical activity, heel pressure and pressure on the knee braces. For this purpose, the program 1638 includes a group of program steps 1648 for making the appropriate measurements and steps 1650 for determining the necessary changes in resistance, making the changes in resistance and providing stimulation for the muscles.

To provide the appropriate measurement data, the group of steps 1648 includes the step 1642 of measuring the heel pressure, the step 1644 of measuring muscle electrical activity, the step 1640 of measuring knee pressure on one side and the step 1646 of measuring torque pressure on the other knee. These signals are applied to the group of steps 1650 to make the appropriate corrections.

The group of steps 1650 includes the step 1652 of looking up control words in a control table based on electrical myographic values and pressure values and applying them to vary the resistance on the right or left side of the braces and stimulate muscles as shown by the sequence of steps 1654, 1656 and 1658.

Figure 95:
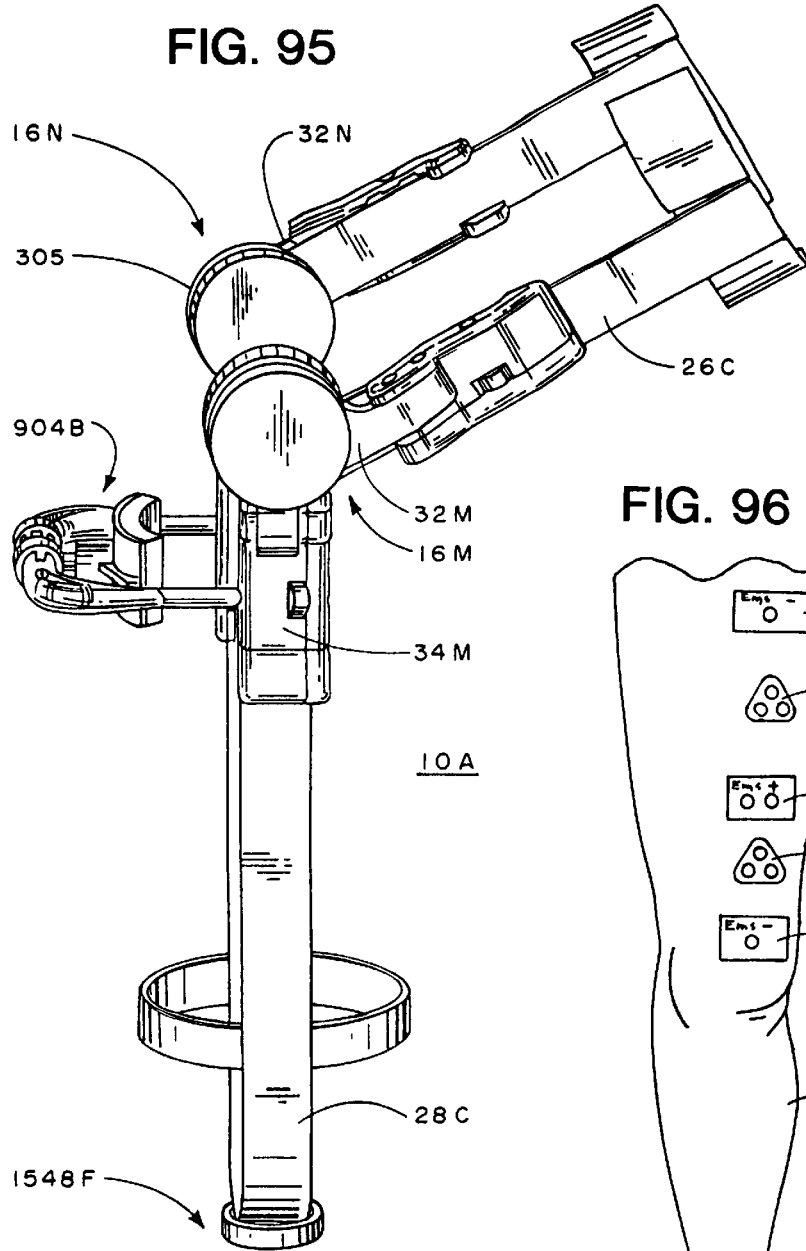
FIG. 95 is a perspective view showing another embodiment of the invention.

In FIG. 95, there is shown a perspective view of exercise or bracing apparatus 10A having an upper brace part 26C and a lower brace part 28C connected at joints 16N and 16M to form two sides of a brace such as a knee brace. The two sides of the brace are connected together by a tibia support 904B similar to that described in FIG. 80. At the bottom of the brace intended to be positioned on the foot is a transducer 1548F such as that described in FIG. 99 for providing indications of walking. The transducer may be a pressure transducer embedded in a relatively soft cushion material. The transducer itself may be as described in connection with FIG. 89.

Figure 96:
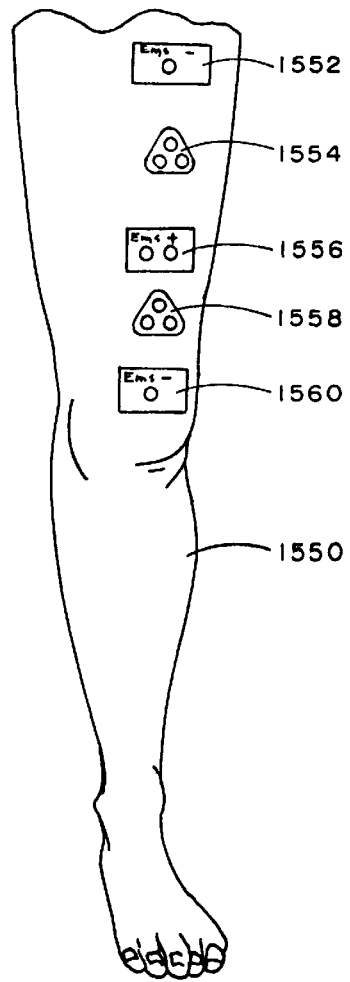
FIG. 96 is a diagramatic sketch showing possible placement of electrodes for use in an embodiment of the invention.

In FIG. 96, there is shown a fragmentary, simplified view of a leg 1550 having electrodes 1552, 1554, 1556, 1558 and 1560 positioned on the leg for measurement and for stimulation. The positions and the electrodes themselves are conventional and generally include and include sockets on the top surface for pin connectors, with the electrode 1552 including one socket for application of a negative potential used for stimulation over the femoral nerve, the electrode 1554 including three sockets for measurement of electrical myographic signals, the electrode 1556 including two sockets for positive potential used for stimulation located midway between the vastus medialis oblique muscle and the hip crease, the electrode 1558 including three sockets for measurement of electrical myographic signals in cooperation with the electrode 1554 and the electrode 1560 including one socket for application of negative potential over the vastus medialis oblique muscle in cooperation with the positive electrode 1556 and the other negative electrode 1552.

From the above description, it can be understood that the exercise device of this invention has several advantages, such as: (1) it can provide timed controlled resistance to movement in either direction; (2) it may be easily snapped onto existing braces to provide a controlled program of therapy without the need for expensive equipment; (3) it can provide a controlled and contoured resistance which depends on the position of the limb; (4) the controlled programs of resistance may be tailored to the individual and controlled by inserts into the exerciser.

While a preferred embodiment of the invention has been described with some particularity, many modifications and variations in the preferred embodiment can be made without deviating from the invention. Therefore, it can be understood that within the scope of the appended claims the invention can be practiced other than as specifically described.

What is claimed is:

1. A method of providing controlled exercise of a jointed portion of a person comprising the steps of:

attaching a jointed brace having a first section, a second section, and a brace joint means connecting said first section and second section wherein the first section is connected to a first portion of a person on one side of a joint of the person and the second section to a second portion of the person on the opposite side of the person's joint;

attaching control means to said first and second sections;

moving the first portion of the person with respect to the second portion of the person; and varying the resistance to movement of the first and second sections with respect to each other about said brace joint means through said control means wherein a predetermined resistance is provided for each position and direction of movement of the first section with respect to the second section independent of the rate of movement of the first section with respect to the second section;

the step of varying the resistance of movement including the step of resisting motion of movement of the jointed brace with a force dependent upon the position of the first section and the section section.

2. A method of providing controlled exercise of a jointed portion of a person comprising the steps of:

attaching a jointed brace having a first section, a second section, and a brace joint means connecting said first section and second section wherein the first section is connected to a first portion of a person on one side of a joint of the person and the second section to a second portion of the person on the opposite side of the person's joint;

attaching control means to said first and second sections;

moving the first portion of the person with respect to the second portion of the person; and varying the resistance to movement of the first and second sections with respect to each other about said brace joint means through said control means wherein a predetermined resistance is provided for each position and direction of movement of the first section with respect to the second section independent of the rate of movement of the first section with respect to the second section;

the step of varying the resistances including the step of varying the resistance over a portion of movement in accordance with a program means in the control means as a function of different angles between the first and second sections.

3. A method of providing controlled exercise of a jointed portion of a person comprising the steps of:

attaching a jointed brace having a first section, a second section, and a brace joint means connecting said first section and second section wherein the first section is connected to a first portion of a person on one side of a joint of the person and the second section to a second portion of the person on the opposite side of the person's joint;

attaching control means to said first and second sections;

moving the first portion of the person with respect to the second portion of the person; and varying the resistance to movement of the first and second sections with respect to each other about said brace joint means through said control means wherein a predetermined resistance is provided for each position and direction of movement of the first section with respect to the second section independent of the rate of movement of the first section with respect to the second section;

in which the step of varying the resistance including the substep of varying pressure between movable friction plates for controlling frictional force resisting to motion of the friction plates with respect to each other.

4. A method of providing controlled exercise of a jointed portion of a person comprising the steps of:

attaching a jointed brace having a first section, a second section, and a brace joint means connecting said first section and second section wherein the first section is connected to a first portion of a person on one side of a joint of the person and the second section to a second portion of the person on the opposite side of the person's joint;

attaching control means to said first and second sections;

moving the first portion of the person with respect to the second portion of the person; and varying the resistance to movement of the first and second sections with respect to each other about said brace joint means through said control means wherein a predetermined resistance is provided for each position and direction of movement of the first section with respect to the second section independent of the rate of movement of the first section with respect to the second section;

wherein the step of varying the resistance includes the substep of controlling friction in accordance with the amount of pressure between two friction members which engage each other and move with respect to each other as the first and second sections move;

wherein the substep of controlling friction includes the substep of changing the amount of pressure between the friction members as a function of the angle between the two sections.

5. A method in accordance with claim 4 in which the substeps of changing the amount of pressure includes the substep of actuating a cam means to press the friction members together at certain angular positions of the first section and the second section with respect to each other.

6. A method of providing controlled exercise of a jointed portion of a person comprising the steps of:

attaching a jointed brace having a first section, a second section, and a brace joint means connecting said first section and second section wherein the first section is connected to a first portion of a person on one side of a joint of the person and the second section to a second portion of the person on the opposite side of the person's joint;

attaching control means to said first and second sections;

moving the first portion of the person with respect to the second portion of the person; and varying the resistance to movement of the first and second sections with respect to each other about said brace joint means through said control means;

the step of varying the resistance including the substep of controlling friction in accordance with the amount of pressure between two friction members which engage each other and move with respect to each other as the first and second sections move;

the substep of controlling friction including the substep of changing the amount of pressure between the friction members as a function of the angle between the two sections;

the substeps of changing the amount of pressure including the substep of actuating a cam means to press the friction members together at certain angular positions of the first section and the second section with respect to each other; and the step of controlling pressure including the steps of engaging a first pair of friction members during rotation in one of clockwise and counterclockwise directions between said first and second sections and engaging a different combination of frictional members during the opposite of clockwise or counterclockwise movement of said first and second sections with respect to each other.

7. A method of therapy comprising the steps of:

attaching a jointed limb member having a first section, a second section, and a joint means connecting said first section and second section whereby the first section is connected to a portion of a limb of a person on one side of a joint of the limb and the second section to a portion of a limb of a person on the opposite side of the joint of the limb; and periodically attaching control means to said first and second sections adjacent to said joint means for varying the resistance to movement of the first and second sections with respect to each other about said joint means wherein the amount of resistance is independent of the rate of movement;

exercising the limb while said control means is attached;

removing said control means after said exercise;

wherein a program means varies a resistance force over a portion of movement in accordance with the program means at different angles between the first and second sections.

8. A method of therapy comprising the steps of:

attaching a jointed limb member having a first section, a second section, and a joint means connecting said first section and second section whereby the first section is connected to a portion of a limb of a person on one side of a joint of the limb and the second section to a portion of a limb of a person on the opposite side of the joint of the limb;

periodically attaching control means to said first and second sections adjacent to said joint means for varying the resistance to movement of the first and second sections with respect to each other about said joint means wherein the amount of resistance is independent of the rate of movement;

exercising the limb while said control means is attached;

removing said control means after said exercise;

providing a resistance force against movement of said sections in at least one of clockwise or counterclockwise movement about said joint means;

wherein said friction is provided by friction means and the friction means is controlled by the amount of pressure between two friction members which engage each other and move with respect to each other as first and second sections move, and the amount of pressure is controlled by differences in the pressure between two members as the angle between the two sections changes.

9. A method in accordance with claim 8 in which a camming mechanism presses the members together at certain angular positions of the first section with respect to the second section.

10. A method of therapy comprising the steps of:

attaching a jointed limb member having a first section, a second section, and a joint means connecting said first section and second section whereby the first section is connected to a portion of a limb of a person on one side of a joint of the limb and the second section to a portion of a limb of a person on the opposite side of the joint of the limb;

periodically attaching control means to said first and second sections adjacent to said joint means for varying the resistance to movement of the first and second sections with respect to each other about said joint means;

exercising the limb while said control means is attached;

removing said control means after said exercise; and providing a resistance force against movement of said sections in at least one of clockwise or counterclockwise movement about said joint means, wherein the friction means is controlled by the amount of pressure between two friction members which engage each other and move with respect to each other as first and second sections move, the amount of pressure is controlled by differences in the pressure between two members as the angle between the two sections changes, and a camming mechanism presses the members together at certain angular positions of the first section with respect to the second section;

a first pair of friction members engaging each other during rotation in one of clockwise and counterclockwise directions between said first and second sections and a different combination of frictional members engaging each other during the opposite of clockwise or counterclockwise movement of said first and second sections with respect to each other.

11. A method of making exercise apparatus comprising:

attaching a first section to a first portion of a brace joint means, a second section to a second portion of a brace joint means with said first section and second section movably attached to the brace joint means whereby the first section may be connected to a portion of a limb of a person on one side of a joint of the limb and the second section to a portion of a limb of a person on the opposite side of the joint of the limb;

wherein the force means has program means inserted for varying resistance force over a portion of movement in accordance with the program means at different angles between the first and second sections.

12. A method comprising:

attaching a first section to a first portion of a brace joint means, a second section to a second portion of a brace joint means with said first section and second section movably attached to the brace joint means whereby the first section may be connected to a portion of a limb of a person on one side of a joint of the limb and the second section to a portion of a limb of a person on the opposite side of the joint of the limb;

providing controllable force means between said first and second portions for varying the resistance of movement of the first and second sections with respect to each other about said brace joint means in such a manner as to reduce ortho-kinetic joint movement discord;

said force means is adjusted to provide a resistance force against movement of said sections in at least one of clockwise or counterclockwise movement about said brace joint means;

wherein the friction means is controlled by the amount of pressure between two friction members which engage each other and move with respect to each other as first and second sections move;

wherein the amount of pressure is controlled by differences in the pressure between two members as the angle between the two sections changes.

13. A method in accordance with claim 12 wherein a camming mechanism presses the members together at certain angular positions of the first section with respect to the second section.

14. A method of making an exercise apparatus comprising:

attaching a first section to a first portion of a brace joint means, a second section to a second portion of a brace joint means with said first section and second section movably attached to the brace joint means whereby the first section may be connected to a portion of a limb of a person on one side of a joint of the limb and the second section to a portion of a limb of a person on the opposite side of the joint of the limb; and providing controllable force means between said first and second portions for varying the resistance of movement of the first and second sections with respect to each other about said brace joint means in such a manner as to reduce ortho-kinetic joint movement discord;

said force means being adjusted to provide a resistance force against movement of said sections in at least one of clockwise or counterclockwise movement about said brace joint means;

the friction means being controlled by the amount of pressure between two friction members which engage each other and move with respect to each other as first and second sections move; wherein the amount of pressure is controlled by differences in the pressure between two members as the angle between the two sections chances; a camming mechanism presses the members together at certain angular positions of the first section with respect to the second section;

a first pair of friction members engaging each other during rotation in one of clockwise and counterclockwise directions between said first and second sections and a different combination of frictional members engaging each other during the opposite of clockwise or counterclockwise movement of said first and second sections with respect to each other.

* * * * *